(12) United States Patent
Lin et al.

(10) Patent No.: US 8,246,999 B2
(45) Date of Patent: Aug. 21, 2012

(54) CAPPED MESOPOROUS SILICATES

(75) Inventors: Victor Shang-Yi Lin, Ames, IA (US); Cheng-Yu Lai, Ames, IA (US); Srdija Jeftinija, Ames, IA (US); Dusan M. Jeftinija, Lexington, KY (US)

(73) Assignee: Iowa State University Research Foundation, Inc., Ames, IA (US)

( * ) Notice: Subject to any disclaimer, the term of this patent is extended or adjusted under 35 U.S.C. 154(b) by 608 days.

(21) Appl. No.: 12/411,869

(22) Filed: Mar. 26, 2009

(65) Prior Publication Data
US 2009/0252811 A1 Oct. 8, 2009

Related U.S. Application Data

(63) Continuation of application No. 10/830,479, filed on Apr. 22, 2004, now Pat. No. 7,563,451.

(60) Provisional application No. 60/489,043, filed on Jul. 22, 2003.

(51) Int. Cl.
*A61K 9/14* (2006.01)
*A61K 9/50* (2006.01)
*B32B 5/16* (2006.01)

(52) U.S. Cl. ..... 424/502; 424/489; 424/501; 428/402.2; 428/402.22

(58) Field of Classification Search .......... None
See application file for complete search history.

(56) References Cited

U.S. PATENT DOCUMENTS

| | | | |
|---|---|---|---|
| 4,062,965 A | 12/1977 | Holtschmidt et al. | |
| 4,522,806 A | 6/1985 | Muhlemann et al. | |
| 5,051,533 A | 9/1991 | Verkade et al. | |
| 5,104,515 A | 4/1992 | Chu et al. | |
| 5,110,572 A | 5/1992 | Calabro et al. | |
| 5,143,879 A | 9/1992 | Whitehurst | |
| 5,145,816 A | 9/1992 | Beck et al. | |
| 5,156,828 A | 10/1992 | Degnan et al. | |
| 5,156,829 A | 10/1992 | McCullen et al. | |
| 5,198,203 A | 3/1993 | Kresge et al. | |
| 5,364,797 A | 11/1994 | Olson et al. | |
| 5,380,947 A | 1/1995 | Chen et al. | |
| 5,525,126 A | 6/1996 | Basu et al. | |
| 5,629,282 A | 5/1997 | Bhakoo | |
| 5,922,635 A | 7/1999 | Olah et al. | |
| 5,951,962 A | 9/1999 | Muller et al. | |
| 5,965,264 A | 10/1999 | Barenberg et al. | |
| 6,204,424 B1 | 3/2001 | Yadav et al. | |
| 6,475,497 B1 | 11/2002 | Rajaiah et al. | |
| 6,696,258 B1 | 2/2004 | Wei et al. | |
| 6,723,862 B2 | 4/2004 | Shuguang et al. | |
| 6,863,942 B2 | 3/2005 | Ren et al. | |
| 6,969,693 B2 | 11/2005 | Sauvage et al. | |
| 7,122,688 B2 | 10/2006 | Lin et al. | |
| 7,195,780 B2 * | 3/2007 | Dennis et al. | 424/502 |
| 2002/0164380 A1 | 11/2002 | Ma et al. | |
| 2004/0213996 A1 | 10/2004 | Fujiwara et al. | |
| 2005/0015258 A1 | 1/2005 | Somani et al. | |
| 2005/0107624 A1 | 5/2005 | Lin et al. | |
| 2005/0176978 A1 | 8/2005 | Verkade et al. | |
| 2006/0018966 A1 | 1/2006 | Lin et al. | |
| 2006/0120955 A1 | 6/2006 | Miyata | |
| 2006/0154069 A1 | 7/2006 | Lin et al. | |

FOREIGN PATENT DOCUMENTS

| | | |
|---|---|---|
| EP | 0566047 A2 | 10/1993 |
| WO | WO-2005/009602 A2 | 2/2005 |
| WO | WO-2006/034239 A2 | 3/2006 |

OTHER PUBLICATIONS

Moller, K., "Synthesis of Ordered Mesoporous Methacrylate Hybrid Systems: Hosts for Molecular polymer Composites", 1999, Chem. Mater., 11, pp. 665-673.*

Nooney, R.I., et al., "Synthesis of Nanoscale Mesoporous Silica Spheres with Controlled Particle Size", 2002, Chem. Mater., 14, 4721-4728.*

Ottaviani, M.F., et alo., "EPR Investigation of the Adsorption of Dendrimers on Porous Surfaces", 2003, J. Phys. Chem B, 107, pp. 2046-2053.*

Esumi, K., et al., "Adsorption of poly(ethyleneglycol) and poly(amidoamine)dendrimer from their mixtures on alumina/water and silica/water interfaces", 2001, Colloids and Surfaces, 194, pp. 7-12.*

Azamian, B. R., et al., "Directly observed covalent coupling of quantum dots to single-wall carbon nanotubes", 2002, Chem Commun., pp. 366-367.*

"Adhesive-Types of Adhesive Bonding", [online]. © 2007 Net Industries. [archived Nov. 2, 2007]. Retrieved from the Internet: <URL: http://science.jrank.org/pages/87/Adhesive-Types-adhesive-bonding.html>, (2007), 1 pg.

"U.S. Appl. No. 10/830,479, Response filed Oct. 1, 2008 to Final Office Action mailed Aug. 1, 2008", 11 pgs.

"U.S. Appl. No. 10/830,479, Response filed Nov. 25, 2008 to Final Office Action mailed Aug. 1, 2008 and Advisory Action mailed Oct. 31, 2008", 12 pgs.

"U.S. Appl. No. 10/830,479, Advisory Action mailed Oct. 31, 2008", 3 pgs.

"U.S. Appl. No. 10/830,479, Supplemental Notice of Allowability mailed Feb. 17, 2009", 2 pgs.

"U.S. Appl. No. 10/830,479, Notice of Allowance mailed Jan. 9, 2009", 4 pgs.

"U.S. Appl. No. 10/830,479, Non-Final Office Action mailed Nov. 9, 2007", 9 pgs.

(Continued)

*Primary Examiner* — Michael G Hartley
*Assistant Examiner* — Lance Rider
(74) *Attorney, Agent, or Firm* — Schwegman, Lundberg & Woessner, P.A.

(57) ABSTRACT

The invention provides an article comprising, a mesoporous silicate matrix, such as a particle, having one or more pores; and one or more releasable caps obstructing one or more of the pores. The articles are useful as delivery vehicles for encapsulated agents such as therapeutic agents, polynucleotides, polypeptides and the like.

22 Claims, 29 Drawing Sheets

OTHER PUBLICATIONS

"U.S. Appl. No. 10/830,479, Response filed Apr. 9, 2008 to Non-Final Ofice Action mailed Nov. 9, 2007", 14 pgs.

"U.S. Appl. No. 10/830,479, Final Office Action mailed Aug. 1, 2008", 7 pgs.

"U.S. Appl. No. 10/830,479, Response filed Oct. 8, 2007 to Restriction Requirement mailed Aug. 8, 2007", 8 pgs.

"U.S. Appl. No. 10/830,479, Restriction Requirement mailed Aug. 8, 2007", 8 pgs.

"U.S. Appl. No. 10/945,545, Response filed Oct. 20, 2008 to Non Final Office Action mailed Jun. 20, 2008", 15 pgs.

"U.S. Appl. No. 10/945,545, Non-Final Office Action mailed Jun. 20, 2008", 21 pgs.

"U.S. Appl. No. 10/945,545, Final Office Action mailed Jan. 28, 2009", 19 pgs.

"U.S. Appl. No. 10/989,540 Final Office Action mailed Sep. 11, 2006", 7 pgs.

"U.S. Appl. No. 10/989,540 Non Final Office Action mailed Apr. 13, 2006", 10 pgs.

"U.S. Appl. No. 10/989,540 Response filed Jun. 14, 2006 to Non Final Office Action mailed Apr. 13, 2006", 6 pgs.

"International Application Serial No. PCT/US04/23468, International Search Report mailed Apr. 11, 2006", 2 pgs.

"International Application Serial No. PCT/US04/23468, Written Opinion mailed Apr. 11, 2006", 5 pgs.

"International Application Serial No. PCT/US05/33578, International Search Report mailed Jun. 16, 2006", 3 pgs.

"International Application Serial No. PCT/US05/33578, Written Opinion mailed Jun. 16, 2006", 6 pgs.

"Methyl Soyate Shows Promise as Natural Solvent", *Feedstocks*, 3(2), (1998), 4 pgs.

"Physical and Cleaning Performance Properties of Methyl Soyate", *Report*, USB Project No. 7429, Omnitech International, Ltd., (1997), 1 pg.

"Process Pumps Up Biodiesel's Potential", *2003 Annual Report, Plant Sciences Institute*, (2002), 1 pg.

"Soy Methyl Ester Solvents—Technical Background", *United Soybean Board (USB) Newsletter*, (2002), 2 pgs.

"This Issue Summary", *Nature Nanotechnology*, 2(5), (May 2007), 1 pg.

Anderson, M. T., et al., "Effect of Methanol Concentration on CTAB Micellization and on the Formation of Surfactant-Templated Silica (STS)", *Chemistry of Materials*, 10, (1998), 1490-1500.

Andersson, J., et al., "Mesoporous Silica: An Alternative Diffusion Controlled Drug Delivery System", *Topics in Multifunctional Biomaterials and Devices*, Ashammakhi, N., Editor, (2008), 1-19.

Anwander, R., et al., "Enhanced catalytic activity of MCM-41-grafted aluminum isopropoxide in MPV reductions", *Chem. Commun.*, (1998), 1811-1812.

Aughenbaugh, W., et al., "Silica sol-gel for the controlled release of antibiotics. II. The effect of synthesis parameters on the in vitro release kinetics of vancomycin", *J. Biomed. Mater. Res.*, 57(2), (2001), 321-326.

Babonneau, F., et al., "Structural characterization of organically-modified porous silicates synthesized using $CTA^+$ surfactant and acidic conditions", *Journal of Materials Chemistry*, 9(1), (1999), 175-178.

Bagshaw, S. A., et al., "Templating of Mesoporous Molecular Sieves by Nonionic Polyethylene Oxide Surfactants", *Science*, 269(5228), (1995), 1242-1244.

Baker, Jr., J. R., et al., "The Synthesis and Testing of Anti-Cancer Therapeutic Nanodevices", *Biomedical Microdevices*, 3(1), (2001), 61-69.

Beck, J. S., et al., "A New Family of Mesoporous Molecular Sieves Prepared With Liquid Crystal Templates", *Journal of the American Chemical Society*, 114(27), (1992), 10834-10843.

Beck, J. S., et al., "Molecular or Supramolecular Templating: Defining the Role of Surfactant Chemistry in the Formation of Microporous and Mesoporous Molecular Sieves", *Chemistry of Materials*, 6(10), (1994), 1816-1821.

Bender, M., "Economic Feasibility Review for Community-Scale Farmer Cooperatives for Biodiesel", *Bioresource Technology*, 70, (1999), 81-87.

Boocock, D. G. B., et al., "Fast Formation of High-Purity Methyl Esters from Vegetable Oils", *JAOCS*, 75(9), (1998), 1167-1172.

Bossaert, W. D., et al., "Mesoporous Sulfonic Acids as Selective Heterogeneous Catalysts for the Synthesis of Monoglycerides", *Journal of Catalysis*, 182(1), (1999), 156-164.

Brown, J., et al., "Selective adsorption of $Hg^{2+}$ by thiol-functionalized nanoporous silica", *Chem. Commun.*, (1999), 69-70.

Burleigh, M. C., et al., "Amine-Functionalized Periodic Mesoporous Organosilicas", *Chemicals of Materials*, 13(12), (2001), 4760-4766.

Burleigh, M. C., et al., "Direct Synthesis of Periodic Mesoporous Organosilicas: Functional Incorporation by Co-condensation with Organosilanes", *The Journal of Physical Chemistry B*, 105(41), (2001), 9935-9942.

Burleigh, M. C., et al., "Imprinted Polysilsesquioxanes for the Enhanced Recognition of Metal Ions", *Chemistry of Materials*, 13(8), (2001), 2537-2546.

Cai, Q., et al., "Dilute Solution Routes to Various Controllable Morphologies of MCM-41 Silica with a Basic Medium", *Chemistry of Materials*, 13(2), (2001), 258-263.

Clardy, J C, et al., "Crystal and molecular structure of the caged amino phosphorus molecules $OP(NMeCH_2)_3CMe$ and $H_3BP(NmeCH_2)_3CMe$", *Phosphorus*, 4(3), (1974), 133-141.

Colvin, V. L., et al., "Semiconductor nanocrystals covalently bound to metal surfaces with self-assembled monolayers", *Journal of the American Chemical Society*, 114(13), (1992), 5221-5230.

Corma, A., "From Microporous to Mesoporous Molecular Sieve Materials and Their Use in Catalysis", *Chemical Reviews*, 97(6), (1997), 2373-2420.

Dai, S., et al., "Imprint Coating: A Novel Synthesis of Selective Functionalized Ordered Mesoporous Sorbents", *Angew. Chem. Int. Ed.*, 38(9), (1999), 1235-1239.

Davis, M. E., "Ordered porous materials for emerging applications", *Nature*, 417, (2002), 813-821.

Denning, J., et al., "Gene transfer into eukaryotic cells using activated polyamidoamine dendrimers", *Reviews in Molecular Biotechnology*, 90, (2002), 339-347.

Descalzo, A. B., et al., "A New Approach to Chemosensors for Anions Using MCM-41 Grafted with Amino Groups", *Advanced Materials*, 14(No. 13-14), (2002), 966-969.

Diasakou, M., et al., "Kinetics of the Non-Catalytic Transesterification of Soybean Oil", *Fuel*, 77(12), (1998), 1297-1302.

Díaz, I., et al., "A Direct Synthesis Route to the Mesoporous Silicate SBA-2 Bearing Thiol Groups", *Studies in Surface Science and Catalysis*, 135, (2001), 1248-1253.

Díaz, I., et al., "Combined Alkyl and Sulfonic Acid Functionalization of MCM-41-Type Silica", *Journal of Catalysis*, 193, (2000), 295-302.

Díaz, I., et al., "Synthesis of MCM-41 Materials Functionalised With Dialkylsilane Groups and Their Catalytic Activity in the Esterification of Glycerol With Fatty Acids", *Applied Catalysis A: General*, 242, (2003), 161-169.

Díaz, J. F., et al., "Enzyme immobolization in MCM-41 molecular sieve", *Journal of Molecular Catalysis B: Enzymatic 2*, (1996), 115-126.

Ebright, Y. W., et al., "S-[2-(4-Azidosalicylamido)ethylthio]-2-thiopyridine: Radioiodinatable, Cleavable, Photoactivatable Cross-Linking Agent", *Bioconjugate Chemistry*, 7(3), (1996), 380-384.

Encinar, J. M., et al., "Preparation and Properties of Biodiesel from *Cynara cardunculus* L. Oil", *Industrial & Engineering Chemistry Research*, 38(8), (1999), 2927-2931.

Esfand, R., et al., "Poly(amidoamine) (PAMAM) dendrimers: from biomimicry to drug delivery and biomedical applications", *Drug Discovery Today*, 6(8), (2001), 427-436.

Etienne, M., et al., "Organically-modified mesoporous silica spheres with MCM-41 architecture", *New J. Chem.*, 26, (2002), 384-386.

Fan, H, et al., "Rapid prototyping of patterned functional nanostructures", *Nature*, 405(6782), (May 4, 2000), 56-60.

Feng, X., et al., "Functionalized monolayers on ordered mesoporous supports", *Science*, 276, (1997), 923-926.

Fowler, C. E., et al., "Covalent coupling of an organic chromophore into functionalized MCM-41 mesophases by template-directed co-condensation", *Chem. Commun.*, (1998), 1825-1826.

Fowler, C. E., et al., "Nanoscale Materials with Mesostructured Interiors", *Advanced Materials*, 13(9), (2001), 649-652.

Fowler, C. E., et al., "Synthesis and characteristics of ordered organo-silica-surfactant mesophases with functionalized MCM-41-type architecture", *Chem. Commun.*, (1997), 1769-1770.

Freedman, B., et al., "Transesterification Kinetics of Soybean Oil", *JAOCS*, 63(10), (1986), 1375-1380.

Galbraith, D. W, "Silica breaks through in plants", *Nature Nanotechnology*, 2, (2007), 272-273.

Gruenhagen, J. A., et al., "Real-Time Imaging of Tunable Adenosine 5-Triphosphate Release from an MCM-41-Type Mesoporous Silica Nanosphere-Based Delivery System", *Applied Spectroscopy*, 59(4), (2005), 424-431.

Gryglewicz, S, "Rapeseed oil methyl esters preparation using heterogeneous catalysts", *Bioresource Technology*, vol. 70, (1999), 249-253.

Grynkiewicz, G., et al., "A New Generation of $Ca^{2+}$ Indicators with Greatly Improved Fluorescence Properties", *J Biol Chem.*, 260(6), (1985), 3440-3450.

Gupta, et al., "Hydrogels: from controlled release to pH-responsive drug delivery", *Drug Discovery Today*, 7(10), (2002), 569-579.

Hall, S. R., et al., "Template-directed synthesis of bi-functionalized organo-MCM-41 and phenyl-MCM-48 silica mesophases", *Chem. Commun.*, (1999), 201-202.

Han, Y.-J., et al., "Mesoporous Silicate Sequestration and Release of Proteins", *Journal of the American Chemical Society*, 121(42), (1999), 9897-9898.

He, X., et al., "Recent Advances in Synthesis and Applications of Transition Metal Containing Mesoporous Molecular Sieves", *Angew. Chem. Int. Ed.*, 41, (2002), 214-229.

He, X.-X., et al., "Bioconjugated Nanoparticles for DNA Protection from Cleavage", *Journal of the American Chemical Society*, 125(24), (2003), 7168-7169.

Hirai, T., et al., "Size-selective incorporation of CdS nanoparticles into mesoporous Silica", *J. Phys. Chem. B*, (May 1, 1999), 4228-4230.

Hossain, K. Z., et al., "Intraframework Metal Ion Adsorption in Ligand-Functionalized Mesoporous Silica", *Advanced Materials*, 14(15), (2002), 1053-1056.

Huang, D.-M., et al., "Highly efficient cellular labeling of mesoporous nanoparticles in human mesenchymal stem cells: implication for stem cell tracking", *The FASEB Journal*, 19, (2005), 2014-2016.

Huh, S., et al., "Organic Functionalization and Morphology Control of Mesoporous Silicas via a Co-Condensation Synthesis Method", *Chemistry of Materials*, 15(22), (2003), 4247-4256.

Huo, Q., et al., "A New Class of Silica Cross-Linked Micellar Core-Shell Nanoparticles", *Journal of the American Chemical Society*, 128(19), (2006), 6447-6453.

Huo, Q., et al., "Room Temperature Growth of Mesoporous Silica Fibers: A New High-Surface-Area Optical Waveguide", *Adv. Mater.*, 9(12), (1997), 974-978.

Huo, Q., et al., "Surfactant Control of Phases in the Synthesis of Mesoporous Silica-Based Materials", *Chemistry of Materials*, 8(5), (1996), 1147-1160.

Inagaki, S., et al., "An Ordered Mesoporous Organosilica Hybrid Material With a Crystal-Like Wall Structure", *Nature*, 416, (2002), 304-307.

Inagaki, S., et al., "Synthesis of Highly Ordered Mesoporous Materials, FSM-16, Derived from Kanemite", *Bull. Chem. Soc. Jpn.*, 69, (1996), 1449-1457.

Jeftinija, S. D., et al., "Neuroligand-Evoked Calcium-Dependent Release of Excitatory Amino Acids from Cultured Astrocytes", *Journal of Neurochemistry*, 66, (1996), 676-684.

Jeremic, A., et al., "ATP stimulates calcium-dependent glutamate release from cultured astrocytes", *Journal of Neurochemistry*, 77, (2001), 664-675.

Kageyama, K., et al., "Extrusion Polymerization: Catalyzed Synthesis of Crystalline Linear Polyethylene Nanofibers Within a Mesoporous Silica", *Science*, 285(5436), (1999), 2113-2115.

Karakassides, M. A., et al., "Synthesis and characterizeration of copper containing mesoporous silicas", *Journal of Materials Chemistry*, 10, (2000), 403-408.

Kataoka, Noriyasu, et al., "Air Stable, Sterically Hindered Ferrocenyl Dialkylphosphines for Palladium-Catalyzed C-C, C-N, and C-O Bond-Forming Cross-Couplings", *J. Org. Chem.*, 67, (2002), 5553-66.

Kawahara, et al., "Antibacterial effect of silver-zeolite on oral bacteria under anaerobic conditions", *Dental Materials*, (16(2000)), 452-455 pgs.

Kildiran, G., et al., "In-situ Alcoholysis of Soybean Oil", *JAOCS*, 73(2), (1996), 225-228.

Kisler, J. M., et al., "Separation of biological molecules using mesoporous molecular sieves", *Microporous and Mesoporous Materials*, 44-45, (2001), 769-774.

Kneuer, C., et al., "A Nonviral DNA Delivery System Based on Surface Modified Silica-Nanoparticles Can Efficiently Transfect Cells in Vitro", *Bioconjugate Chemistry*, 11(6), (2000), 926-932.

Kortesuo, P., et al., "In vitro evaluation of sol-gel processed spray dried silica gel microspheres as carrier in controlled drug delivery", *International Journal of Pharmaceuticals*, 200, (2000), 223-229.

Kresge, C. T., et al., "Ordered mesoporous molecular sieves synthesized by a liquid crystal template mechanism", *Nature*, 359(6397), (1992), 710-712.

Kruk, M., "Characterization of the Porous Structure of SBA-15", *Chemistry of Materials*, 12(7), (2000), 1961-1968.

Lai, Cheng-Yu, et al., "A Mesoporous Silica Nanosphere-Based Carrier System with Chemically Removable CdS Nanoparticle Caps for Stimuli-Responsive Controlled Release of Neurotransmitters and Drug Molecules", *Journal of the American Chemical Society*, 125, (2003), 4451-4459.

Langer, R., "Polymer-Controlled Drug Delivery Systems", *Accounts of Chemical Research*, 26(10), (2002), 537-542.

Lim, M. H., et al., "Synthesis of Ordered Microporous Silicates with Organosulfur Surface Groups and Their Applications as Solid Acid Catalysts", *Chemistry of Materials*, 10(2), (1998), 467-470.

Lim, M.. H., et al., "Comparative Studies of Grafting and Direct Synthesis of Inorganic-Organic Hybrid Mesoporous Materials", *Chemistry of Materials*, 11(11), (1999), 3285-3295.

Lim, M. H, et al., "Synthesis and Characterization of a Reactive Vinyl-Functionalized MCM-41: Probing the Internal Pore Structure by a Bromination Reaction", *Journal of the American Chemical Society*, 119(17), (Apr. 30, 1997), 4090-4091.

Lin, H.-P., et al., "Structural and Morphological Control of Cationic Surfactant-Templated Mesoporous Silica", *Accounts of Chemical Research*, 35(11), (2002), 927-935.

Lin, V. S.-Y., et al., "Molecular Recognition Inside of Multifunctionalized Mesoporous Silicas: Toward Selective Fluorescence Detection of Dopamine and Glucosamine", *Journal of the American Chemical Society*, 123(46), (2001), 11510-11511.

Lin, V. S, et al., "Oxidative Polymerization of 1,4-Diethynylbenzene into Highly Conjugated Poly(phenylene butadiynylene) within the Channels of Surface-Functionalized Mesoporous Silica & Alumina Materials", *Journal of the American Chemical Society*, 124(31), (2002), 9040-9041.

Lin, Y., et al., "Selective Sorption of Cesium Using Self-Assembled Monolayers on Mesoporous Supports", *Environmental Science & Technology*, 35(19), (2001), 3962-3966.

Littke, A. F, et al., "Palladium-catalyzed coupling reactions of aryl chlorides", *Angew. Chem. Int. Ed.*, 41, (2002), 4176-4211.

Liu, J., et al., "Molecular Assembly in Ordered Mesoporosity: A New Class of Highly Functional Nanoscale Materials", *The Journal of Physical Chemistry A*, 104(36), (2000), 8328-8339.

Luo, D., et al., "A self-assembled, modular DNA delivery system mediated by silica nanoparticles", *Journal of Controlled Release*, 95, (2004), 333-341.

Luo, D., et al., "Enhancement of transfection by physical concentration of DNA at the cell surface", *Nature Biotechnology*, 18, (2000), 893-895.

Ma, F., et al., "Biodiesel Fuel From Animal Fat. Ancillary Studies on Transesterification of Beef Tallow", *Industrial & Engineering Chemistry Research*, 37, (1998), 3768-3771.

MacLachlan, M. J., et al., "Writing on the Wall with a New Synthetic Quill", *Chem. Eur. J.*, 6(14), (2000), 2507-2511.

Mal, N. K., et al., "Photocontrolled reversible release of guest molecules from coumarin-modified mesoporous silica", *Nature*, 421, (2003), 350-353.

Margolese, D., et al., "Direct Syntheses of Ordered SBA-15 Mesoporous Silica Containing Sulfonic Acid Groups", *Chemistry of Materials*, 12(8), (2000), 2448-2459.

Marler, B., et al., "Influence of the sorbate type on the XRD peak intensities of loaded MCM-41", *Microporous Materials*, 6, (1996), 375-383.

Mbaraka, I. K., et al., "Organosulfonic Acid-Functionalized Mesoporous Silicas for the Esterification of Fatty Acid", *Journal of Catalysis*, 219, (2003), 329-336.

Melero, J. A., et al., "Direct Synthesis of Ordered SBA-15 Mesoporous Materials Containing Arenesulfonic Acid Groups", *Journal of Materials Chemistry*, 12 (2002), 1664-1670.

Miyaura, Norio, et al., "Palladium-Catalyzed Cross-Coupling Reactions of Organoboron Compounds", *Chem. Rev.*, 95, (1995), 2457-83.

Moller, K., et al., "Synthesis of Ordered Mesoporous Methacrylate Hybrid Systems: Hosts for Molecular Polymer Composites", *Chemistry of Materials*, 11(3), (1999), 665-673.

Moller, Karin, et al., "Inclusion Chemistry in Periodic Mesoporous Hosts", *Chemistry of Materials*, 10(10), (Oct. 1998), 2950-2963.

Muñoz, B., et al., "MCM-41 Organic Modification as Drug Delivery Rate Regulator", *Chemistry of Materials*, 15(2), (2003), 500-503.

Neary, J. T., et al., "ATP-evoked calcium signal stimulates protein phosphorylation/dephosphorylation in astrocytes", *Brain Research*, 566, (1991), 89-94.

Newman, E. A., et al., "Calcium Waves in Retinal Glial Cells", *Science*, 275, (1997), 844-847.

Niemeyer, C., "Nanoparticles, proteins, and nucleic acids : biotechnology meets materials science", *Angew Chem. Int. Ed*, OARN, (2001), 4129-4158 pgs.

Ogoshi, T., et al., "Soap and Related Products: Palm and Lauric Oil", *JAOCS*, 62(2), (1985), 331-335.

Ozin, G. A., "Panoscopic materials: synthesis over 'all' length scales", *Chem. Comm.*, (2000), 419-432.

Price, P. M., et al., "Modified silicas for clean technology", *J. Chem. Soc., Dalton Trans.*, (2000), 101-110.

Quintana, A., et al., "Design and Function of a Denrimer-Based Therapeutic Nanodevice Targeted to Tumor Cells Through the Folate Receptor", *Pharmaceutical Research*, 19(9), (2002), 1310-1316.

Radin, S., et al., "Silica sol-gel for the controlled release of antiboitics. I. Synthesis, characterization, and in vitro release", *J. Biomed. Mater. Res.*, 57, (2001), 313-320.

Radu, D. R., et al., "Fine-Tuning the Degree of Organic Functionalization of Mesoporous Silica Nanosphere Materials via an Interfacially Designed Co-Condensation Method", *Chem. Commun.*, (2005), 1264-1266.

Radu, D. R, et al., "A Polyamidoamine Dendrimer-Capped Mesoporous Silica Nanosphere-Based Gene Transfection Reagent", *J Am Chem Soc*, 126(41), (2004), 14 pgs.

Ramila, A., et al., "Mesoporous MCM-41 as Drug Host System", *Journal of Sol-Gel Science and Technology*, 26, (2003), 1199-1202.

Ryoo, R., et al., "Disordered Molecular Sieve with Branched Mesoporous Channel Network", *The Journal of Physical Chemistry*, 100(45), 1996, 17718-17721.

Sadasivan, S., et al., "Synthesis and shape modification of organo-functionalised silica nanoparticles with ordered mesostructured interiors", *Journal of Materials Chemistry*, 13, (2003), 1023-1029.

Sanford, J. C., et al., "Optimizing the Biolistic Process for Different Biological Applications", *Methods in Enzymology*, 217, (1993), 483-509.

Sayari, A., "Catalysis by Crystalline Mesoporous Molecular Sieves", *Chemistry of Materials*, 8(8), (1996), 1840-1852.

Sayari, A., et al., "Periodic Mesoporous Silica-Based Organic-Inorganic Nanocomposite Materials", *Chemistry of Materials*, 13(10), (2001), 3151-3168.

Schumacher, K., et al., "The Synthesis of Spherical Mesoporous Molecular Sieves MCM-48 with Heteroatoms Incorporated into the Silica Framework", *Adv. Mater.*, 11(14), (1999), 1194-1198.

Sheen, S., et al., "An in vitro evaluation of the availabilitiy of cetylpyridinium chloride and chlorhexidine in some commercially available mouthrinse products", *British Dental Journal*, (2003), 194(4), 207-210.

Shukla, R., et al., "Biocompatibility of Gold Nanoparticles and Their Endocytotic Fate Inside the Cellular Compartment: A Microscopic Overview", *Langmuir*, 21, (2005), 10644-10654.

Shyu, S.-G., et al., "Immobilization of Rh(PPh$_3$)$_3$Cl on phosphinated MCM-41 for catalytic hydrogenation of olefins", *Chem. Commun.*, 1999, 2337-2338.

Sing, K., et al., "Reporting Physisorption Data for Gas Solid Systems With Special Reference to the Determination of Surface-Area and Porosity", *Pure Appl. Chem.*, 57, (1985), 603-619.

Slowing, I., et al., "Effect of Surface Functionalization of MCM-41-Type Mesoporous Silica Nanoparticles on the Endocytosis by Human Cancer Cells", *J. Am. Chem. Soc.*, 128 (46), (Nov. 2, 2006), 14792-14793.

Slowing, I. I, et al., "Mesoporous Silica Nanoparticles for Intracellular Delivery of Membrane-Impermeable Proteins", *J. Am. Chem. Soc.*, 129(28), (2007), 8845-8849.

Slowing, I. I., et al., "Supporting Information Mesoporous Silica Nanoparticles for Intracellular Delivery of Membrane Impermeable Proteins", *J. Am. Chem. Soc.*, (2007), 1-9.

Soler-Illia, G. J., et al., "Chemical Strategies to Design Textured Materials: from Microporous and Mesoporous Oxides to Nanonetworks and Heirarchical Structures", *Chem. Rev.*, 102, (2002), 4093-4138.

Stein, A., "Advances in Microporous and Mesoporous Solids—Highlights of Recent Progress", *Advanced Materials*, 15(10), (2003), 763-775.

Stein, A., et al., "Hybrid Inorganic-Organic Mesoporous Silicates-Nanoscopic Reactors Coming of Age", *Advanced Materials*, 12(19), (2000), 1403-1419.

Stöber, W., et al., "Controlled Growth of Monodisperse Silica Spheres in the Micron Size Range", *Journal of Colloid and Interface Science*, 26, (1968), 62-69.

Su, F., et al., "Ordered mesoporous carbon particles covered with carbon naotubes", *Carbon*, 44, (2006), 801-803.

Subramanian, S., et al., "Quantitative analysis of transient gene expression in mammalian cells using the green fluorescent protein", *Journal of Biotechnology*, 49, (1996), 137-151.

Suppes, G. J., et al., "Calcium Carbonate Catalyzed Alcoholysis of Fats and Oils", *JAOCS*, 78(2), (2001), 139-145.

Suzuki, K., et al., "Synthesis of Silica Nanoparticles Having a Well-Ordered Mesostructure Using a Double Surfactant Systems", *J. Am. Chem. Soc.*, 126, (2004), 462-463.

Takahashi, H., et al., "Immobilized enzymes in ordered mesoporous silica materials and improvement of their stability and catalytic activity in an organic solvent", *Microporous and Mesoporous Materials*, 44-45, (2001), 755-762.

Tanev, P. T., "A Neutral Templating Route to Mesoporous Molecular Sieves", *Science*, 267(5199), (1995), 865-867.

Torney, F., et al., "Mesoporous silica nanoparticles deliver DNA and chemicals into plants", *Nature Nanotechnology 2*, (2007), 295-300.

Torney, F., et al., "Mesoporous silica nanoparticles deliver DNA and chemicals into plants (supplementary methods)", (2007), 7 pgs.

Uhrich, K. E., et al., "Polymeric Systems for Controlled Drug Release", *Chemical Reviews*, 99(11), (1999), 3181-3198.

Urgaonkar, S., et al., "Application of a New Bicyclic Triaminophosphine Ligand in Pd-Catalyzed Buchwald-Hartwig Amination Reactions of Aryl Chlorides, Bromides, and Iodides", *J. Org. Chem.*, 68, (2003), 8416-8423.

Urgaonkar, S., et al., "Pd/P(i-BuNCH$_2$CH$_2$)$_3$N: an efficient catalyst for Suzuki cross-coupling of aryl bromides and chlorides with arylboronic acids", *Tetrahedron Letters*, 43, (2002), 8921-8924.

Urgaonkar, S., "Synthesis of N-aryl-aza-crown ethers via Pd-catalyzed amination reactions of aryl chlorides with aza-crown ethers", *Tetrahedron*, 60, (2004), 11837-11842.

Vallet, R., et al., "A New Property of MCM-41 : Drug Delivery System", *Chem. Mater*, 13, (2001), 308-311.

Van Rhijn, W. M., et al., "Sulfonic Acid Functionalised Ordered Mesoporous Materials as Catalysts for Condensation and Esterification Reactions", *Chemical Communications*, (3), (1998), 317-318.

Verkade, J., "P(RNCH₂CH₂)₃N: Very Strong Non-Ionic Bases Useful in Organic Synthesis", *Topics in Current Chemistry*, 223, (2003), 3-40.

Wang, S., et al., "Incorporation of CdS nanoparticles inside ordered mesoporous silica SBA-1 via ion exchange", *Advanced Materials*, 14(18), (2002), 1311-1313.

Wang, Z., et al., "Direct Observation of Calcium-Independent Intercellular ATP Signaling in Astrocytes", *Analytical Chemistry*, 72(9), (2000), 2001-2007.

Wildes, S. G., "TA 91-1997—Market Opportunity Summary—Soy-Based Solvents", (United Soybean Board (USB)), (1997), 2 pgs.

Winkler, H., et al., "Quantum-Confined Gallium Nitride in MCM-41", *Advanced Materials*, 11(17), (1999), 1444-1448.

Wirnsberger, G., et al., "pH Sensing with mesoporous thin films", *Chem. Comm., Issue 1*, (2001), 119-120.

Yanagisawa, T., et al., "The Preparation of Alkyltrimethylammonium-Kanemite Complexes and Their Conversion to Microporous Materials", *Bull. Chem. Soc. Jpn.*, 63(4), (1990), 988-992.

Yang, Q., et al., "Sulfuric Acid-Functionalized Mesoporous Benzene-Silica with a Molecular-Scale Periodicity in the Walls", *Journal of the American Chemical Society*, 124, (2002), 9694-9695.

Ying, J. Y., et al., "Synthesis and Applications of Supramolecular-Templated Mesoporous Materials", *Angewandte Chemie International Edition*, 38, (1999), 56-77.

Yiu, H. H. P., et al., "Enzyme immobilisation using siliceous mesoporous molecular sieves", *Microporous and Mesoporous Materials*, 44-45, (2001), 763-768.

Yoshitake, H., et al., "Adsorption Behavior of Arsenate at Transition Metal Cations Captured by Amino-Functionalized Mesoporous Silicas", *Chemistry of Materials*, 15(8), (2003), 1713-1721.

Yoshitake, H., et al., "Oxyanion Adsorptions by Mono-, Di-, and Triamino-Functionalized MCM-48", *Bull. Chem. Soc. Jpn.*, 76, (2003), 847-852.

Zhang, W.-H., et al., "Preparation and Characterization of ZnO Clusters inside Mesoporous Silica", *Chemistry of Materials*, 12(5), (2000), 1408-1413.

Zhang, W.-H., et al., "Synthesis and Characterization of Nanosized ZnS Confined in Ordered Mesoporous Silica", *Chemistry of Materials*, 13(2), (2001), 648-654.

Zhao, D., et al., "Morphological Control of Highly Ordered Mesoporous Silica SBA-15", *Chemistry of Materials*, 12(2), 2000, 275-279.

Zhao, D., et al., "Triblock Copolymer Syntheses of Mesoporous Silica With Periodic 50 to 300 Angstrom Pores", *Science*, 279, (1998), 548-552.

Zhu, Y., et al., "Developmental expression of metabotropic $P2Y_1$ and $P2Y_2$ receptors in freshly isolated astrocytes from rat hippocampus", *Journal of Neurochemistry*, 77, (2001), 530-541.

Zub, Y. L., et al., "Polyfunctionalised surfactant-templated adsorbents with high specific surface areas", *Mendeleev Commun.*, 11(6), (2001), 208-210.

Zuo, J., et al., "An estrogen receptor-based transactivator XVE mediates highly inducible gene expression in transgenic plants", *The Plant Journal*, 24(2), (2000), 265-273.

"U.S. Appl. No. 11/788,147 Final Office Action mailed Nov. 19, 2010", 2.

"U.S. Appl. No. 11/788,147, Advisory Action mailed Feb. 15, 2011", 3 pgs.

"U.S. Appl. No. 11/788,147, Final Office Action mailed Nov. 19, 2010", 9 pgs.

"U.S. Appl. No. 11/788,147, Response filed Jan. 11, 2011 to Final Office Action mailed Nov. 19, 2010", 9 pgs.

"U.S. Appl. No. 11/788,147, Response to Final Office Action mailed Nov. 19, 2010 and Advisory Action mailed Feb. 15, 2011", 10 pgs.

"U.S. Appl. No. 12/124,747 Non-Final Office Action mailed Oct. 12, 2010", 16 pgs.

Yiu, et al., "J. Mater. Chem, 2005, 15", (Jul. 11, 2005), 3690-3700.

"U.S. Appl. No. 11/788,147, Non-Final Office Action mailed Jun. 21, 2010", 12 Pgs.

"U.S. Appl. No. 11/788,147, Preliminary Amendment filed Apr. 28, 2008", 4 pgs.

"U.S. Appl. No. 11/788,147, Response filed Feb. 24, 2010 to Restriction Requirement mailed Jan. 29, 2010", 7 pgs.

"U.S. Appl. No. 11/788,147, Response filed Sep. 14, 2010 to Non Final Office Action mailed Jun. 21, 2010", 8 pgs.

"U.S. Appl. No. 11/788,147, Restriction Requirement mailed Jan. 29, 2010", 9 Pgs.

"U.S. Appl. No. 12/124,747, Response to Restriction Requirement", 10 pgs., Aug. 26, 2010.

"U.S. Appl. No. 12/124,747 Restriction Requirement mailed Jul. 27, 2010", 8 pgs.

Christou, Paul, et al., "Stable Transformation of Soybean Callus by DNA-Coated Gold Particles", Plant Physiol., 87(3), (Jul. 1988), 671-674.

Xu, H., et al., "Room-temperature preparation and characterization of poly (ethylene glycol)-coated silica nanoparticles for biomedical applications", J Biomed Mater Res A., 66(4), (Sep. 15, 2003), 870-9.

* cited by examiner

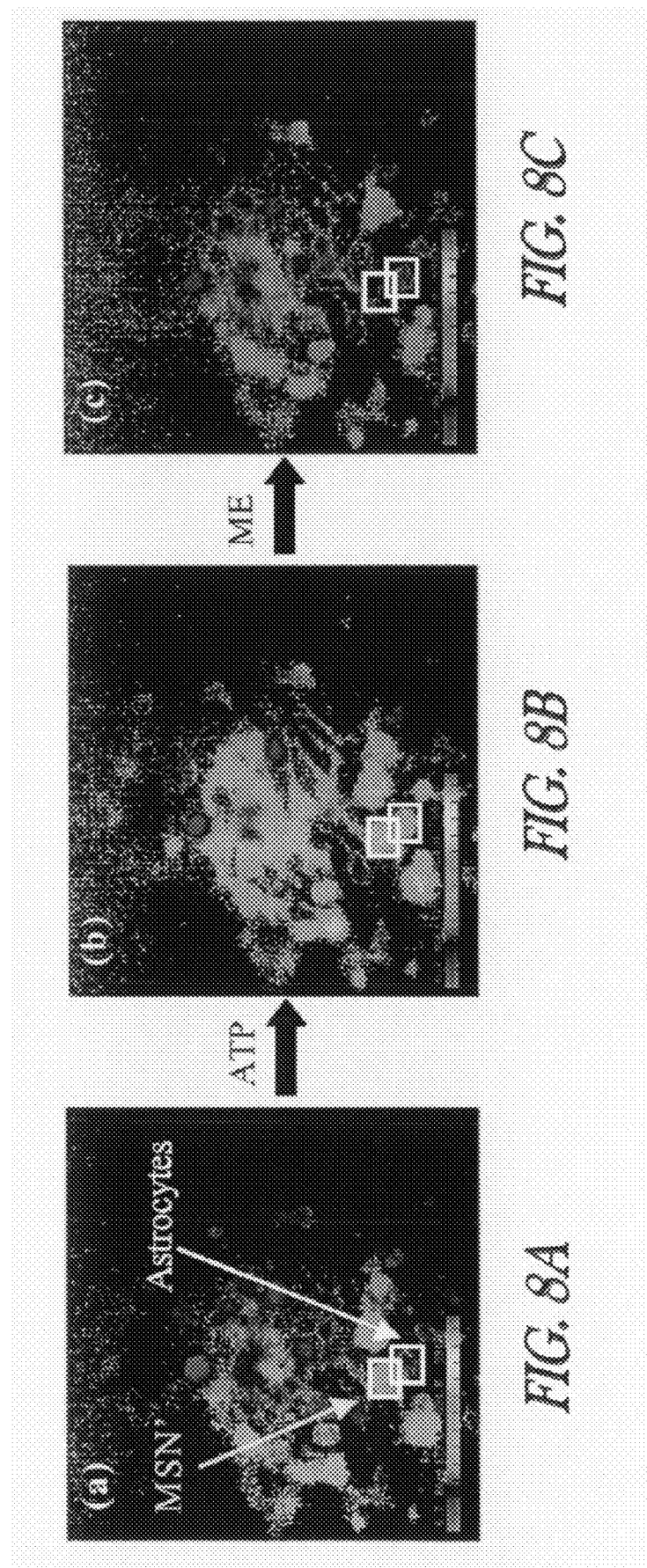

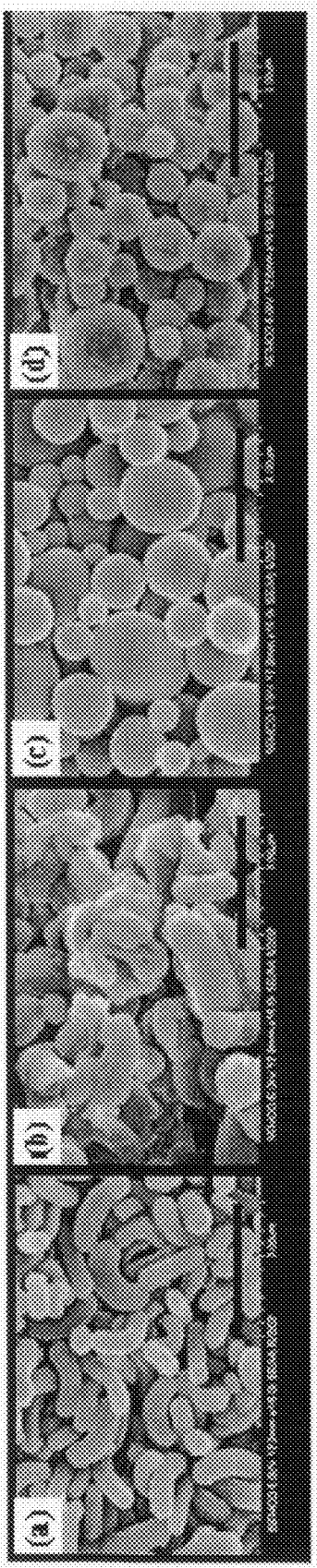
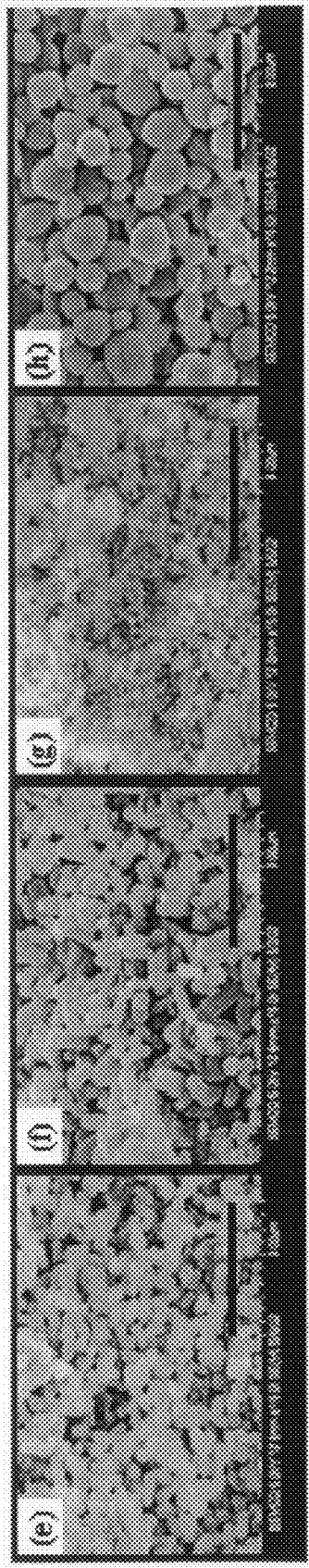
FIG. 12A  FIG. 12B  FIG. 12C  FIG. 12D
FIG. 12E  FIG. 12F  FIG. 12G  FIG. 12H

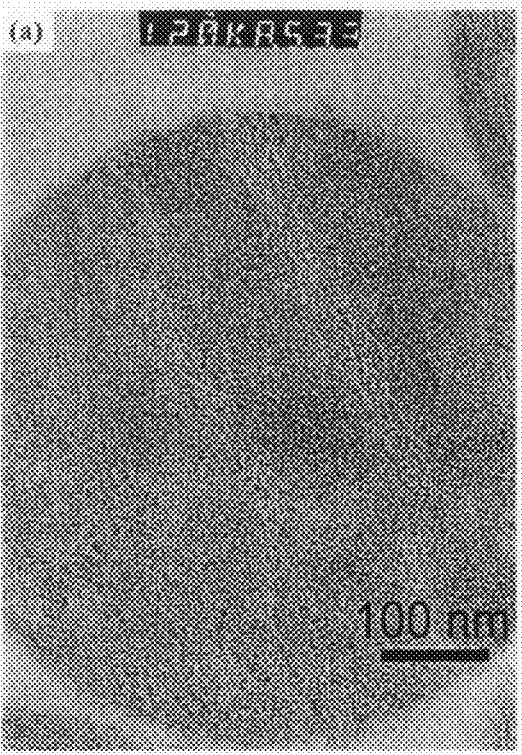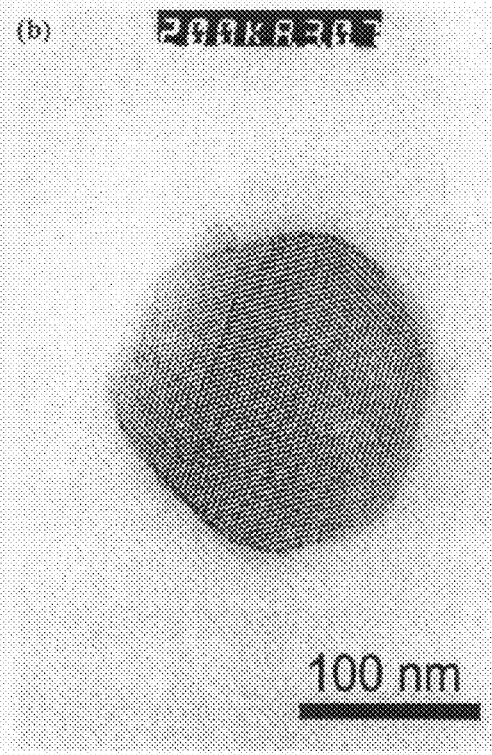
FIG. 15A　　　FIG. 15B
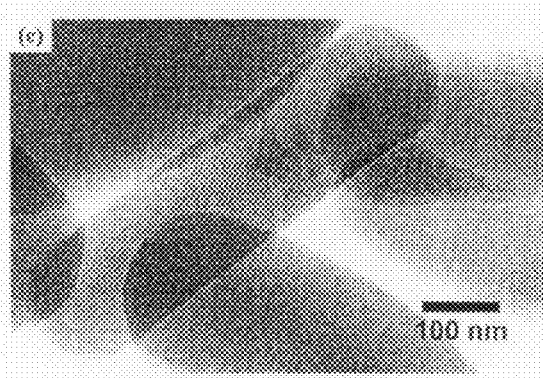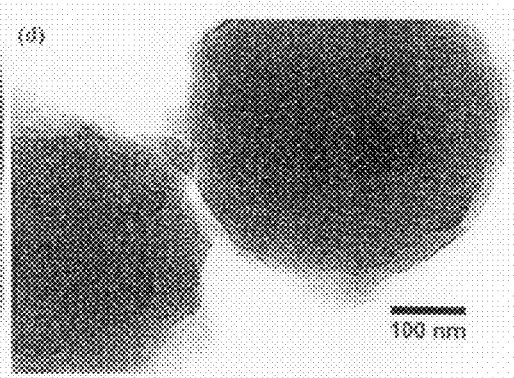
FIG. 15C　　　FIG. 15D

CAPPED MESOPOROUS SILICATES

RELATED APPLICATIONS

This application is a continuation of U.S. patent application Ser. No. 10/830,479, filed Apr. 22, 2004, now U.S. Pat. No. 7,563,451 which claims priority under 35 U.S.C. §119(e) to U.S. Provisional Patent Application No. 60/489,043, filed Jul. 22, 2003, which applications are incorporated herein by reference in their entirety.

GOVERNMENT FUNDING

This invention was made with Government support under NSF Contract No. CHE-0239570. The United States Government has certain rights in this invention.

BACKGROUND OF THE INVENTION

The development of surfactant-templated mesostructures represents a major advance in materials chemistry. Several attractive features, such as large surface areas, tunable pore sizes and volumes, and well-defined surface properties make mesostructured materials ideal for hosting molecules of various sizes, shapes, and functionalities. For example see Stein, A., et al., *Adv. Mater.* 2000, 12, 1403-1419; and Sayari, A., et al., *Chem. Mater.* 2001, 13, 3151-3168. Hexagonally ordered mesoporous silicate structures were discovered by Mobil Corp. (M41 S materials like MCM-41) and by Kuroda, et al., (FSM-16 materials). See, e.g., Kresge, C. T., et al., *Nature* 359, 710 (1992) and Yanagisawa, T. et al., *Bull. Chem. Soc. Jpn.* 63, 988 (1990). Structures of uniform pore sizes can now be formed throughout the mesopore size range, which encompasses 2-50 nm by IUPAC definition. See, Sing, et al., *Pure Appl. Chem.* 57, 603 (1985).

In the field of drug delivery, many site-selective deliveries, e.g., deliveries of highly toxic antitumor drugs, such as Taxol, require "zero release" before reaching the targeted cells or tissues. Unfortunately, the release of compounds from many drug delivery systems takes place immediately upon dispersion of the drug/carrier composites in water. For example, see Radin, S., et al., *J. Biomed. Mater. Res.* 2001, 57, 313-320; Aughenbaugh, W., et al., *J. Biomed. Mater. Res.* 2001, 57, 321-326; and Kortesuo, P., et al., *Int. J. Pharm.* 2000, 200, 223-229. The release mechanism of other systems, such as biodegradable polymer-based drug delivery systems, also relies on the hydrolysis-induced erosion of the carrier structure. See Uhrich, K. E., et al., *Chem. Rev.* 1999, 99, 3181-3198; and Langer, R. *Acc. Chem. Res.* 1993, 26, 537-542. Additionally, many polymeric based release systems require organic solvents for drug loading, which can trigger undesirable modifications of the structure or function of the encapsulated molecules, such as protein denaturation or aggregation. See Li, Y.; Kissel, T., *J. Controlled Release* 1993, 27, 247-257.

The development of mesoporous silica-based carrier systems for controlled-release delivery of drugs, biocides, genes, or even proteins in vitro or in vivo is of keen interest. See Vallet-Regi, M., et al., *Chem. Mater.* 2001, 13, 308-311; Munoz, B., et al., *Chem. Mater.* 2003, 15, 500-503; Ramila, A., et al., *J. Sol.-Gel Sci. Technol* 2003, 26, 1199-1202; Diaz, J. F., et al., *J. Mol. Catal. B: Enzym.* 1996, 2, 115-126; Han, Y.-J., et al., *J. Am. Chem. Soc.* 1999, 121, 9897-9898; Kisler, J. M., et al., *Microporous Mesoporous Mater.* 2001, 44-45, 769-774; Yiu, H. H. P., et al., *Microporous Mesoporous Mater.* 2001, 44-45, 763-768; and Takahashi, H., et al., *Microporous Mesoporous Mater.* 2001, 44-45, 755-762. Despite this current interest, there remains a need for novel carrier systems that can be used for the controlled-release delivery of drugs, biocides, genes, or proteins in vitro or in vivo.

SUMMARY OF THE INVENTION

A novel mesoporous silica-based delivery system is provided which provides the controlled release of one or more agents from pores within its matrix. This delivery system is typically stimuli-responsive and chemically inert to the matrix-entrapped molecules. The pores of the mesoporous silica matrix act as reservoirs that can be loaded with a variety of molecules, e.g., bioactive agents such as conventional therapeutic agents ("drugs") as well as amino acids, oligonucleotides, and/or polypeptides, such as hormones, enzymes, cytokines and the like. The openings of the loaded mesopores are then reversibly or irreversibly capped (e.g. with semiconductor nanoparticles, biodegradable dendritic polymers (dendrimers), or proteins) so as to encapsulate the molecules within the pores of the silica matrix. The loaded and capped delivery systems allow for the site specific controlled release of the loaded material from the pores of the mesoporous matrix. Thus, the articles of the invention can be used for targeted drug delivery, antisense therapy, immunotherapy, gene therapy, and similar applications.

The loaded and capped particles are also generally useful for the controlled release of encapsulated agents in a host of other fields. For example, they can be used in agricultural applications (e.g. for the controlled release of pesticides or fertilizers), in personal health care applications (e.g. for the controlled release of cosmetics and nutrients), in printing and manufacturing applications (e.g. for the controlled release of inks and dyes) and in environmental applications (e.g. to remove unwanted materials from the environment, as from a liquid or gas stream, or to deliver material into an environment in a controlled or time delayed manner).

Accordingly the invention provides an article, comprising, a mesoporous silicate body having a multiplicity of pores; and one or more caps obstructing one or more of the pores. Preferably one or more deliverable agents is contained within one or more of the capped pores.

The invention also provides a pharmaceutical composition comprising an article of the invention that comprises a bioactive agent in combination with a pharmaceutically acceptable diluent or carrier, as well as methods for its use in site-specific or controlled delivery of the bioactive agent(s).

The invention also provides a composition comprising an article of the invention that comprises one or more agriculturally active agents (e.g. a pesticide, or a fertilizer) in combination with a agronomically acceptable diluent or carrier, as well as methods for its use in site-specific or controlled delivery of the agriculturally active agent(s).

The invention also provides an article of the invention that comprises a bioactive agent (e.g. a therapeutic agent or a diagnostic agent) for use in medical therapy or diagnosis.

The invention also provides novel processes and intermediates disclosed herein that are useful for preparing mesoporous silicates and articles of the invention.

The capped mesoporous silica particles of the invention can be used as controlled-release carriers for the delivery of the material(s) enclosed in the pores. Given that the loading and release mechanism is based on the capping and uncapping of the openings of the mesopores, no chemical modification of the loaded molecules is needed to bind them to the pores, and no specific reaction is required to release them, apart from application of conditions required to remove the caps. In addition, the biocompatibilty and stability of the mesoporous silica particles of the invention allow the loaded particles to be used to investigate various intra- and intercellular chemical/neurochemical interactions in vitro. The mesoporous silica particles of the invention can further comprise targeting agent on the external surface thereof, or can be incorporated into site-selective, controlled-release delivery devices such as interactive sensory nanodevices.

BRIEF DESCRIPTION OF THE FIGURES

FIG. 12 FE-SEM Images of AP-MP (a), AAP-MP (b), AEP-MP (c), UDP-MP (d), ICP-MP (e), CP-MP (f), AL-MP (g), and pure MCM-41 silica (h) synthesized via our condensation reaction condition without adding any organic functional group. All images are presented using the same scale, with the scale bar=3 μm.

FIG. 15 TEM micrographs of AEP-MP (a), CP-MP (b, c), and UDP-MP (d) materials. Images (a) and (b) represent ultramicrotomed samples (scale bar=100 nm).

FIG. 18 TEM images of ultramicrotomed AEP-MP's with 1.28 mol % (a) and 6.43 mol % and (b) AEPTMS prepared in Example 5 (scale bar=100 nm).

DETAILED DESCRIPTION

Figure 1:
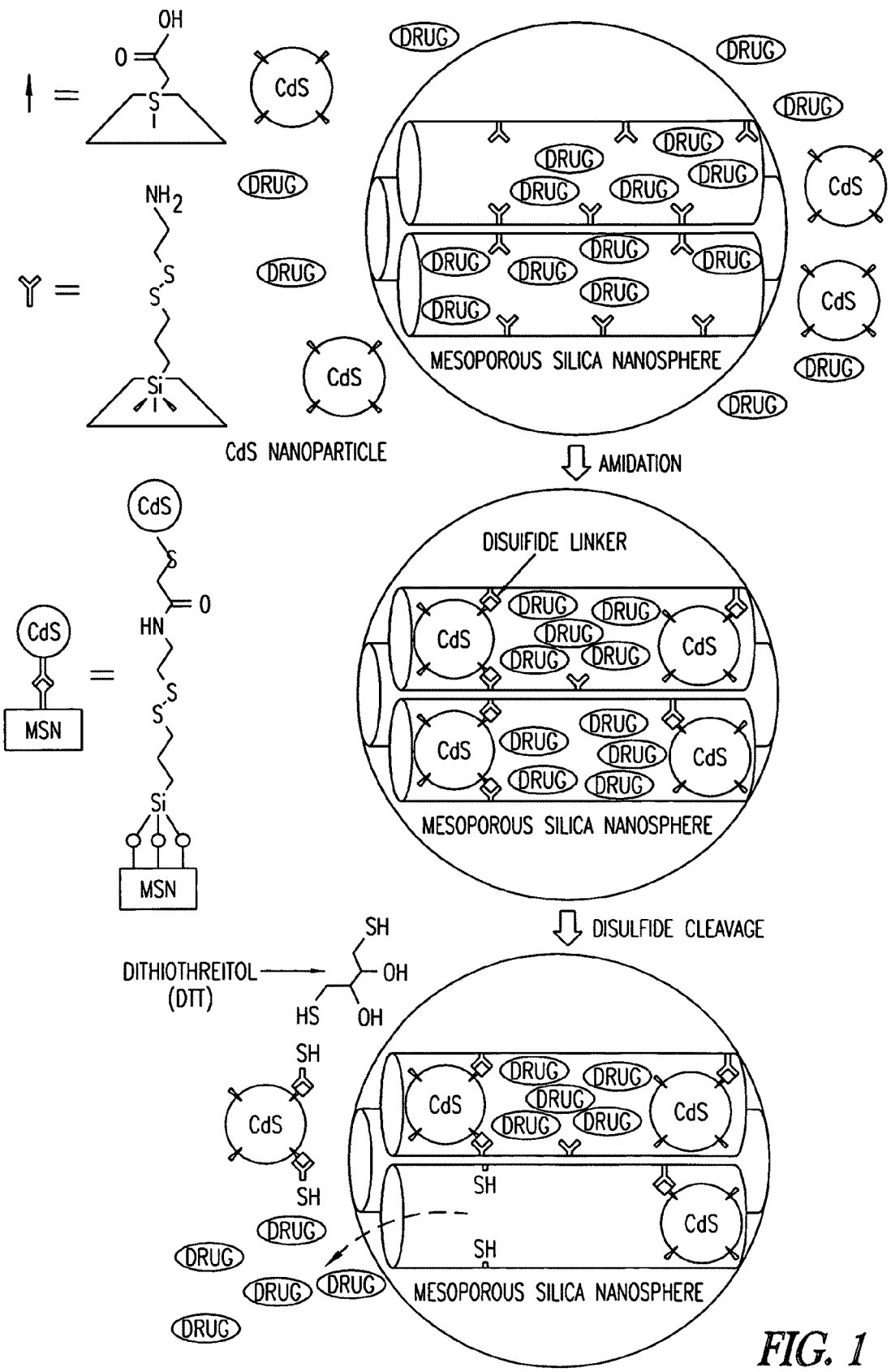
FIG. 1 is a schematic representation of a CdS nanoparticle-capped MSN-based delivery system.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide). Other suitable amino and carboxy protecting groups are known to those skilled in the art (See for example, T. W. Greene, *Protecting Groups In Organic Synthesis*; Wiley: New York, 1981, and references cited therein).

The term Asaccharide@ includes monosaccharides, and polysaccharides (e.g. disaccharides, trisaccharides, etc.) The term includes glucose, sucrose fructose and ribose, as well as deoxy sugars such as deoxyribose and the like. Saccharide derivatives can conveniently be prepared as described in International Patent Applications Publication Numbers WO 96/34005 and 97/03995.

The term "polypeptide" describes a sequence of 2 to 250 amino acids (e.g. as defined hereinabove) or peptidyl residues. The sequence may be linear or cyclic. For example, a cyclic peptide can be prepared or may result from the formation of disulfide bridges between two cysteine residues in a sequence. A polypeptide can be linked to the remainder of a compound of formula I through the carboxy terminus, the amino terminus, or through any other convenient point of attachment, such as, for example, through the sulfur of a cysteine. In one embodiment of the invention a polypeptide comprises about 3 to about 100 amino acids. In another embodiment a polypeptide comprises about 5 to about 25 amino acids Peptide and polypeptide derivatives can be prepared as disclosed in U.S. Pat. Nos. 4,612,302; 4,853,371; and 4,684,620, or as described in the Examples hereinbelow. Polypeptide sequences specifically recited herein are written with the amino terminus on the left and the carboxy terminus on the right.

A peptide is a polyamino acid sequence comprising more than 250 amino acid residues.

The term "nucleic acid", "polynucleic acid" or "polynucleic acid segment" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260: 2605 (1985); Rossolini et al., Mol. Cell. Probes, 8:91 (1994)). An "oligonucleotide" typically includes 30 or fewer nucleotides.

Mesoporous Silicates

Mesoporous silicates typically have a particle size of about 50 nm to about 1 µm. In one embodiment, the mesoporous silicates have a particle size of at least about 100 nm, or preferably at least about 200 nm. In another embodiment, the mesoporous silicates have a particle size of less than about 750 nm. As conventionally prepared, they are spherical, but they have also been prepared under conditions that yield other shapes such as rods. The articles of the invention can include mesoporous silicates of any shape, provided the pore structure is suitable for receiving the encapsulated agent.

The mesoporous silicate pores typically have a diameter of from about 1-100 nm. In one embodiment of the invention, the pores have a diameter of at least about 2 nm. In other embodiments, the pores have diameters of greater than about 5 nm, or greater than about 10 nm. Typically, the pores have a diameter of less than about 75 nm or less than about 50 nm.

The mesoporous silicates can be prepared from surfactant micelles of $C_{10}$-$C_{16}$ alkyl(trialkyl)ammonium salts in water, followed by introduction into the solution of an alkyl orthosilicate, such as tetraethylorthosilicate (TEOS), and one or more functionalized silanes, such as one or more mercaptoalkyl-, chloroalkyl-, aminoalkyl-, carboxyalkyl-, sulfonylalkyl-, arylalkyl-, alkynyl-, or alkenyl-silanes, wherein the ($C_2$-$C_{10}$)alkyl chain is optionally interrupted by —S—S—, amido (—C(=O)NR—), —O—, ester (—C(=O)O—), and the like. The aqueous mixture is stirred at moderate temperatures until the silicate precipitates, and it is collected and dried. The surfactant "template" is then removed from the pores of the ordered silicate matrix, for example, by refluxing the silicate in aqueous-alcoholic HCl. The remaining solvent can be removed from the pores of the silicate by placing it under high vacuum. The functional groups incorporated on the surface of the pores can be quantified and used as linker moieties to bind to the caps, or they can be further modified by attaching terminally-functionalized organic linker moieties that can be reacted with functional groups on the caps. The polarity of the interior of the pores can also be adjusted by adding other functionalized silanes to the reaction mixture, including ones comprising non-polar inert groups such as aryl, perfluoroalkyl, alkyl, arylakyl and the like. The exterior of the silicate matrix can be functionalized by grafting organic moieties comprising functional groups thereto. These groups can in turn be employed to link the particles to targeting or labeling moieties.

Functionalized Caps

In an article of the invention, the cap serves to slow or to prevent the release of an encapsulated agent from the pores of the mesoporous silicate. Thus, as used herein, "obstructing" includes partially or fully blocking the opening of a pore such that the release of an encapsulated agent is slowed or prevented. The cap can be covalently bonded to the mesoporous silicate or it can be associated thereto through ionic, hydrogen bonding, or other interactions. The cap can be positioned in the opening of a pore or it can be located within the pore itself (e.g. bonded or linked to the interior surface of the pore). The cap can be a discrete body, such as a particle of an inorganic salt, protein, or a polymeric nanosphere, or it can be in the form of a polymer coating that partially or completely covers the mesoporous silicate particle.

The cap can comprise a variety of materials, which can be selected based on the intended application for the loaded particles and on the size and reactivity of the mesoporous silicate material. For example, the cap can comprise an inorganic particle or crystal, an organic polymer, such as a dendrimer or a polypeptide, or a biopolymer, such a protein, an oligonucleotide, or an oligosaccharide.

One particularly useful cap is a crystalline cadmium sulfide particle described in the Examples hereinbelow. Other inorganic crystals polymers or particles can be selected based on the size of the pores in the mesoporous silicate, the size of the metal containing particle, the reactive sites available for attaching the mesoporous silicate to the particle, and based on the chemical and physical environment where the capped particle will be delivered. Another cap that is particularly useful for facilitating the delivery of an article to the interior of a cell is a biodegradable poly(amidoamine) dendrimer.

The caps can be associated (e.g. bonded, complexed, or attracted) directly with the surface of the mesoporous silicate body or the surface of the pores, or the caps can be associated with a linker group that is attached to the surface of the mesoporous silicate body or the surface of the pores. Linking groups can be selected based on their ability to bond to or be incorporated with the mesoporous silicate and on their ability to associate with a given cap. The length of the linking group is not critical, provided it allows the associated cap to obstruct the pores of the mesoporous silicate. For example, the linking group can typically be from about 5 Angstroms to about 500 Angstroms in length. For some applications, the linking group can preferably be from about 25 Angstroms to about 250 Angstroms in length. In one embodiment of the invention, the linking group comprises a 2-(propyldisulfanyl)ethylamine. In another embodiment of the invention the linking group is a group of the formula X—$CH_2CH_2CH_2SSCH_2CH_2NHC(=O)CH_2$—Y—, wherein X is a silicon atom of the mesoporous silicate and Y is an atom of the cap (e.g. a sulfur atom).

In one embodiment of the invention, the linking group comprises labile group that can selectively react with a releasing agent to release the cap from the mesoporous silicate following delivery to a target site. The releasing agent can be an agent that is naturally present at the target site, or it can be an agent that is introduced at the target site when release of the encapsulated material is desired. For example, the labile group can be a reactive disulfide bond, a pH sensitive bond, a temperature labile bond, or a photochemically active group and the releasing agent can be a disulfide reducing agent, acid/base (local pH changes), temperature variation, or light of a preselected wavelength.

Encapsulated Agents

The articles of the invention are generally useful for delivering materials (i.e. encapsulated agents) in a controlled manner. The nature of the encapsulated material is not critical, so long as it can be introduced into the pores in an effective amount and released from the pores under pre-selected conditions. Thus, encapsulated agents include bioactive agents, inks, dyes, cosmetics, and the like.

The term bioactive agents includes pharmaceutical agents, diagnostic agents, genes, nutrients (vitamins, etc.), and pesticidal agent (e.g. insecticides, herbicides, and rodentacides). For example, the term includes conventional chemotherapeutic agents useful to treat cancer (see PCT US/00/16052), chelated radionuclides, immunosuppressive drugs, antiinflammatory agents, antibacterial agents, antifungal agents, antiviral agents (see U.S. Pat. No. 4,950,758) analgesic agents (see U.S. Pat. Nos. 5,298,622 and 5,268,490), polypeptides; hormones, hormonal messengers, and cytokines (e.g. insulin, interleukins, interferons, human growth hormone, PTK, TPMT, TGF-β, EPO, TNF, NK-β, and prostaglandins, and the like), imaging agents, contrast agents, enzymes for enzyme replacement therapy (see, U.S. Pat. Nos. 6,106,834 and 6,210,666), antibodies (see U.S. Pat. Nos. 6,106,834 and 6,210,666), antibodies (see U.S. Pat. Nos. 5,034,222 and 6,106,834); and RNA or DNA molecules of any suitable length (see PCT US/00/16052, PCT WO96/30031, and U.S. Pat. Nos. 5,591,625, 6,387,369, 5,190,931, 5,208,149, and 5,272,065).

The capped particles of the invention can be used to transform plant cells, delivering "foreign DNA" as disclosed in U.S. Pat. Nos. 6,329,574 and 5,384,253. The capped particles can also be used to transform mammalian cells (e.g. neural cells).

Loading Bioactive Molecules

The encapsulated materials can be free in the mesopores of the silicate body or they can be associated (e.g. bonded or attracted) with the interior surface of the pores. When they are free in the pores, they can typically be loaded by contacting an uncapped "empty" mesoporous silicate in a solution of the agent to be encapsulated. When the encapsulated agents are associated with the interior surface of the pores, they can typically be loaded by allowing the agent to react with groups on the interior surface of the pores under conditions suitable to allow the agent to associate.

Delivery of Loaded Particles to Target Site

The loaded articles of the invention can be delivered to the target site by any suitable means, which can be selected based on the nature of the target site and the encapsulated agent. For example, for agricultural field-use applications, the loaded particles can be spread on a target field using conventional field spreaders or using an airplane. For cellular transformations in vitro microprojectile bombardment can be used to propel the particles through the cell walls of cultured plant cells, or electroporation can be used to introduce the particles into protoplasts.

For uses in vivo the articles can be administered orally, topically or by injection using conventional means. For gene therapy applications or for other applications where it is desirable to deliver the articles into cells, they can be delivered by direct injection, other placement techniques, or by allowing the particles to be internalized into cells via endocytosis. The articles can be targeted to a specific location in an animal (e.g. to a specific organ or to a tumor), using targeting agents (e.g. an antibody or antibody fragment ("binding protein") specific for receptor site on target cell, tissue or organ). Accordingly, the invention also provides an article of the invention that further comprises a targeting agent (e.g. an antibody, a dendrimer, or a DNR or RNA sequence) associated with the mesoporous silicate or with the cap, wherein the targeting agent selectively delivers the article to a pre-selected site in the target environment (e.g. an animal).

Caps or dendrimers can be "associated" to the mesoporous silicates through ionic, covalent or other bonds (e.g. electrostatic interactions). For example, the caps or dendrimers can be covalently bonded to the mesoporous silicates either directly or through a linking group. Chemical modifications of targeting agents, such as introducing trialkoxysilyl group to the surface functionalities of antibody, dendrimer, or DNA or RNA, can provide sites for covalent or non-covalent attachment to the mesoporous silicate. For example, trialkoxysilyl-derivatized targeting agents can be grafted to the silicate surface.

DNA molecules can be "associated" to particles of the invention (e.g. particles having surface associated dendrimers) through ionic, covalent or other bonds (e.g. electrostatic interactions). The polyanionic nature of plasmid DNA's or genes makes them electrostatically attractive to positively charged dendrimers, such as poly(amidoamine) (PAMAM) and poly(propylenimine) (PPI), under physiological condition (pH 7.4). Thus, introduction of DNA to PAMAM or PPI coated mesoporous silicates facilitates a strong and multivalent binding between the DNA and the dendrimer-silicate composite material.

The mesoporous silica particles of the invention that comprise therapeutic or diagnostic agents can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the mesoporous silica particles of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The mesoporous silica particles of the invention may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the mesoporous silica particles of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the mesoporous silica particles of the invention will generally be administered as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the mesoporous silica particles of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The invention will now be illustrated by the following non-limiting Examples.

General Reagents and Materials. Cadmium nitrate tetrahydrate (99.99%), sodium sulfide, mercaptoacetic acid, 3-mercaptopropyltrimethoxysilane (MPTMS), N-cetyltrimethylammonium bromide (CTAB), tetraethyl orthosilicate (TEOS), 2-aminoethanethiol hydrochloride, 1-[3-(dimethylamino)propyl]-3-ethylcarbodiimide hydrochloride (EDC), dithiothreitol (DTT), and aldrithiol-2 were purchased (Aldrich) and used as received. Vancomycin hydrochloride and adenosine triphosphate disodium salt (ATP) were obtained from Sigma and used without further purification. Nanopure water (18.1 MHz) prepared from a Barnstead E-pure water purification system was employed throughout. PBS buffer (10.00 mM, pH 7.4) solutions with the total ionic strength of 0.06 M were prepared and used as the solvent for all the loading and release experiments of vancomycin and ATP.

EXAMPLES

Example 1

Drug-Loaded Mesoporous Silica Particles Capped With CdS a. Loading of Vancomycin and ATP into a Mesoporous Framework of Linker-MSN and Capping the Mesopores with Mercaptoacetic Acid-Functionalized CdS Nanoparticles.

Purified linker-MSN material from sub-part (b) below (100.00 mg) was incubated in a PBS buffer solution (0.60 mL, pH 7.4) of ATP or vancomycin (3.00 μmol in both cases) for 24 hours. Mercaptoacetic acid-functionalized CdS nanoparticles from sub-part (c) below (0.15 mmol) were dissolved in 2.00 mL of PBS buffer with vancomycin or ATP (0.01 mmol in both cases); 1-[3-(dimethylamino)propyl]-3-ethylcarbodiimide hydrochloride (EDC) (57.50 mg, 0.30 mmol) was added to the CdS/drug solution. The reaction mixture was allowed to stir for 24 hours, followed by centrifuging the suspension at 12 000 rpm for 3 minutes. The resulting precipitates (ATP- or vancomycin-loaded, CdS-capped MSNs) were isolated and dried under vacuum.

b. Synthesis of MCM-41-Type Mesoporous Silica Nanosphere with 2-(Propyldisulfanyl)ethylamine Functionality (Linker-MSN).

Figure 2:
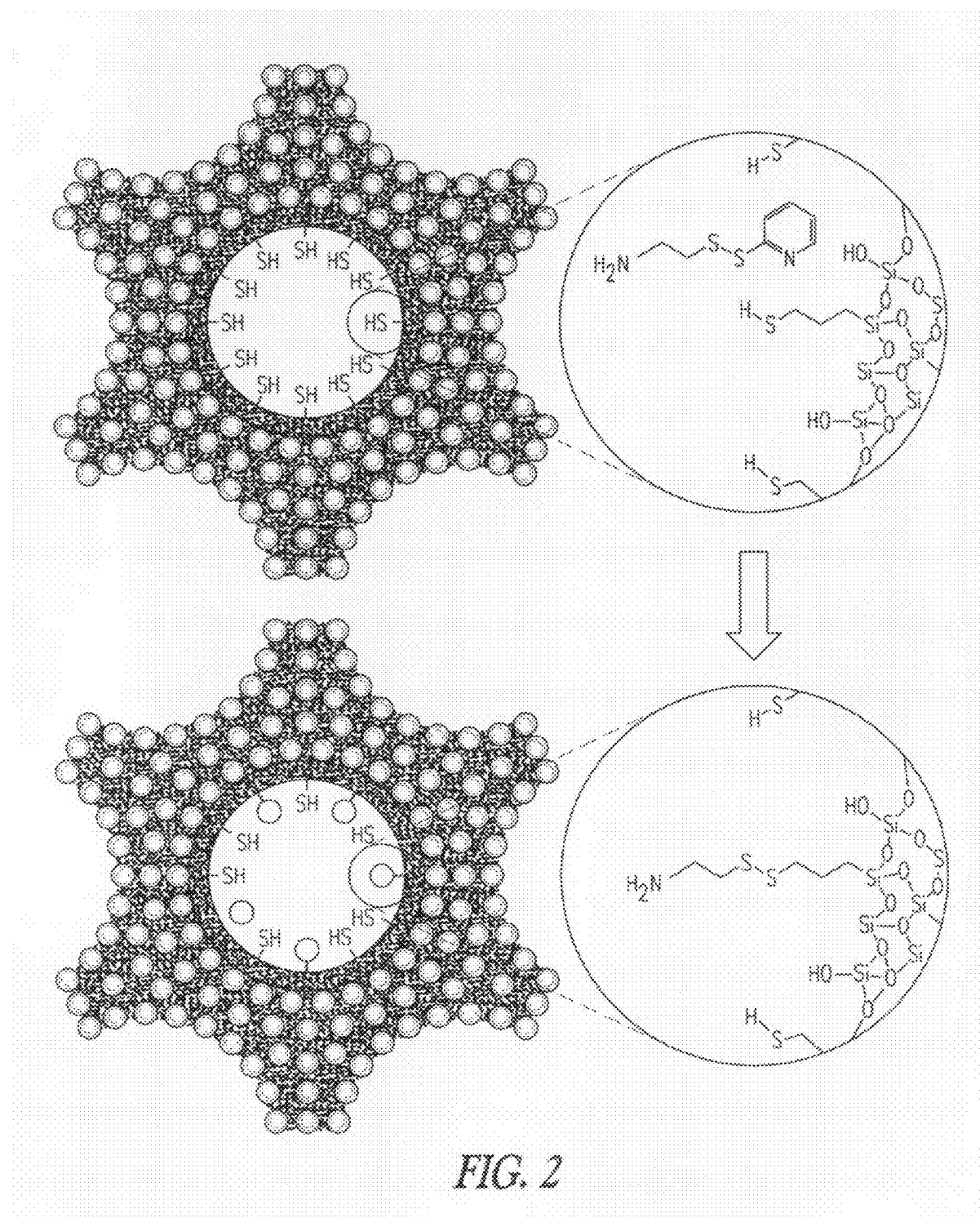
FIG. 2 illustrates the synthesis of 2-(propyldisulfanyl)ethylamine functionalized mesoporous silica nanosphere (linker-MSN) material.

As described below in detail, a mercaptopropyl-derivatized mesoporous silica nanosphere material (thiol-MSN) was synthesized using a method similar to that described by Lin, V. S.-Y., et al., *J. Am. Chem. Soc.* 2001, 123, 11510-11511; and Lin, V. S.-Y., et al., *J. Am. Chem. Soc.* 2002, 124, 9040-9041. As illustrated in FIG. 2, the surfactant-removed thiol-MSN material was treated with a methanol solution of 2-(pyridyldisulfanyl)ethylamine at room temperature for 24 hours under vigorous stirring to yield the MSN material with 2-(propyldisulfanyl)-ethylamine functionality (linker-MSN).

N-Cetyltrimethylammonium bromide (CTAB, 1.00 g, $2.74 \times 10^{-3}$ mol) was dissolved in 480 mL of Nanopure water. NaOH(aq) (2.00 M, 3.50 mL) was added to CTAB solution, followed by adjusting the solution temperature to 353 K. TEOS (5.00 mL, $2.57 \times 10^{-2}$ mol), was introduced dropwise to the surfactant solution, followed by the dropwise addition of MPTMS (0.97 mL, $5.13 \times 10^{-3}$ mol). The mixture was allowed to stir for 2 hours to give white precipitates (as synthesized thiol-Sphere). The solid product was filtered, washed with deionized water and methanol, and dried in air. To remove the surfactant template (CTAB), 1.50 g of as-synthesized thiol-Sphere was refluxed for 24 hours in a solution of 9.00 mL of HCl (37.4%) and 160.00 mL of methanol followed by extensive washes with deionized water and methanol. The resulting surfactant-removed thiol-MSN material was placed under high vacuum to remove the remaining solvent in the mesopores. The chemically accessible thiol group surface coverage of the thiol-MSN material was quantified to be $7.64 \times 10^{-4}$ mol/g using the method described by Lin, V. S.-Y., et al., *J. Am. Chem. Soc.* 2001, 123, 11510-11511. The purified thiol-MSN material (1.00 g) was treated with a methanol solution (60.00 mL) of 2-(pyridyldisulfanyl)-ethylamine (PDEA) ($9.12 \times 10^{-4}$ mol, prepared as described by Ebright, Y. W., et al., *Bioconjugate Chem.* 1996, 7, 380-384) at room temperature for 24 hours under vigorous stirring to undergo the desired disulfide bond exchange reaction. The resulting MSN material with 2-(propyldisulfanyl)ethylamine functionality was filtered and washed with methanol and dried in air.

c. Synthesis of Mercaptoacetic Acid-Derivatized Cadmium Sulfide (CdS) Nanoparticles.

The synthetic procedures were modified from those reported by Colvin, V. L., et al., *J. Am. Chem. Soc.* 1992, 114, 5221-5230. Mercaptoacetic acid ($2.15 \times 10^{-3}$ mol, 150.00 μL) was added to an aqueous solution (270.00 mL) of cadmium nitrate tetrahydrate ($3.00 \times 10^{-4}$ mol), forming a turbid blue solution. The pH was adjusted to 11 with 0.01 M NaOH. Sodium sulfide ($1.50 \times 10^{-4}$ mol) was dissolved in 10.0 mL of $H_2O$ and rapidly added to the cadmium nitrate solution with vigorous stirring. The reaction mixture was protected from light, stirred for 10 minutes, and concentrated to about one-tenth of its original volume with a rotary evaporator. Anhydrous methanol was added to provide the mercaptoacetic acid-capped water-soluble cadmium sulfide nanoparticles (CdS) as a precipitate.

d. Instrumental Methods, Conditions, and Parameters for the Structure Characterizations of Linker-MSN and CdS-Capped MSN Materials.

Powder XRD diffraction data were collected on a Scintag XRD 2000 X-ray diffractometer using Cu Kα radiation. Nitrogen adsorption and desorption isotherm, surface area (SA), and median pore diameter (MPD) were measured using a Micromeritics ASAP2000 sorptometer. Sample preparation included degassing at 130° C. for 1 hour. Nitrogen adsorption and desorption isotherms of these materials were obtained at −196° C. Specific surface areas and pore size distributions were calculated using the Brunauer-Emmett-Teller (BET) and Barrett-Joyner-Halenda (BJH) method, respectively. Particle morphology of these materials was determined by scanning electron microscopy (SEM) using a JEOL 840A scanning electron microscope with 10 kV accelerating voltage and 0.005 nA of beam current for imaging. For transmission electron microscopy (TEM) studies, a small aliquot was removed and placed between two clean glass slides. Slides were squeezed between fingers and rubbed back and forth to break up larger clumps. The resulting powder was washed into a Petri dish with acetone. The mixture was stirred and ultrasonically agitated. While still in suspension a lacey carbon-coated TEM grid was pulled through the suspension. The grid was allowed to dry in air and then examined in an Amray 1845 FE-SEM followed by examination with a Philips model CM-30 TEM operated at 300 kV. The specimen was given no further treatment, as it appeared stable under beam bombardment. The preparation for the microtomed samples included embedding into a derivation of EPON epoxy resin using EmBed 812. This mixture was centrifuged and cured for 24 hours at 60° C. The embedded block was microtomed to obtain thin sections of 60-80 nm thickness by using a Reichert Ultracut S ultramicrotome with a diamond knife (Diatome). The floated sections were mounted on a 400 mesh Pd-coated Cu grid. The TEM images of these microtomed samples were recorded using a Philips model CM-30 TEM operated at 300 kV at 69 000 to 340 000 electron optical magnification.

e. Results

Figure 3A:
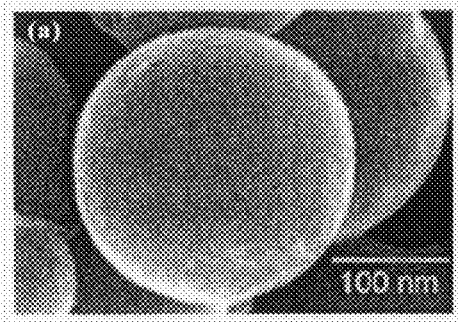
FIG. 3 SEM (a and b) and TEM (300 kV) micrographs of the linker-MSN (c and e). The MCM-41 type of mesoporous channel structure of the nanospheres is visualized with the parallel stripes (c) and the hexagonally packed light dots (e) shown in the micrographs. The TEM micrographs (d and f) of the CdS-capped MSN clearly exhibit aggregations of CdS nanoparticles on the exterior surface of MSN material represented by dots in the areas indicated by black arrows in (d). A large area (left side of the MSN particle indicated by the blue arrow) displaying light dots packed in a disordered symmetry and an area (green arrow) where the mesopores are hexagonally arranged represent the CdS nanoparticle-capped and uncapped areas of MSN particle shown in (f), respectively. The TEM micrographs (d-f) were measured on ultramicrotomed samples with section thickness of 60-80 nm FIG. 4 Low (a) and high (b) angle powder X-ray diffraction patterns (XRD) of the linker-MSN material before (solid line) and after (dashed line) the immobilization of CdS nanocrystals. (# is the diffuse peak of noncrystalline silica.).
Figure 3B:
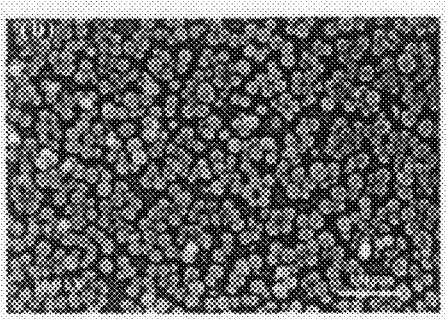

As depicted in FIGS. 3a, b, c, and e, the spherical particle shape and the MCM-41 type of hexagonally packed mesoporous structure of the linker-MSN material were confirmed by scanning and transmission electron microscopy (SEM and TEM, respectively). The $N_2$ adsorption/desorption isotherms of the material further revealed a BET isotherm typical of MCM-41 structure (type IV) with a surface area of 941.0

$m^2/g$ and a narrow BJH pore size distribution (average pore diameter=2.3 nm). The linker-MSN (100.0 mg) was used as a chemically inert host to soak up the aqueous solutions of vancomycin (3.0 µmol) and ATP (15.5 µmol).

As illustrated in FIG. 1, the water-soluble CdS nanocrystals (average particle diameter of 2.0 nm) with mercaptoacetic acid groups were covalently captured and formed amide bonds by reacting with the mesopore surface-bound 2-(propyldisulfanyl)ethylamine linkers of the MSN/drug composite material in aqueous solutions. The resulting reaction suspensions were centrifuged, and the CdS-capped MSN/drug composite materials along with the unreacted CdS nanoparticles were filtered. The concentrations of the free vancomycin and ATP molecules in the filtrate were then determined by HPLC. The calculated concentration decreases of solution vancomycin and ATP were attributed to the amounts of mesopore-encapsulated vancomycin (2.5 µmol) and ATP (4.7 µmol) per 100.0 mg of linker-MSN material. These numbers correspond to ca. 83.9 and 30.3 mol % loading efficiency, respectively.

Figure 4A:
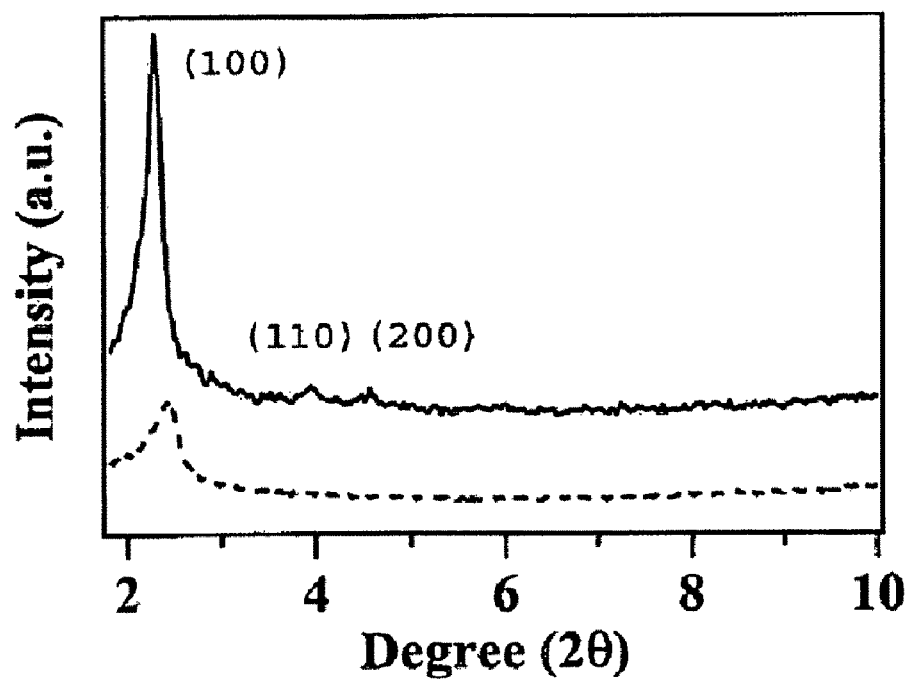

The successful incorporation of CdS nanoparticles to the MSN matrix was confirmed by various spectroscopy methods. As shown in FIG. 4a, the covalent immobilization of the surface-functionalized CdS nanoparticles to the linker-MSN material reduced the intensity of the powder X-ray diffraction (XRD) peaks. Such a reduction of scattering contrast between the pores and the framework of the MCM-41 materials due to the pore-filling effect has been reported previously in the literature by Marler, B., et al., *Microporous Mater.* 1996, 6, 375-383; Winkler, H., et al., *Adv. Mater. (Weinheim, Ger.)* 1999, 11, 1444-1448; Zhang, W.-H., et al., *Chem. Mater.* 2000, 12, 1408-1413; and Zhang, W.-H., et al., *Chem. Mater.* 2001, 13, 648-654. Compared with the $d_{100}$ value of the linker-MSN material, a small increase in that of CdS-capped MSN was observed. The increase of the $d_{100}$ values may be attributed to the covalent linkage induced pore-filling effect between the CdS nanoparticles and the mesoporous silica matrix.

Figure 4B:
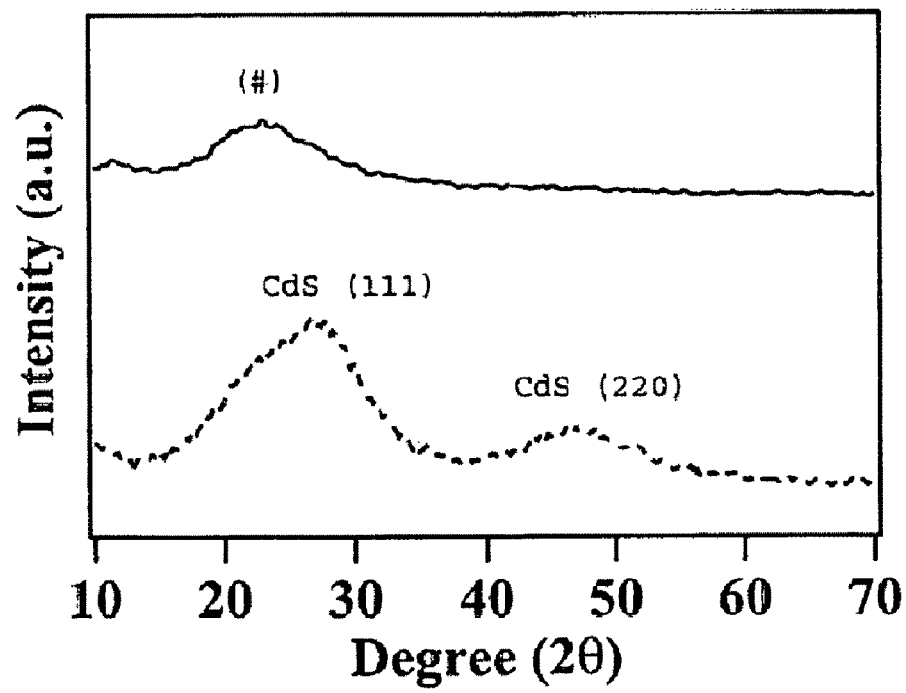

FIG. 4b showed the high-angle XRD diffraction patterns of the linker-MSN and the CdS-capped MSN materials within the 2θ range of 10°-70°. In contrast to the low-intensity diffuse peak of noncrystalline silica observed in the linker-MSN material (FIG. 4b), two additional peaks are detected in the CdS-capped MSN sample. As depicted in FIG. 4b, these two peaks are attributed to the diffraction of (111) and (220) lattice planes of the CdS nanoparticles attached to the mesoporous silica. See Kumar, A., et al., *Langmuir* 2000, 16, 9299-9302; Diaz, D., et al., *J. Phys. Chem. B* 1999, 103, 9854-9858; Weller, H., et al., *Chem. Phys. Lett.* 1986, 124, 557-560; and Yang, J., et al., *Chem. Mater.* 2000, 12, 3259-3263. To further confirm that these CdS nanoparticle "caps" were indeed covalently linked to the mesopore surface-bound linker groups, the $^{13}C$ solid-state CP-MAS NMR spectra of both the CdS-capped MSN and the linker-MSN were carefully compared and the existence of the covalent linkage between the CdS and MSN materials was clearly observed.

Figure 3C:
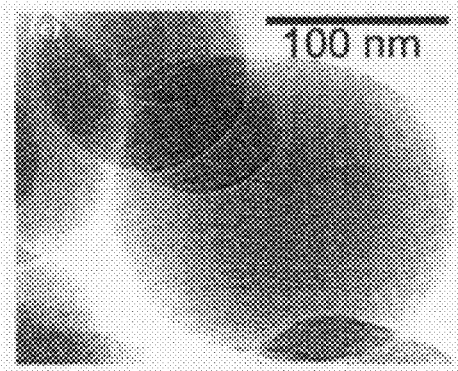
Figure 3D:
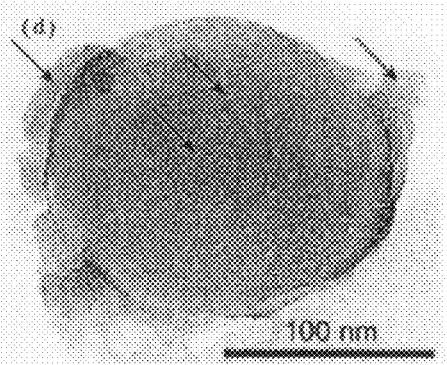
Figure 3E:
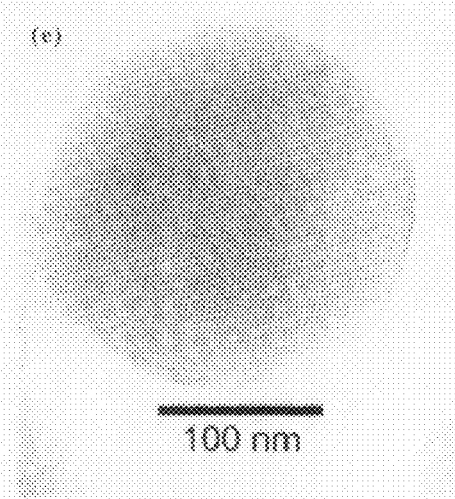
Figure 3F:
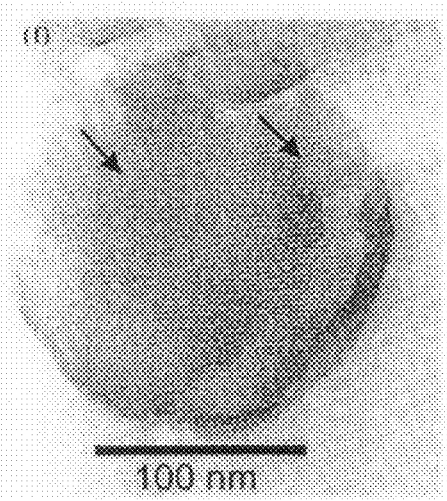

TEM investigations of the CdS-capped MSN also provided direct evidence of the CdS distribution both on and in the organically functionalized MSN material. As shown in FIG. 3d, where the mesopores (porous channels) are represented by the alternating black and white stripes, the CdS nanoparticles are clearly visible on the outside edge and inside the mesopores of the MSN depicted by the lighter areas (indicated by the arrowheads). As opposed to these features observed in the case of CdS-capped MSN, the TEM micrograph of the linker-MSN (FIG. 3c) prior to the CdS "capping" showed smooth edges and nice contrasts between the mesoporous channels and the silica matrix. Furthermore, compared with the periodically well-organized hexagonal array of mesopores represented by the bright dots shown on the TEM micrograph of the linker-MSN orientated along the pore axis (FIG. 3e), an additional layer of CdS nanoparticles on the outside of the MSN material and a large area of disordered hexagonal array of mesopores indicated by the arrows in FIG. 3f were observed in the case of CdS-capped MSN material. In contrast to the "disordered" area, a small area with mesopores that are packed with a hexagonal symmetry was also noticed on the micrograph. These different areas could be attributed to the fact that most, but not all, mesopores are capped with the CdS nanoparticles.

Example 2

DTT-Induced Drug/Neurotransmitter Release Study

CdS-capped MSN with vancomycin or ATP (10.00 mg) material was dispersed in 1.50 mL of PBS buffer (pH 7.4), followed by repeating wash/sonication/centrifugation cycles for five times to remove physisorbed, uncapped vancomycin or ATP molecules on the exterior surface of the material. The purified MSN/drug composite was redispersed in 3.50 mL of PBS buffer (pH 7.4). Aliquots were taken every 4 hours over a time period of 12 hours from the MSN/water suspension and injected to an analytical HPLC system (Hitachi LC/3DQMS with a reverse phase C18 column (Vydac), 0.4 cm×25 cm) to monitor the leaching of the mesoporous channel encapsulated vancomycin or ATP molecules. After 12 hours, dithiothreitol (DTT, 18.50 mM) was added to the suspension to cleave the disulfide linkage between the CdS nanoparticle and the MSN. The kinetic profiles of the DTT-induced release of vancomycin and ATP were monitored by following two literature-reported HPLC separation conditions. The peaks/areas at 280 and 258 nm were monitored/integrated for the quantitative analysis of amounts of released vancomycin and ATP, respectively. See Farin, D., et al., *J. Pharm. Biomed. Anal.* 1998, 18, 367-372; and Veciana-Nogues, M. T., et al., *Food Chem.* 1997, 59, 467-472.

Results

Figure 5A:
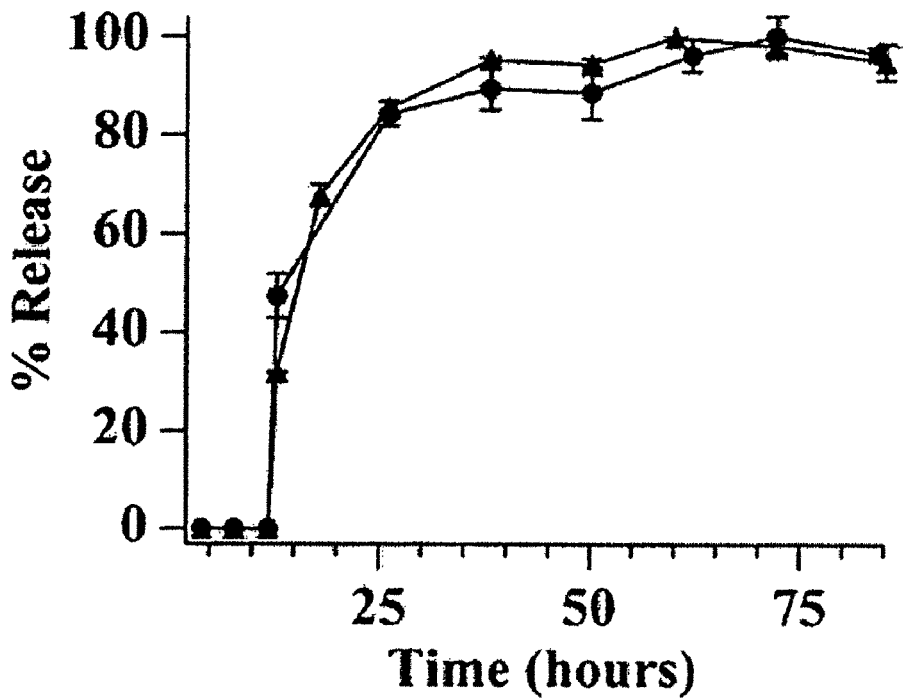
FIG. 5 Illustrates the DTT-induced release profiles of Vancomycin (-•-) and ATP (- -▲- -) from the CdS-capped MSN system: (a) % release over time. (b) The DTT concentration-dependent releases. Released analyte concentrations were measured with CdS-MSNs (2.3 mg) in pH 7.4 PBS buffers (0.8 mL) after 24 hours of the DTT additions.
Figure 5B:
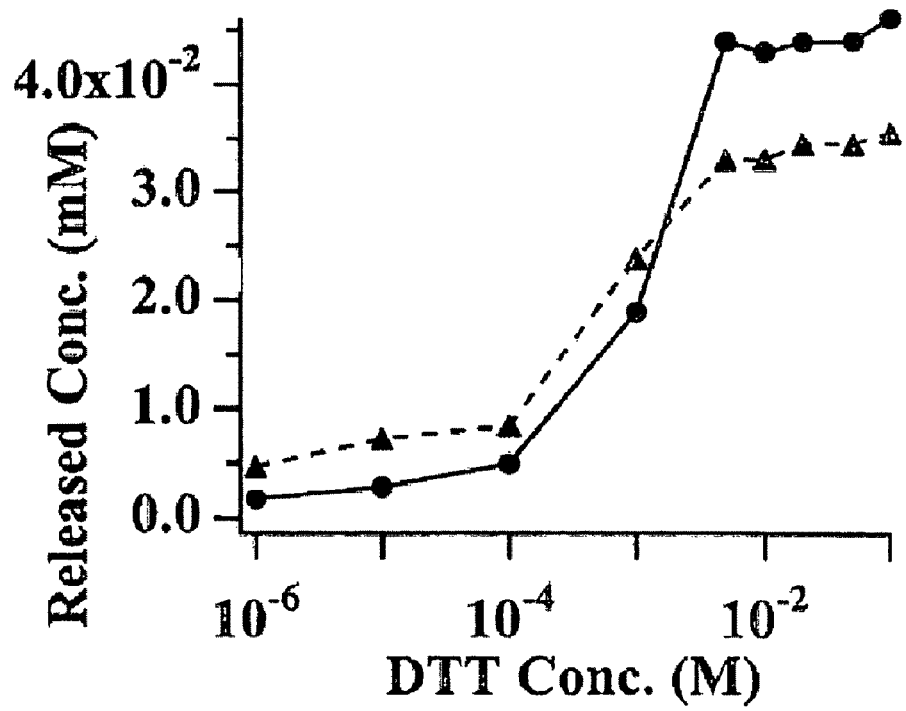

As shown in FIG. 5a, the CdS-capped MSN drug/neurotransmitter delivery system exhibited less than 1.0% of drug release in 10 mM PBS buffer solutions (pH 7.4) over a period of 12 hours. The result suggested a good capping efficiency of the CdS nanoparticles for encapsulation of the vancomycin and ATP molecules against the undesired leaching problem. Addition of disulfide-reducing molecules, such as DTT and ME, to the aqueous suspension of CdS-capped MSNs triggered a rapid release of the mesopore-entrapped drug/neurotransmitter. Within 24 hours, the release reached 85% of the total release seen in 3 days of vancomycin and ATP after the introduction of 18.5 mM DTT (FIG. 5a). Interestingly, the rates of release of vancomycin and ATP showed similar diffusional kinetic profiles, indicating the lack of interaction between these released molecules and the mesoporous silica matrix. However, 53.8% (1.6 µmol) of the encapsulated vancomycin was released after 3 days of the DTT-induced uncapping of the mesopores, while only 28.2% (1.3 µmol) of the entrapped ATP molecules was able to diffuse away. Such a large difference between the portion of vancomycin and ATP released from the MSN material implied that ATP molecules were more strongly physisorbed to the organically functionalized mesoporous channels than the vancomycin molecules. On the basis of several reports in the literature, (Takacs-Novak, K., et al., *Int. J. Pharm.* 1993, 89, 261-263) vancomycin has an isoelectric point (pI) of 8.3 and therefore is cationically charged under our experimental condition (pH 7.4). Conversely, ATP is anionic in pH 7.4 aqueous solutions. Given that the surface of the linker-MSN material is decorated with the 2-(propyldisulfanyl)ethylamine functionality, which is cationic (ammonium cation) at pH 7.4, the attractive electrostatic interaction between the ATP molecules and the linker-functionalized mesopores could be attributed to the stronger physisorption of ATP, whereas the repulsive electrostatic interaction between vancomycin molecules and the linker-derivatized mesopores disfavor the surface adsorption of vancomycin. These results suggested that perhaps only those molecules that are not in direct contact with the pore surface, i.e., nonphysisorbed molecules, could be released under our experimental conditions. Furthermore, in both vancomycin and ATP cases, the amount of drug release after 24 hours of the addition of DTT showed similar DTT concentration dependencies (FIG. 5b), indicating the rate of release is dictated by the rate of removing the CdS caps.

Example 3

Controlled-Release Studies of CdS-Capped, ATP-Encapsulated MSN with Neuroglia Cells (Astrocytes) in Vitro a. Methods.
(i) Wistar rats, raised at Iowa State University, were used for these experiments. Animal care and experimental protocols were in accordance with the guidelines and approval of the Iowa State University Committee on Animal Care.
(ii) Cell Cultures. Enriched primary astrocyte cultures from neonatal ($P_0$ to $P_3$) rat cerebral cortex were prepared as previously described by Jeremic, A., et al., *J. Neurochem.* 2001, 77, 664-675. Briefly, freshly dissected cortical tissues from three animals were incubated 50 minutes at 37° C. in 2.00 mL of Earle's balanced salt solution (EBSS; Gibco-Invitrogen Co.) containing papain (1.54 mg/mL; Sigma-Aldrich Co.). After incubation, tissue was rinsed with EBSS solution and incubated for 5 minutes in trypsin-inhibitor solution (1 mg/mL; Gibco-Invitrogen Co.). After being rinsed, once with EBSS solution and once with culture medium (consisting of α-minimum essential medium (α-MEM; Gibco-Invitrogen Co.) supplemented with 10% heat-inactivated fetal bovine serum (FBS; Gibco-Invitrogen Co.) and 1.00 mL of penicillin-streptomycin solution (Sigma-Aldrich Co.) per 100 mL), the tissue was mechanically dispersed in culture medium by triturating through a fire-polished glass pipet. The cell suspension was transferred to sterile 15-mL centrifuge tubes and spun at 1000 g for 10 minutes. Cell pellets were resuspended in culture medium (α-MEM supplemented with 10% heat-inactivated FBS and 1.00 mL of penicillin-streptomycin solution per 100.00 mL) and plated in culture flasks. Cells were maintained at 37° C. in a humidified 5% $CO_2$/95% air atmosphere. Culture medium was changed every 2 to 3 days. When mixed cultures reached confluence (9-12 days), the flasks were shaken (260 rpm) for 90 minutes to remove microglia and dividing type I astroglia. After shaking the cells, medium was replaced, and the flasks were incubated for 1 hour to equilibrate with $CO_2$ in the fresh medium. Cultures were then shaken overnight (12-18 hours) at 260 rpm at 37° C. Cultures enriched in type I astroglia were obtained by trypsinizing (0.25%; Sigma-Aldrich Co.) attached cells for 5 minutes. Trypsin was inactivated by adding α-MEM supplemented with the 10% heat-inactivated FBS (serum contains protease inhibitors). Cells were plated on poly-L-lysine-coated coverslips (10.00 μg/mL; MW 100 000; Sigma-Aldrich Co.) at a density of $3.00 \times 10^4$ cells/cm$^2$. All experiments were performed on cells that had been in culture for 2-4 days after replating.
(iii) Characterization of Glial Cultures. An antibody against glial fibrillary acidic protein (GFAP) was used to identify astrocytes following the procedure described in the subsequent Immunocytochemistry section. It was confirmed that glial cultures were neuron-free by using antibodies against the tubular protein MAP-2. In astrocyte-enriched cultures immunoreactivity for MAP-2 was absent, while neurons were immunopositive in parallel cultures that contained neurons.
(iv) Immunocytochemistry. After fixation with 4% paraformaldehyde (Fisher Chemical) for 30 minutes at room temperature, cells were incubated for 30 minutes in a 50% goat serum solution containing 1% bovine serum albumin (BSA; Sigma-Aldrich Co.) and 100.00 mM L-lysine (Sigma-Aldrich Co.), to block nonspecific binding, and 0.4% Triton X-100 to permeabilize the membrane. Immunocytochemistry was performed using antibodies raised against glial fibrillary acidic protein (GFAP; 1:5000; Sigma-Aldrich Co.) and microtubule associated protein (MAP-2; 1:2000; Sigma-Aldrich Co.). Positive controls were established with these antibodies using cortical glia and neurons. Negative controls were established by omitting the specific antiserum. Antibody visualization was accomplished by the employment of the biotinylated secondary antibody, the Vectastain ABC kit (Vector) and the nickel-enhanced 3-3'-diaminobenzidine method. See Jeftinija, S., et al., *Regul. Pept.* 1992, 39, 123-135. Cells were dehydrated in graded alcohol, cleaned in xylene, and sealed with acrytol on glass slides.
(v) Intracellular Calcium Imaging. The effect of experimental manipulation on the intracellular calcium concentration ($[Ca^{2+}]_i$) of cultured cells was evaluated by ratiometric imaging techniques. See Jeftinija, S. D., et al., *J. Neurochem.* 1996, 66, 676-684. Cells were loaded with Fura 2-AM (5.00 μM; Molecular Probes) for 40-60 minutes at 37° C.; 1.00 μL of 25% (w/w) of Pluronic F-127 (Molecular Probes) was mixed with every 4.00 nM of AM ester to aid solubilization of the ester into aqueous medium. Coverslips containing glial cells were washed with normal Hepes-saline solution and further incubated for 10 minutes at 37° C. to allowed de-esterification of Fura 2-AM. Normal Hepes-saline solution contains (in mM): NaCl 140.00, KCl 5.00, $MgCl_2$ 2.00, $CaCl_2$ 2.00, and HEPES (Sigma-Aldrich Co.) 10 (pH 7.4). All image processing and analysis were performed using an Attofluor system with Zeiss microscope. Background subtracted, rationed images (340/380 nm) were used to calculate the $[Ca^{2+}]_i$ according to a literature-reported method. See Grynkiewicz, G., et al., *J. Biol. Chem.* 1985, 260, 3440-3450. Calibration was performed in situ according to the procedure provided by the Attofluor, using the Fura-2 Penta $K^+$ salt (Molecular Probes) as a standard. Using wavelengths of 340 and 380 nm, Fura 2-AM was excited, and the emitted light was collected at 520 nm.

b. Results

To demonstrate the biocompatibility and utility of the mesoporous silica particles of the invention for selective stimulation of certain cell types, ATP-loaded MSNs were introduced into an established astrocyte culture. It has been previously shown that ATP molecules evoke a receptor-mediated increase in intracellular calcium in astrocytes (Jeremic, A., et al., *J. Neurochem.* 2001, 77, 664-675; Neary, J. T., et al., *Brain Res.* 1991, 566, 89-94; and Zhu, Y. and Kimelberg, H. K. *J. Neurochem.* 2001, 77, 530-541), which is an important regulatory mechanism for many intercellular communications and cooperative cell activities (Wang, Z., et al., *Anal. Chem.* 2000, 72, 2001-2007; and Newman, E. A. and Zahs, K. R. *Science* (Washington, D.C.) 1997, 275, 844-847). Astrocyte type-1 cultures were obtained from neonatal rats by following previously published protocol (Jeftinija, S. D., et al., *J. Neurochem.* 1996, 66, 676-684) to ensure the absence of neurons that complicate experimental interpretation. Phase-contrast microscopy indicated that cultures were indeed enriched in type-1 astrocytes and devoid of neurons. Immunocytochemistry experiments on these cells demonstrated that all the cultures are more than 95.0% immunopositive for glial fibrillary acidic protein (GFAP) and lacked MAP-2 immunoreactivity. The observed results further confirmed that these cultures are indeed type-1 astrocytes and not neurons. To determine the effect of ATP on cultured astrocytes, a ratiometric-imaging techniques (Jeftinija, S. D., et al., *J. Neurochem.* 1996, 66, 676-684; and Grynkiewicz, G., et al., *J. Biol. Chem.* 1985, 260, 3440-3450) was used to monitor the glial calcium levels. Cells were loaded with the membrane-permeant $Ca^{2+}$-chelating fluorescent dye (Fura-2 AM; see Grynkiewicz, G., et al., *J. Biol. Chem.* 1985, 260, 3440-3450), which is a widely used and highly sensitive indicator of intracellular calcium concentration ($[Ca^{2+}]_i$). The ATP-induced increases of $[Ca^{2+}]_i$ (calcium transients; see Grynkiewicz, G., et al., *J. Biol. Chem.* 1985, 260, 3440-3450) represented by the color changes (increases of fluorescence) of the pseudocolor images of the cells were detected using an Attofluor system with Zeiss microscope.

Figure 6A:
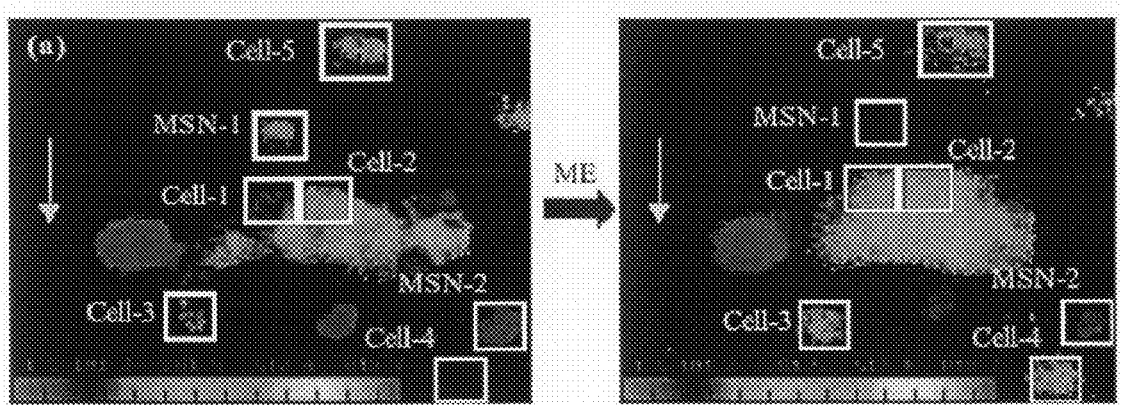
FIG. 6 shows the effect of ATP release from CdS-capped MSNs on astrocytes. (a) Top panels show the pseudocolor images of astrocytes loaded with Fura-2 at resting level (top left panel) and after the application of ME (top right panel). The yellow arrows indicate the flow direction of HEPES buffer (pH 7.4). (b) Left bottom panel shows the fluorescence of cells and CdS at 520 nm ($\lambda_{ex}$=380 nm). (c) Right bottom graph is a time course of astrocytes and CdS-capped MSN fluorescence prior to and after the application of ME. (Black bar represents the application time period of ME)
Figure 6B:
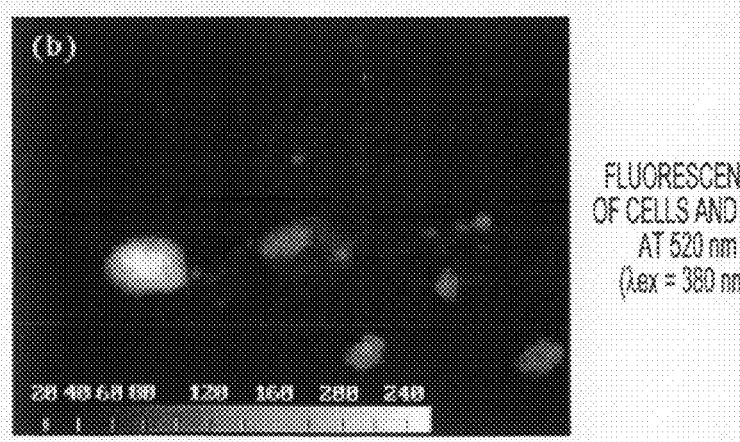
Figure 6C:
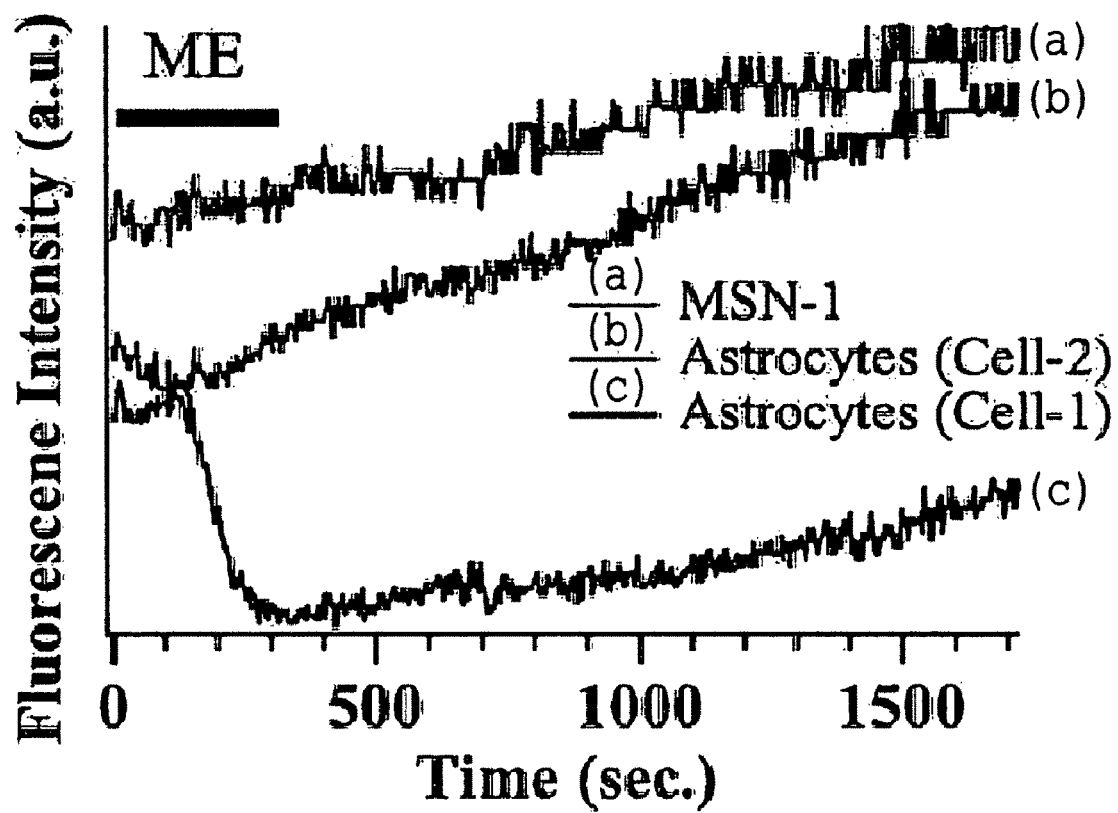

To measure the effect of ATP released from the MSN system, astrocytes cultured in the presence of surface immobilized, CdS-capped MSNs with ATP molecules encapsulated inside of the mesoporous channels were first loaded with Fura-2 AM and then placed in a flow cell with a volume of 50.0 μL and a flow rate of 200.0 μL/minute in a flow direction from the top to the bottom of the images shown in FIG. 6. As shown in FIGS. 6a and c, perfusion application of ME (1 mM for 5 minutes) resulted in a drastic decrease in the fluorescence intensity of CdS at the areas of the ATP-loaded MSN piles (MSN-1 and MSN-2) indicating the CdS caps have been released and diffused away from the surface-bound MSNs. Furthermore, a pronounced increase in intracellular $[Ca^{2+}]_i$ represented by the color change of the pseudocolor images of Cell-1 and -2 (FIG. 6a) and the corresponding upward shift of the red and blue curves of those two cells in the time course plot was observed (FIG. 6c). The observations suggested that the ATP molecules released from the mesoporous silica nanospheres located at the MSN-1 pile have reached their receptors on the cell surface of those astrocytes (for example, Cell-1 and -2) located at the downstream areas of the flow and thereby triggered the corresponding ATP receptor-mediated increase in intracellular calcium concentration. It is interesting to note that only the cells that were situated at the downstream areas relative to the MSN-1 pile (FIG. 6a) are stimulated by the perfusion application of ME. Throughout the whole period of ME application, no obvious color changes could be observed in the pseudocolor images of those astrocytes that were located at the upstream areas, such as Cell-5, as shown in FIG. 6a. The result indicated that the intracellular calcium concentrations of those "upstream" astrocytes relative to the MSN-1 pile were not affected by the perfusional introduction of ME. Given that the flow direction is from the top to the bottom of these images, such a phenomenon could be attributed to the fact that the ATP molecules released from the immobilized piles of MSNs by the perfusion application of ME could not diffuse against the flow to reach and stimulate the "upstream" astrocytes (Cell-5).

Figure 7A:
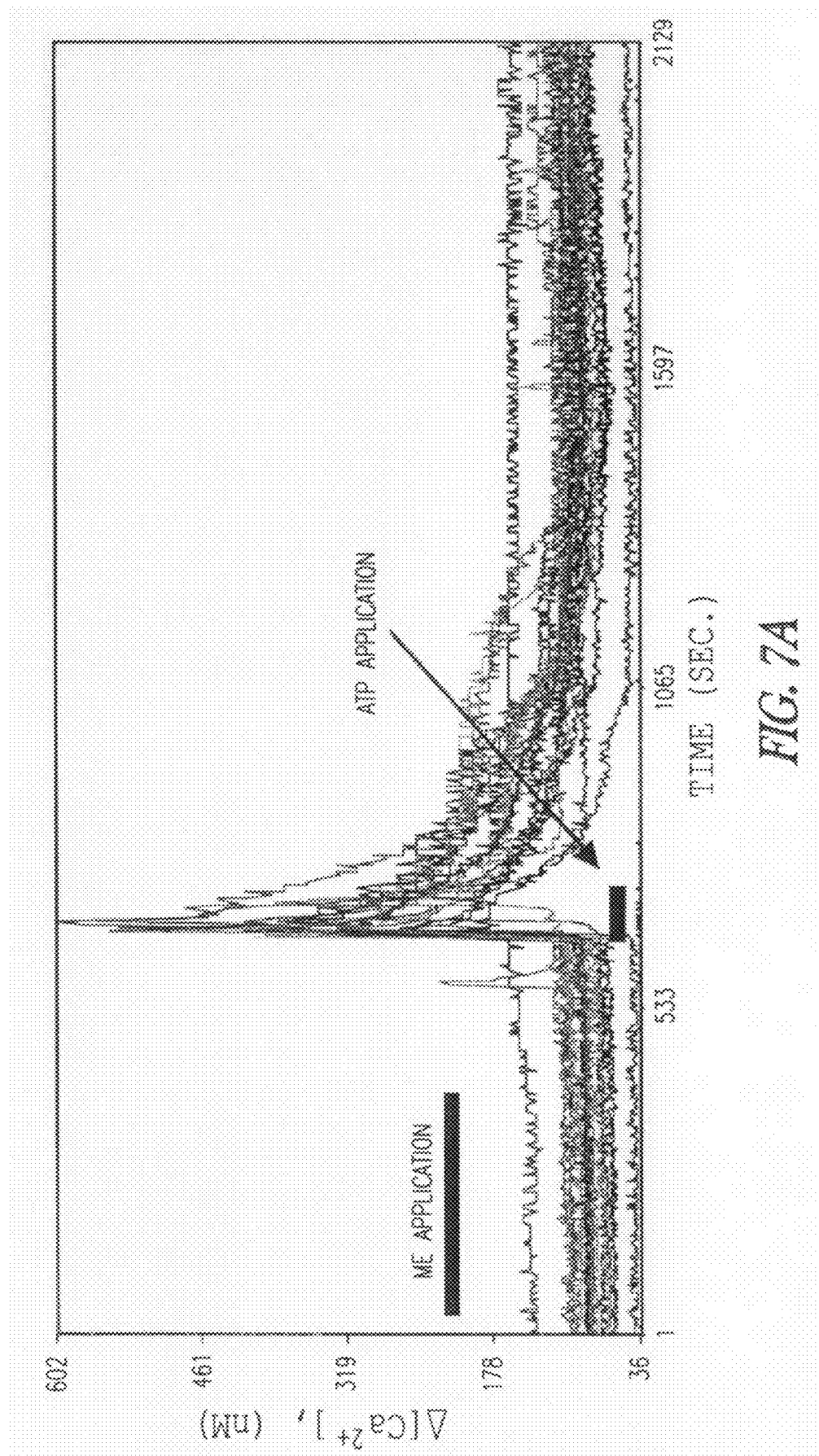
FIG. 7 (a) Images showing that application of ME on an astrocyte culture loaded with the intracellular $Ca^{2+}$-chelating fluorophore (Fura 2-AM) without the presence of MSN failed to produce any $[Ca^{2+}]_i$ response of astrocytes. (b) Pseudocolor image of astrocytes taken after the ME application showed no increase or decrease in $[Ca^{2+}]_i$ of the cells. (c) The same cells responded to the perfusion application of 100.0 μM ATP indicated by the increase of fluorescence intensity of the pseudo-color image of astrocytes, i.e., $[Ca^{2+}]_i$ increases.
Figure 7C:
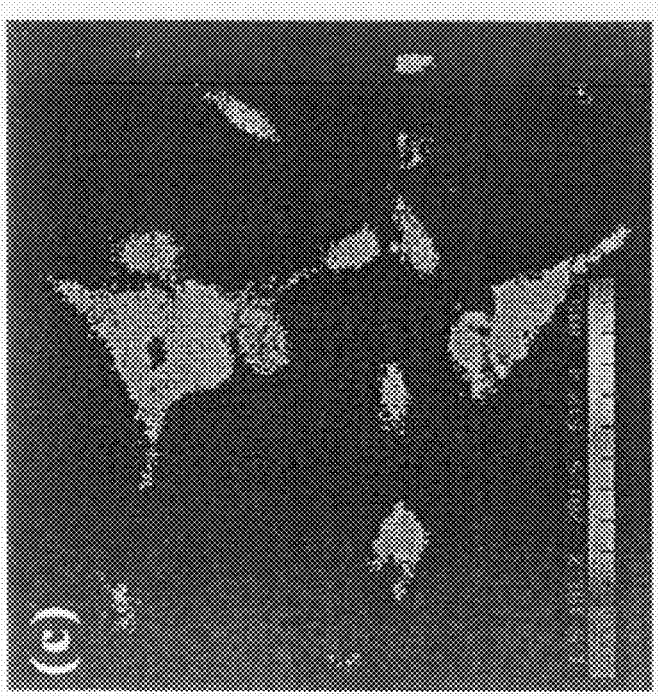
Figure 7B:
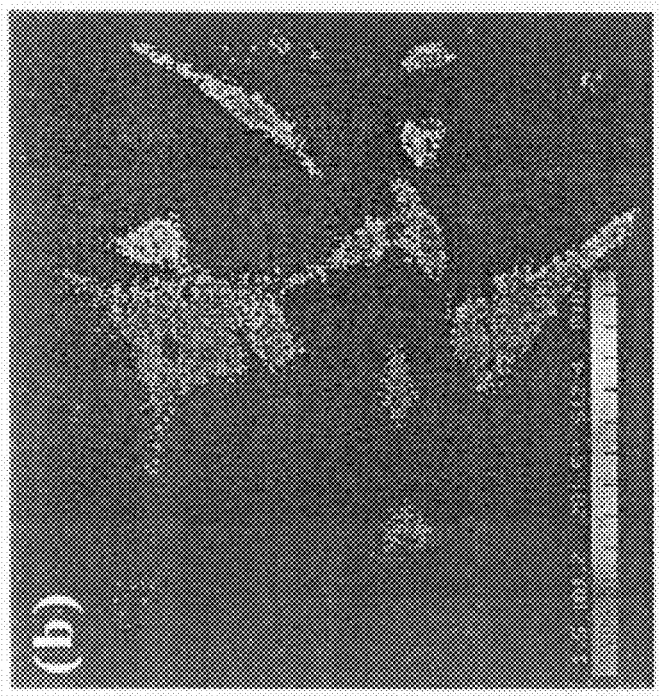

To confirm that the increase of $[Ca^{2+}]_i$ was not induced by the ME or the CdS released from the MSNs, two control experiments were performed. First, an enriched astrocyte type-1 culture via the same protocol but without the presence of MSNs was obtained. As shown in FIG. 7, the perfusion application of ME (1.0 mM for 5 minutes) to these cells showed no increase in $[Ca^{2+}]$. A high concentration of ATP (100.0 μM) was later introduced to these ME-treated astrocytes. All cells responded to the ATP application with obvious increases in $[Ca^{2+}]_i$. Clearly, the ME application did not stimulate the calcium channel activity of these astrocytes to create any noticeable increase in $[Ca^{2+}]_i$. Also, such ME treatments did not cause any obvious damage to these cells and they could still respond normally to ATP stimulation.

Figure 8D:
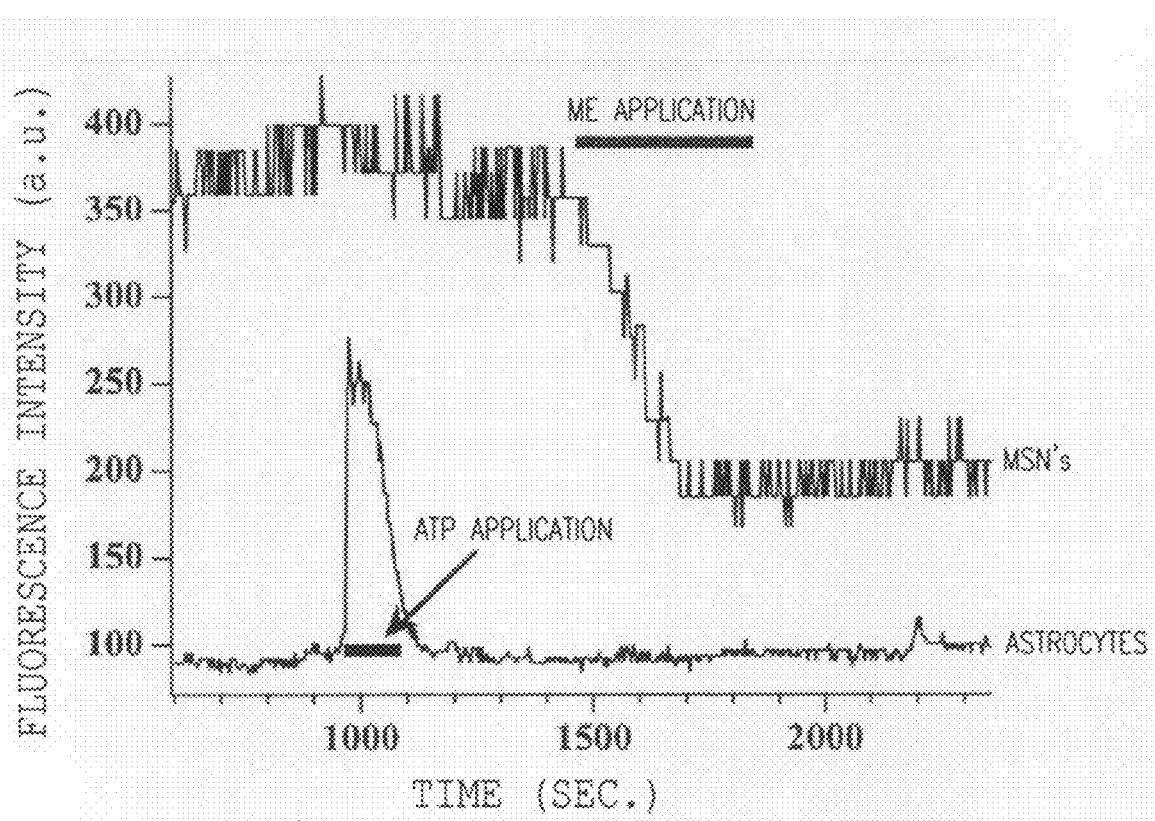
FIG. 8 Pseudo-color images of an astrocyte culture in the presence of random piles of CdS-capped MSNs with empty mesoporous channels (no ATP encapsulation) before (a) and after (b) the application of ATP (100.0 μM). An increase in $[Ca^{2+}]_i$ of the astrocytes (lower square, red) located adjacent to a pile of MSNs (upper square, yellow) upon the perfusion application of ATP was observed (d, lower curve). The result suggested that the astrocytes are responsive to ATP stimulation. Significant decrease of the fluorescence intensity (c and d, upper curve) of the pile of MSNs (upper square, yellow) was observed upon the perfusion application of ME due to the uncapping of CdS (diffusing away from the area of interest). Concurrently, the adjacent astrocytes did not show any detectable response during the application of ME.
Figure 9:
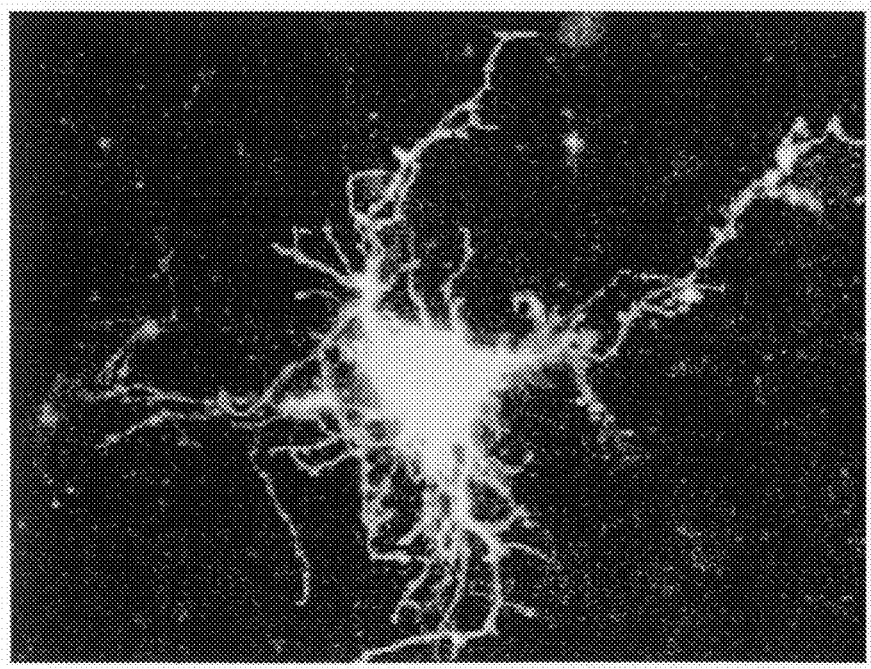
FIG. 9 Shows a fluorescence confocal micrograph of a cortical neuron transfected by the PAMAM-MSN gene transfer system as described in Example 4 (Excitation wavelength=488 nm).
Figure 10A:
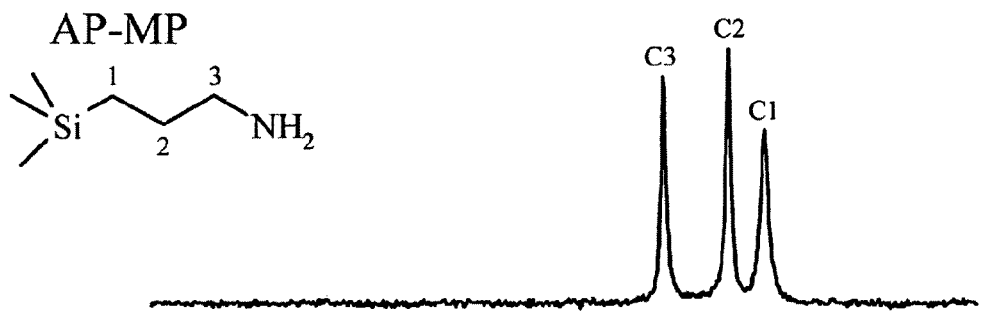
FIG. 10 $^1H\rightarrow^{13}C$. CPMAS spectra of AP-MP (a), AAP-MP (b), AEP-MP (c), UDP-MP (d), ICP-MP (e), CP-MP (f), AL-MP (g), and s-MCM-41 (h) using CP contact time of 0.4 (spectra a-c and h) or 1.5 ms (spectra d-g). Asterisks mark positions of residual surfactant carbons present in spectra f, and g. Note that spectrum (e) represents the propyl-carbamic acid group formed during the synthesis of ICP-MP by base-catalyzed hydrolysis of isocyanopropyl group.
Figure 10B:
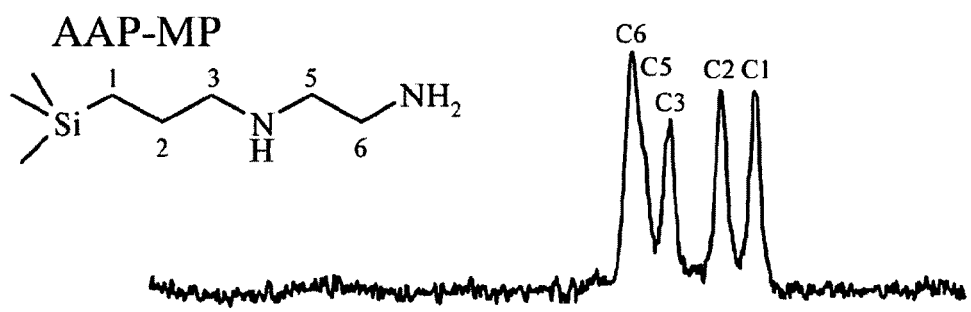
Figure 10C:
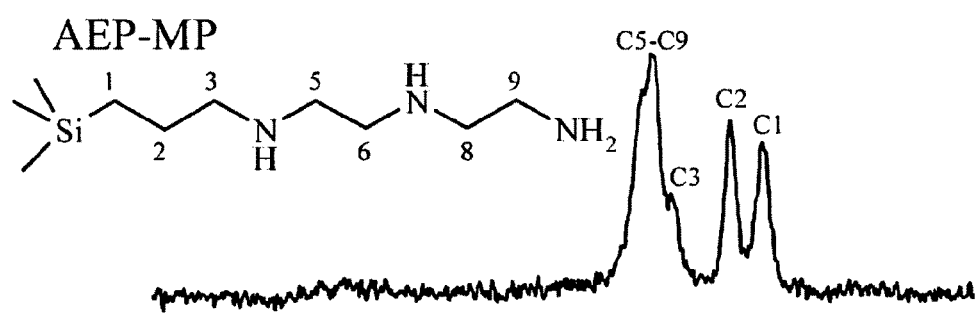
Figure 10D:
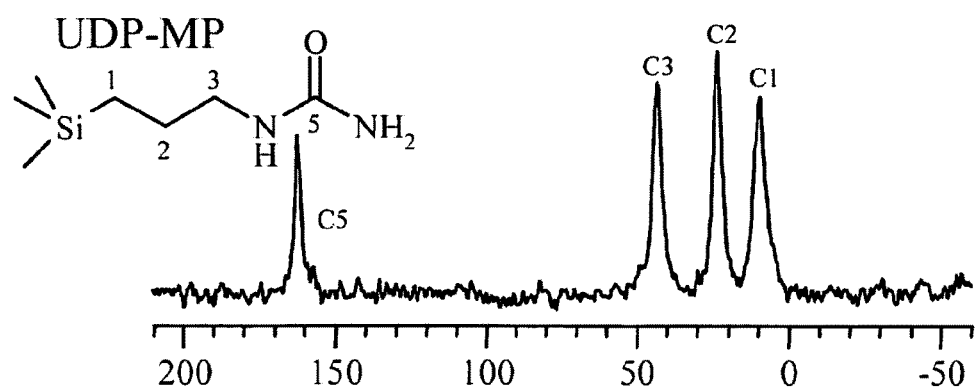
Figure 10E:
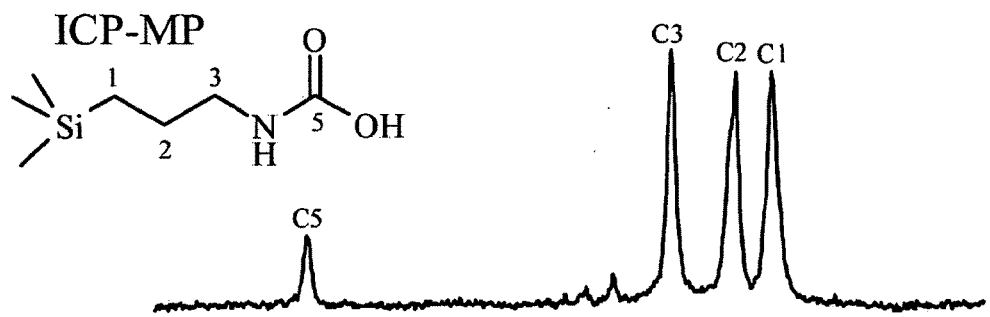
Figure 10F:
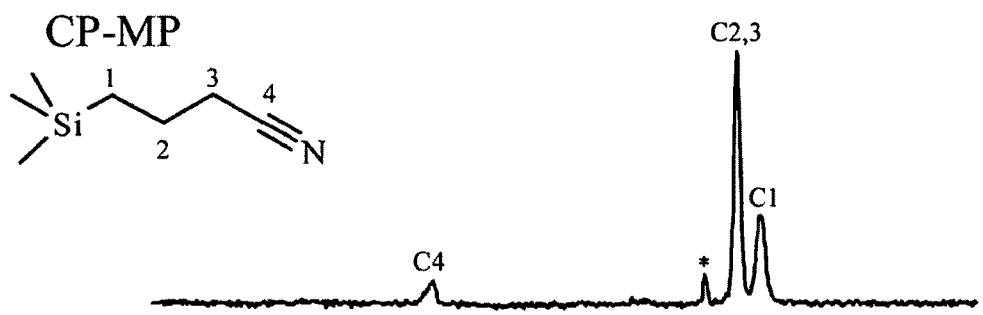
Figure 10G:
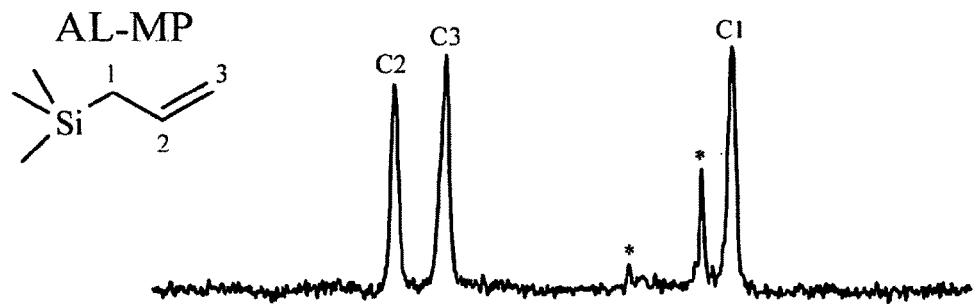
Figure 10H:
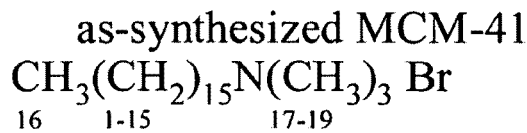
Figure 10H:
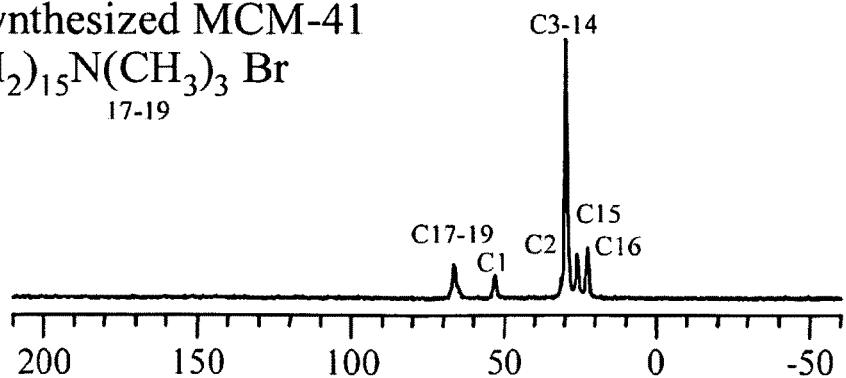

To determine the effect of the mesoporous silica particles of the invention on the $[Ca^{2+}]_i$ of astrocytes under our experimental conditions, enriched type-1 astrocytes were cultured in the presence of the capped mesoporous silica particles without ATP encapsulation. Perfusion application of 100.0 μM ATP only increased the fluorescence intensity ($[Ca^{2+}]_i$ increased) of the areas where the astrocytes are located, whereas the fluorescence intensity of those of capped mesoporous silica particles stayed constant as depicted in the pseudo-color images of the culture before (FIG. 8a) and after (FIG. 8b) the ATP application. This result showed that apparently the astrocytes responded normally to ATP stimulation in the presence of the capped mesoporous silica particles. The culture of astrocytes and the capped mesoporous silica particles was then subjected to the same ME application. As shown in FIGS. 8b and c, no detectable changes in $[Ca^{2+}]_i$ were observed in the areas of astrocytes, but drastic decreases of fluorescence could be noticed easily in those areas of the capped mesoporous silica particles indicating the release of CdS caps upon ME application.

Example 4

Gene Transfection a. Cell Cultures.

Cortical and hippocampal neuronal cultures were prepared as described by Jeremic, A., et al., *J. Neurochem.* 2001, 77, 664-675.

b. Cationic Dendrimer-Capped Mesoporous Silicate.

Gene transfection was accomplished using a poly(amidoamine) dendrimer-capped mesoporous silicate (G2-PAMAM-MSN) carrier system, which was synthesized by the following procedures. A mercaptopropyl-derivatized mesoporous silica nanosphere material (thiol-MSN) was synthesized using a method similar to that described by Lin, V. S.-Y., et al., *J. Am. Chem. Soc.* 2001, 123, 11510-11511; and Lin, V. S.-Y., et al., *J. Am. Chem. Soc.* 2002, 124, 9040-9041. The thiol-MSN's (1.0 g) were dispersed in toluene with another layer of 3-mercaptopropyl group grafted on their exterior surface by introducing 0.189 mL of 3-mercaptopropyl-trimethoxysilane (MPTMS) at a ratio of 1 mmol MPTMS per gram of MSN. The resulting material was extensively washed with methanol. The surfactant template was further removed by acidic extraction in a solution of 7.5% v/v of HCl in methanol. The material was further functionalized with cysteine groups via a disulfide exchange of the thiol-MSN by reaction with 2-thiopyridyl-cystine hydrochloride ($5 \times 10^{-4}$ mol) in methanol. The surface coverage was determined to be $3.6 \times 10^{-4}$ mol cysteine per gram of MSN material. The cysteine-MSN (0.1 g) was first dispersed in a 0.7 mL phosphate buffer solution and added to a solution of G2-PAMAM dendrimer (0.69 mL) in 5% $NaHCO_3$ with 15 mg of EDC (7.2×

$10^{-5}$ mol to obtain the desired G2-PAMAM-MSN. The product was washed with water and methanol and dried under high vacuum.

c. Plasmid DNA Vector for Gene Transfection.

The pEGFP-C1 vector, an enhanced Green Fluorescent Protein (EGFP) vector for mammalian expression, was purchased from BD Biosciences, inc. The concentration of this plasmid DNA was determined by UV spectroscopy.

d. Methods.

A typical complexation experiment of pEGFP-C1 with PAMAM-MSN was performed by the following procedures. First, an aqueous suspension of G2-PAMAM-MSN was prepared by dispersing the MSN particles in neurobasal media (1.5 mg MSN in 0.430 mL media) through several cycles of sonication/vortexing until a fine milky suspension was obtained. Aliquots of 18 μL of the suspension were incubated with different amounts of pEGFP-C1 vector to study the optimum ratio of complexation. The complexation extent was assessed by measuring the amount of DNA in the supernatant after 12 hours incubation by monitoring the fluorescence of EtBr after intercalation with the DNA in the supernatant. Only combinations that did not show any fluorescence increase vis-à-vis EtBr background fluorescence were used for cell transfection. These combinations were electrophoresed to ensure that the complexes are maintaining the excess positive charge necessary for approaching the membrane of cells and further internalization. Final DNA amount that were used in transfection experiments were 1, 2, 3 and 4 μg of pEGFP-C1 complexed with 18 μL of PAMAM-MSN suspension. The combinations correspond to an estimated N/P ratio (positive/negative charge ratio) of 75.5, 37.75, 25.16 and 18.87 respectively. The complex suspension was diluted in neurobasal media to a volume of 100 μL and deposit onto the cells cultures. Intracellular localization of Green Fluorescent Protein in living cells as well as in death cells was performed on a Leica confocal microscopic imaging system. Detection of GFP was carried out using an argon laser having standard FITC filter sets. The cells were imaged using a 60 plan oil immersion objective.

e. Results.

Neurons emitting strong green fluorescence were observed upon photo-excitation (excitation wavelength=488 nm) of the cell cultures after 48 hours of gene transfection as shown in FIG. 8. The result indicated that the neurons were transfected by the DNA-associated PAMAM-MSN gene transfer system. Utilizing MSN as structural template to assemble a large quantity of the G2-PAMAM with low cytotoxicity on a mesoporous silicate surface for DNA complexation circumvents the difficulty of electrostatically recruiting enough G2-PAMAM to bind to one plasmid DNA molecule in homogeneous solution due to the entropy penalty. In addition, this method provides an important alternative to avoid using the conventional high generation cationic dendrimer which are often cytotoxic and cause damages to the targeted cells.

Examples 5 and 6 illustrate the synthesis of intermediate mesoporous silicates that can be capped to provide articles of the invention. In one embodiment, the invention provides the novel intermediate mesoporous silicates described herein. In another embodiment, the invention provides novel synthetic methods described herein for preparing mesoporous silicates. In a particular embodiment, the invention provides synthetic methods for controlling mesoporous silicate particle shape and size as described in Examples 5 and 6.

Example 5

Organic Functionalization and Morphology Control of Mesoporous Silicas via a Co-condensation Synthesis Method Since the discovery of surfactant micelle-templated synthesis of mesoporous silica materials, such as MCM-41/48 (Beck, J. S. et al., *J. Am. Chem. Soc.*, 114, 10834-10843 (1992); Kresge, C. T. et al., *Nature*, 359, 710-712 (1992)), SBA-15 (Zhao, D. et al., *Science*, 279, 548-552 (1998)), MSU-n (Bagshaw, S. A. et al., *Science*, 269, 1242-1244 (1995)), KIT-1 (Ryoo, R. et al., *J. Phys. Chem.*, 100, 17718-17721 (1996)), and FSM-16 (Inagaki, S. et al., *Bull. Chem. Soc. Jpn.*, 69, 1449-1457 (1996)), many research efforts have focused on (i) preparing the organic/inorganic hybrids through functionalization of the exterior and/or interior surfaces and (ii) controlling the particle morphology. The success of such investigations will prompt the utilization of these materials in separation (Dai, S. et al., *Angew. Chem., Int. Ed. Engl.*, 38, 1235-1239 (1999); Lin, Y. et al., *Environ. Sci. Technol.*, 35, 3962-3966 (2001); Yoshitake, H. et al.; *Chem. Mater.*, 15, 1713-1721 (2003); Yoshitake, H. et al., *Bull. Chem. Soc. Jpn.*, 76, 847-852 (2003); Hossain, K. Z. and Mercier, L., *Adv. Mater.*, 14, 1053-1056 (2002)), sensor design (Lin, V. S. Y. et al., *J. Am. Chem. Soc.*, 123, 11510-11511 (2001); Burleigh, M. C. et al., *Chem. Mater.*, 13, 2537-2546 (2001)), catalysis (Soler-Illia Galo, J. d. A. A. et al., *Chem. Rev.*, 102, 4093-4138 (2002); Stein, A. *Adv. Mater.*, 15, 763-775 (2003); Davis, M. E. Nature, 417, 813-821 (2002); Conna, A. *Chem. Rev.*, 97, 2373-2419 (1997); Price, P. M. et al., *Dalton*, 101-110 (2000); Ying, J. Y. et al., *Angew. Chem., Int. Ed. Engl.*, 38, 56-77 (1999); Sayari, A. *Chem. Mater.*, 8, 1840-1852 (1996); Moller, K. and Bein, T., *Chem. Mater.*, 10, 2950-2963 (1998)), and drug delivery (Lai, C.-Y. et al., *J. Am. Chem. Soc.*, 125, 4451-4459 (2003)).

Although numerous synthetic approaches have been pursued and significant progress has been made in functionalization of MCM silicas with various organic groups, the current state-of-the-art methods, such as post synthesis grafting (Liu, J. et al., *J. Phys. Chem. A*, 104, 8328-8339 (2000)) and *organosiloxane/siloxane co-condensation* (Stein, A. et al. *Adv. Mater.*, 12, 1403-1419 (2000)), need to be improved in order to control the amount and location of the incorporated functional groups. For example, the post synthesis grafting method typically results in inhomogeneous surface coverage because the introduced organic moieties congregate near the entries to the mesoporous channels and on the exterior surfaces (Lim, M. H. and Stein, A., *Chem. Mater.*, 11, 3285-3295 (1999)). While many organically functionalized mesoporous materials have been prepared via co-condensation (Lim, M. H. and Stein, A., *Chem. Mater.*, 11, 3285-3295 (1999); Fowler, C. E. et al., *Adv. Mater.*, 13, 649-652 (2001); MacLachlan, M. J. et al., *Chem.-Eur. J.*, 6, 2507-2511 (2000); Fowler, C. E. et al., *Chem. Commun.*, 1769-1770 (1997); Fowler, C. E. et al., *Chem. Commun.*, 1825-1826 (1998); Hall, S. R. et al., *Chem. Commun.*, 201-202 (1999); Zub, Y. L. et al., *Mendeleev Commun.*, 208-210 (2001); Lim, M. H. et al., *Chem. Mater.*, 10, 467-470 (1998); Lim, M. H. et al., *J. Am. Chem. Soc.*, 119, 4090-4091 (1997); Babonneau, F. et al., *J. Mater. Chem.*, 9, 175-178 (1999); Moller, K. et al., *Chem. Mater.*, 11, 665-673 (1999); Sayari, A. and Hamoudi, S., *Chem. Mater.*, 13, 3151-3168 (2001); Inagaki, S. et al., *Nature*, 416, 304-307 (2002); Burleigh, M. C. et al., *J. Phys.*

Chem. B, 105, 9935-9942 (2001); Burleigh, M. C. et al., Chem. Mater., 13, 4760-4766 (2001), only few very recent investigations reported that spherical or tubular MCM-41 type silicas could be synthesized via incorporation of either mercaptopropyl, allyl, or aminopropyl functional groups (Sadasivan, S. et al., J. Mater. Chem., 13, 1023-1029 (2003)). Also, the previously reported co-condensation methods usually result in breakup of the structural integrity and long-range periodicity at surface coverages exceeding 25%.

A new synthetic method has been discovered that combines efficient organic functionalization of mesoporous silicas with control of particle morphology. The degree of functionalization and particle morphology are dictated by the concentration, molecular size and hydrophilicity/hydrophobicity of the organoalkoxysilane precursors. Mesoporous silicates were prepared using a co-condensation method based on sodium hydroxide-catalyzed reactions of tetraethoxysilane (TEOS) with various organoalkoxysilanes in the presence of a low concentration of cetyltrimethylammonium bromide (CTAB) surfactant. The organoalkoxysilanes included 3-aminopropyltrimethoxysilane (APTMS), N-(2-aminoethyl)-3-aminopropyltrimethoxysilane (AAPTMS), 3-[2-(2-aminoethylamino)ethylamino]propyl-trimethoxysilane (AEPTMS), ureidopropyltrimethoxysilane (UDPTMS), 3-isocyanatopropyltriethoxy-silane (ICPTES), 3-cyanopropyltriethoxysilane (CPTES), and allyltrimethoxysilane (ALTMS). In contrast to the Stöber process (Stoeber, W. et al., J. Colloid Interface Sci., 26, 62-69 (1968)) or the recently reported controlled quenching method (Sadasivan, S. et al., J. Mater. Chem., 13, 1023-1029 (2003), no organic co-solvents or instantaneous neutralization of alkaline solutions were required during the co-condensation reactions. By systematically varying the type and the amount of organoalkoxysilanes, a series of nanoparticles was obtained in form of spheres, rods, and hexagonal tubes. Hereinbelow, these materials are referred to as X-MP, where X describes the organoalkoxysilane precursor and MP stands for mesoporous particle. To examine the different mechanistic effects of the organoalkoxysilane-induced shape transformation, the structures of these mesoporous organic/inorganic hybrid materials were examined by powder X-ray diffraction (XRD) spectroscopy, field-emission scanning electron microscopy (FE-SEM), nitrogen adsorption-desorption surface analysis (BET isotherms and BJH pore size distributions), and thermogravimetric analysis (TGA). The incorporation of the organic functional groups was quantitatively studied by solid state NMR spectroscopy of $^{13}C$ and $^{29}Si$. Based on the observations of the morphological structures and the degree of organic functionalization, it appears that the formation of the mesoporous silica nanoparticles depends on the interaction between organoalkoxysilanes and CTAB micelles.

Experimental

The organoalkoxysilane precursors used for our co-condensation reactions contain a common trimethoxysilyl or triethoxysilyl terminal group and different organic functional groups, as depicted in Scheme 1. APTMS, AAPTMS, AEPTMS, UDPTMS, ICPTES, CPTES, ALTMS, TEOS and CTAB were purchased from Aldrich and used as received. The reaction mixture contained 1.0 CTAB: 8.16 TEOS: 1.05 organotrialkoxysilane of choice (unless specified otherwise): 2.55 NaOH: 4857$H_2O$ based on the molar ratio. For example, in the case of AP-MP, the mixture of CTAB (2.0 g, 5.49 mmol), 2.0 M of NaOH(aq) (7.0 mL, 14.0 mmol) and $H_2O$ (480 g, 26.67 mol) was heated at 80° C. for 30 min to reach pH 12.3. To this clear solution, TEOS (9.34 g, 44.8 mmol) and APTMS (1.03 g, 5.75 mmol) were added sequentially and rapidly via injection. Following the injection, a white precipitation was observed after 3 minutes of stirring at ca. 550 rpm. The reaction temperature was maintained at 80° C. for 2 hours, then quenched by cooling the solution to room temperature. The products were isolated by filtration, washed with copious amount of water and methanol and dried under vacuum. The reaction yields of as-made products varied with respect to the choice of organoalkoxysilane and ranged from 38% to 65% of the starting weight of TEOS. An acid extraction was performed in methanol (100 mL) mixture of concentrated hydrochloric acid (1.0 mL) and as-made materials (1.0 g) at 60° C. for 6 hours. Resulting surfactant-removed solid products were filtered and washed with water and methanol and then dried under vacuum. Pure MCM-41 samples were prepared as reference using the same experimental conditions. The as-synthesized sample containing the surfactant is referred to as s-MCM-41, while the sample with CTAB removed is denoted as MCM-41.

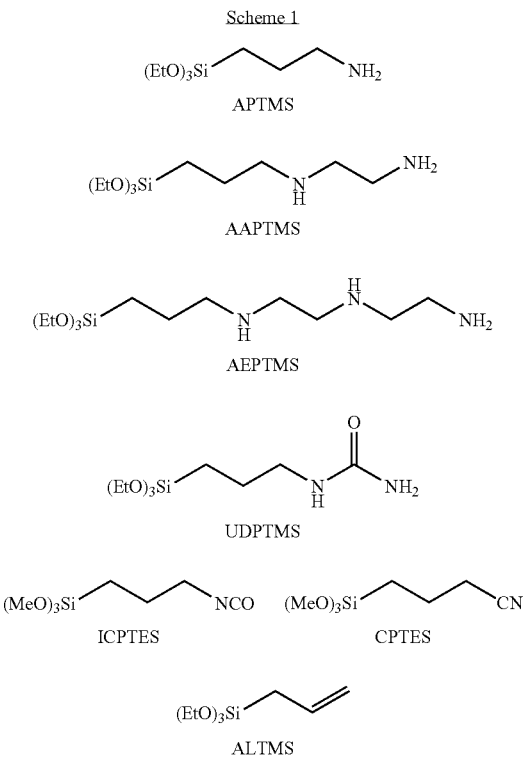

Scheme 1

Particle morphology was determined by scanning electron microscopy (SEM) using a Hitachi S4700 FE-SEM system with 10 kV accelerating voltage and 0.005 nA of beam current for imaging. For transmission electron microscopy (TEM) studies, a small aliquot was taken from a suspension of methanol and placed in a lacey carbon coat TEM grid, which was pulled through the suspension and allowed to dry in air. Thin sections of samples embedded in epoxide were obtained with ultramicrotomy (60-80 nm). The resulting sample was examined with a Philips model CM-30 TEM operated at 300 kV. The specimen was given no further treatment, as it appeared stable under beam bombardment.

Powder XRD experiments were performed on a Scintag XDS 2000 diffractometer using a Cu Kα radiation source. Low angle diffraction with a 2θ range of 1.0-10° was used to investigate the long-range order of the materials. The surface area and median pore diameter were measured using $N_2$ adsorption/-desorption measurements in a Micromeritics ASAP 2000 BET surface analyzer system. The data were evaluated using the Brunauer-Emmett-Teller (BET) and Barrett-Joyner-Halenda (BJH) methods to calculate the surface area and pore volumes/pore size distributions, respectively. Samples were prepared by degassing at 90° C. for 1 hour and then at 150° C. for 4 hours. TGA curves were recorded using a TA Instruments TGA 2950 thermogravimetric analyzer with a temperature ramp of 5° C./min under continuous flow of nitrogen (100 mL/min).

Solid-state nuclear magnetic resonance (NMR) experiments were performed on a Varian/Chemagnetics Infinity spectrometer at the frequencies of 79.5, 100.6 and 400.0 MHz for $^{29}Si$, $^{13}C$ and $^1H$ nuclei, respectively. $^{13}C$ and $^{29}Si$ nuclei were observed using direct polarization (DP) or by cross polarization (Pines, A. et al., *J. Chem. Phys.*, 59, 569-590 (1973)) (CP) from the neighboring $^1H$ nuclei. The samples were placed in 5 mm zirconia rotors and spun at 10 kHz in a doubly tuned Chemagnetics probe. The saturation recovery experiment, carried out for AL-MP and ICP-MP samples, yielded the $^{29}Si$ longitudinal relaxation times in the range 30~65 s. In spite of slow relaxation, $^{29}Si$ DPMAS measurements were performed to obtain quantitative spectra for all samples. These experiments used excitation with a single 90° pulse of 2.1 μs followed by data acquisition under continuous wave (CW) $^1H$ decoupling at 65 kHz. Typically 270 scans were completed using pulse delay of 300 s.

The variable amplitude CPMAS scheme (Peersen, O. B. et al., *J. Magn. Reson. A*, 104, 334-339 (1993)) was used to enhance the polarization of observed nuclei and increase the repetition rate of data acquisition. During each cross polarization period, the $^1H$ rf field was ramped between 16 and 40 kHz using 2.4 kHz increments, whereas the $^{29}Si$ (or $^{13}C$) rf field was maintained at a constant level of approximately 36 kHz. The maximum $^1H \rightarrow ^{29}Si$ polarization transfer was achieved using a contact time of approximately 10 ms, which is in agreement with previous studies performed for silicas (Maciel, G. E. and Sindorf, D. W., *J. Am. Chem. Soc.*, 102, 7606-7607 (1980)). For $^{13}C$ nuclei, shorter contact times of 0.4~1.5 ms were used. The $^1H$ rf magnetic fields of 90 kHz and 65 kHz were used for initial excitation and decoupling, respectively. The values of $^1H$ longitudinal relaxation time encountered in all mesoporous samples examined in this study did not exceed 1 s, which allowed for repetition time of 1.2 s to be used in the CPMAS experiments. Typically, 4K scans were accumulated for $^1H \rightarrow ^{29}Si$ CPMAS, whereas $^1H \rightarrow ^{13}C$ experiments required between 1K and 10K scans per spectrum. All chemical shifts were referenced to $SiMe_4$.

Results and Discussion

Organic functionalization. To simplify the analysis, a series of samples was prepared in which the amount of organoalkoxysilane used for the preparation was fixed at 12.8 mol % of the amount of TEOS. The $^1H \rightarrow ^{13}C$ CPMAS spectra of these samples, shown in FIG. 10, provide clear evidence that they were indeed functionalized as intended. The observed chemical shifts, listed in Table 1, agree well with those observed in homogeneous solutions of the corresponding precursors.

TABLE 1

$^{13}C$ chemical shifts ($\delta_C$, in ppm from TMS) of organic groups obtained from $^1H \rightarrow ^{13}C$ CPMAS spectra.

| AP-MP | | AAP-MP | | AEP-MP | | UDP-MP | | ICP-MP | | CP-MP | | AL-MP | | s-MCM-41 | |
|---|---|---|---|---|---|---|---|---|---|---|---|---|---|---|---|
| | $\delta_C$ | | $\delta_C$ | | $\delta_C$ | | $\delta_C$ | | $\delta_C$ | | $\delta_C$ | | $\delta_C$ | | $\delta_C$ |
| C1 | 9.1 | C1 | 8.5 | C1 | 8.7 | C1 | 9.0 | C1 | 8.8 | C1 | 10.5 | C1 | 18.8 | C16 | 22.7 |
| C2 | 20.6 | C2 | 19.8 | C2 | 19.4 | C2 | 23.1 | C2 | 20.7 | C2 | 18.3 | C2 | 130.8 | C15 | 26.1 |
| C3 | 42.3 | C3 | 37.2 | C3 | 38.5 | C3 | 42.9 | C3 | 42.2 | C3 | 18.3 | C3 | 114.2 | C3-14 | 29.8 |
| | | C5[a] | 49.8 | C5[b] | 49.1 | C5 | 162.2 | C5 | 160.4 | C4 | 118.4 | | | C2 | 31.8 |
| | | C6[a] | 45.0 | C6[b] | 44.5 | | | | | | | | | C1 | 66.4 |
| | | | | C8[c] | 56.1 | | | | | | | | | $NCH_3$ | 53.4 |
| | | | | C9[c] | 52.2 | | | | | | | | | | |

[a],[b],[c]The assignments are somewhat ambiguous for these three pairs of carbons (they may be reversed).

Figure 11:
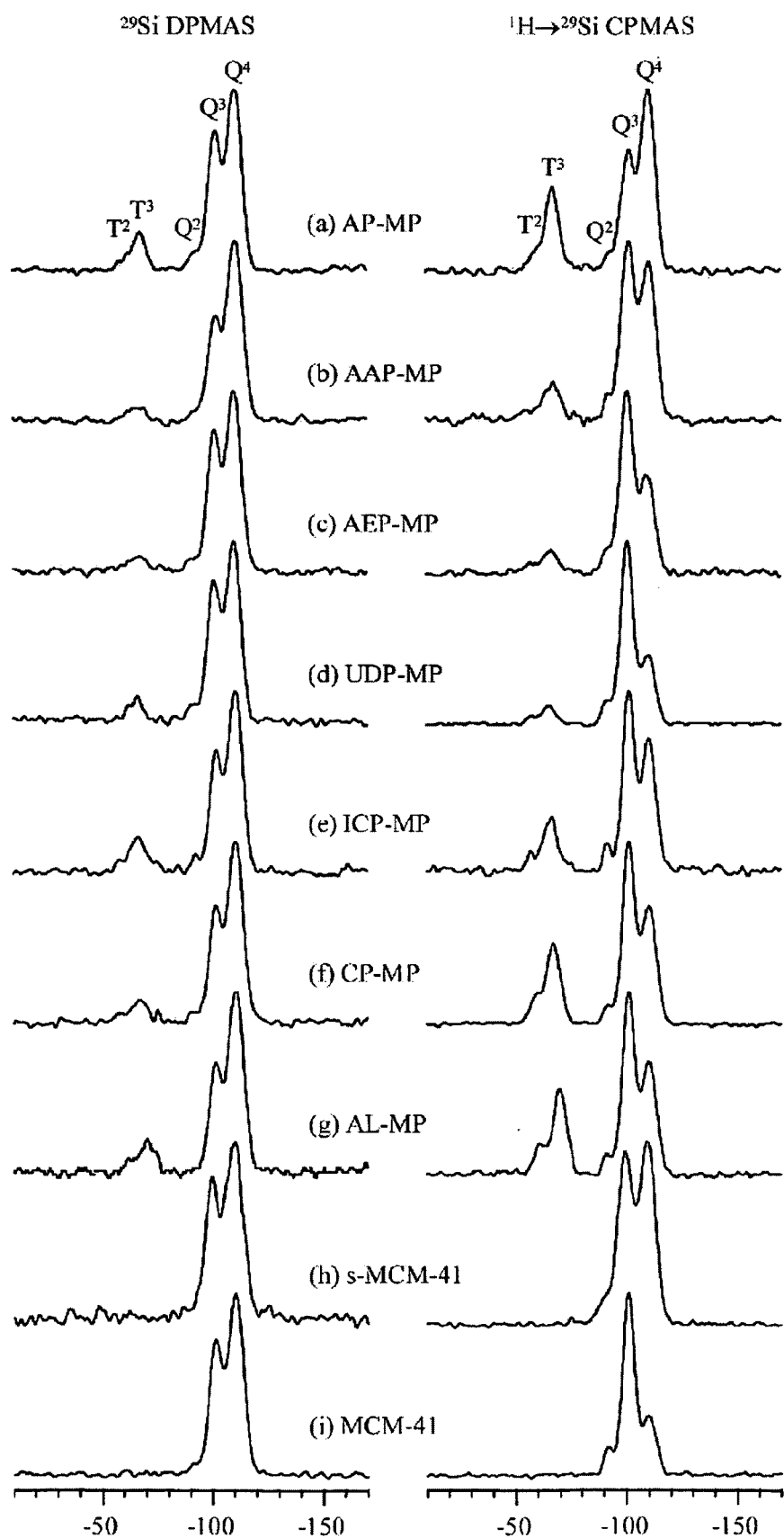
FIG. 11 $^{29}Si$ DPMAS (left) and $^1H\rightarrow^{29}Si$ CPMAS (right) spectra of AP-MP (a), AAP-MP (b), AEP-MP (c), UDP-MP (d), ICP-MP (e), CP-MP (f), AL-MP (g), s-MCM-41 (h), and MCM-41 after the extraction of surfactant (i).
Figure 13A:
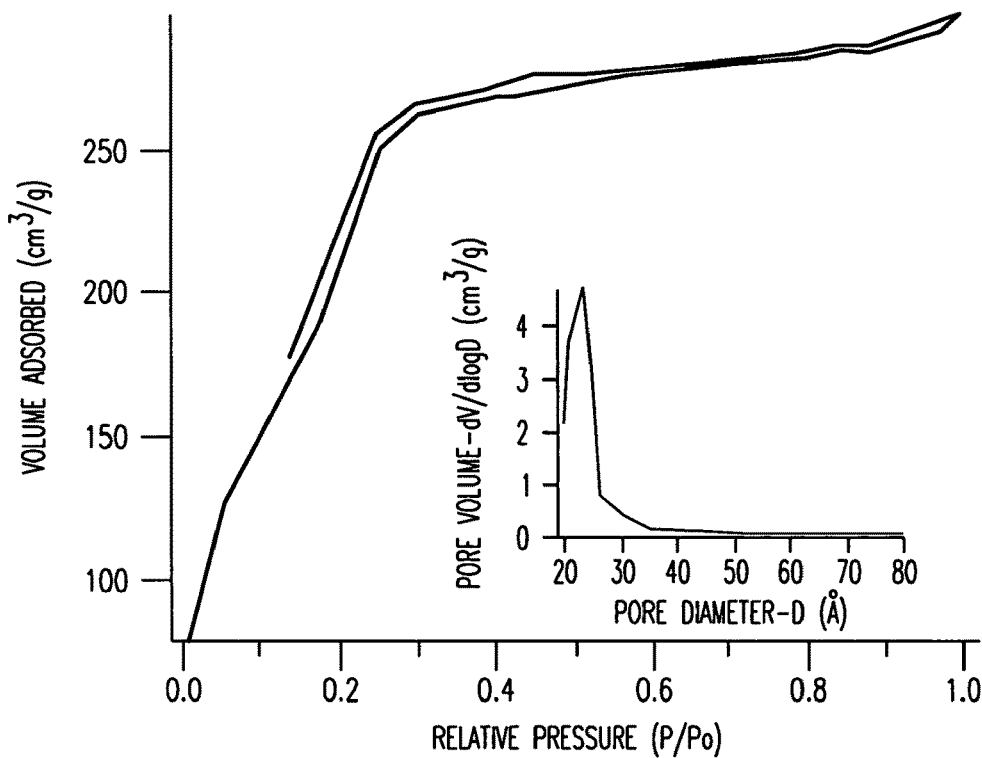
FIG. 13 BET isotherms and BJH pore size distributions (insets) of AP-MP (a), AAP-MP (b), AEP-MP (c), UDP-MP (d), ICP-MP (e), CP-MP (f), AL-MP (g) and pure MCM-41 silica (h) materials.
Figure 13B:
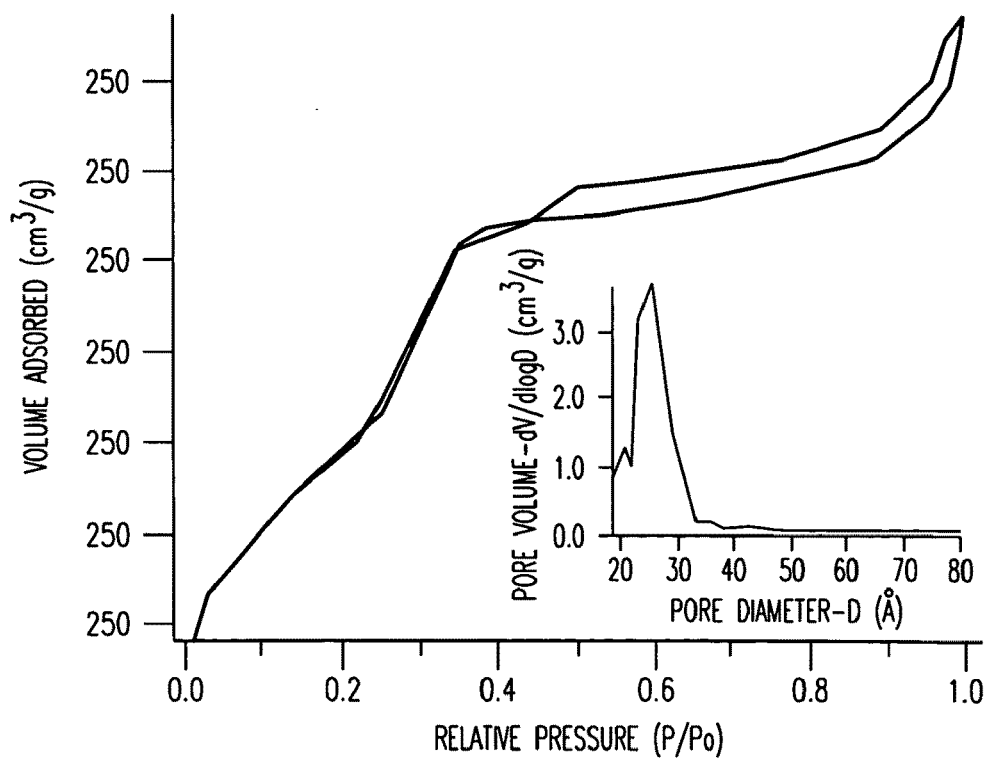
Figure 13C:
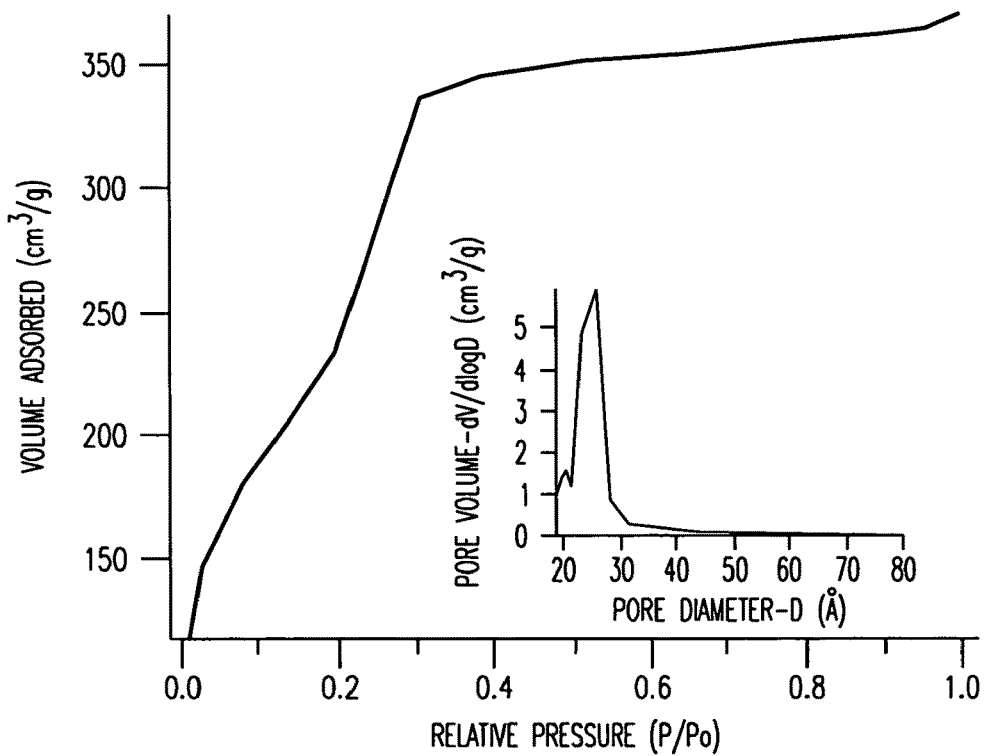
Figure 13D:
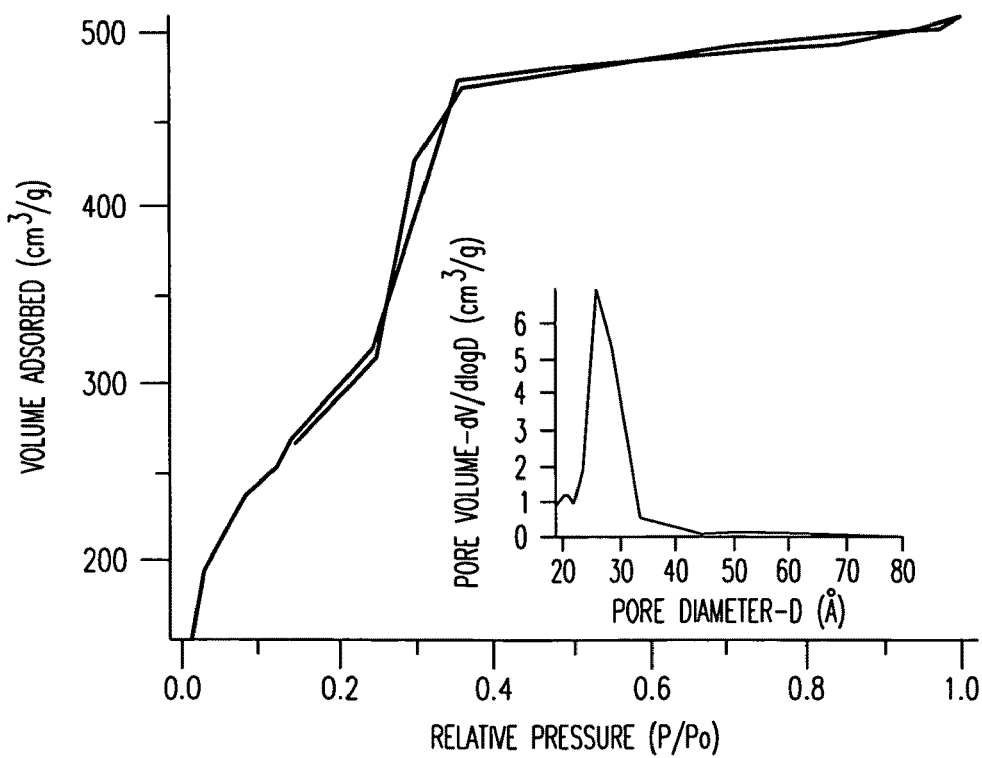
Figure 13E:
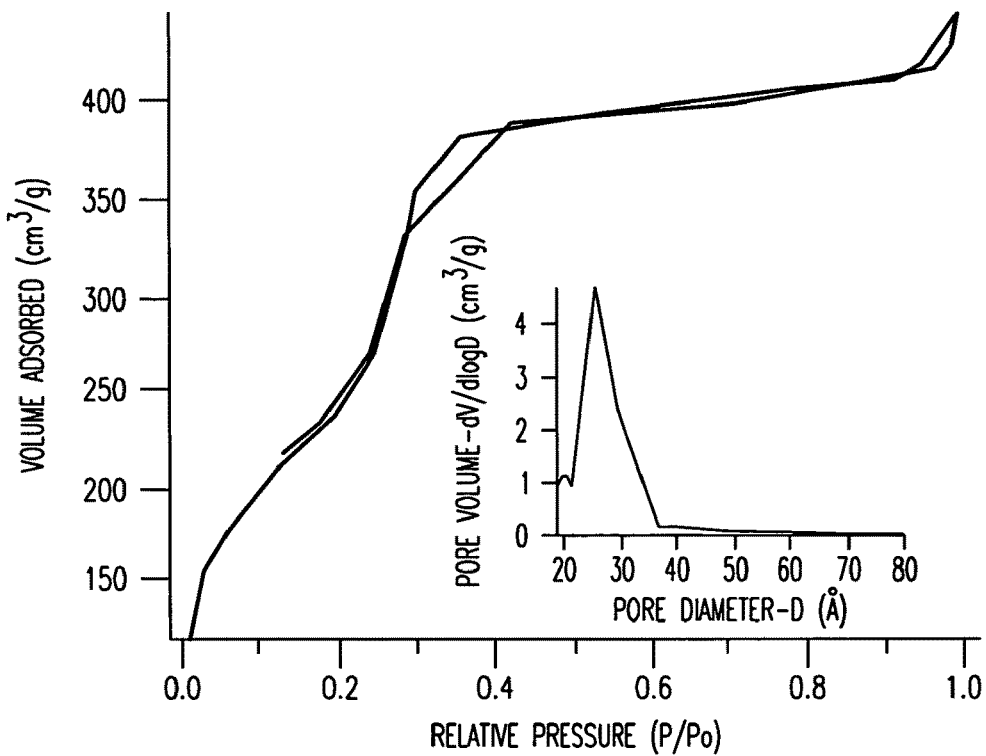
Figure 13F:
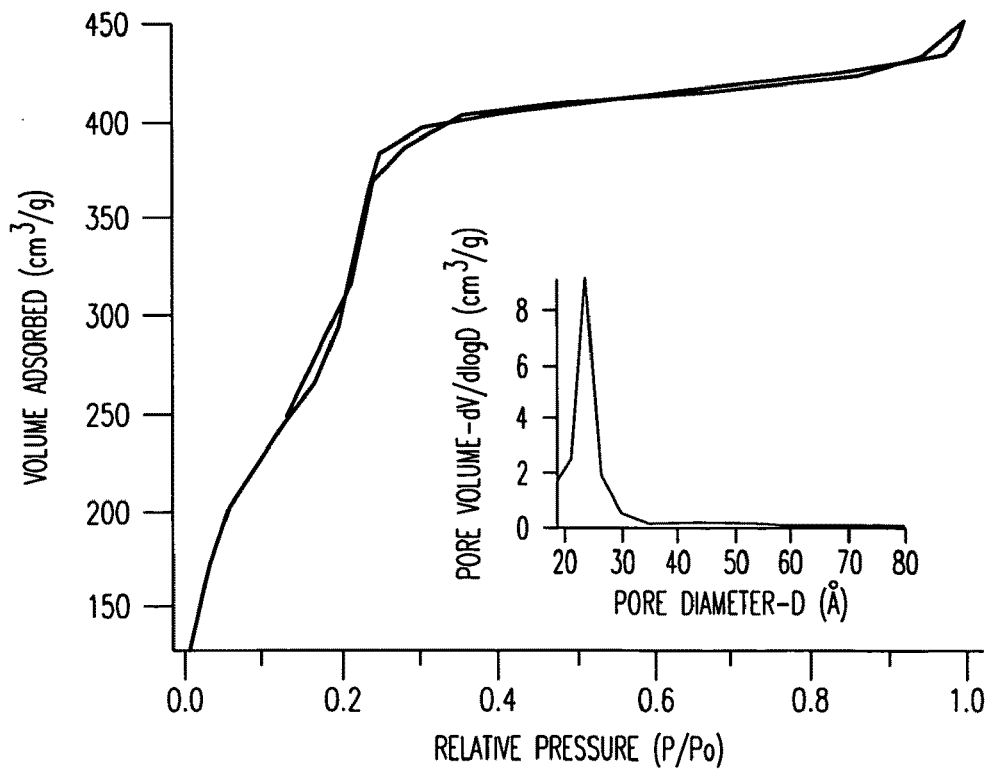
Figure 13G:
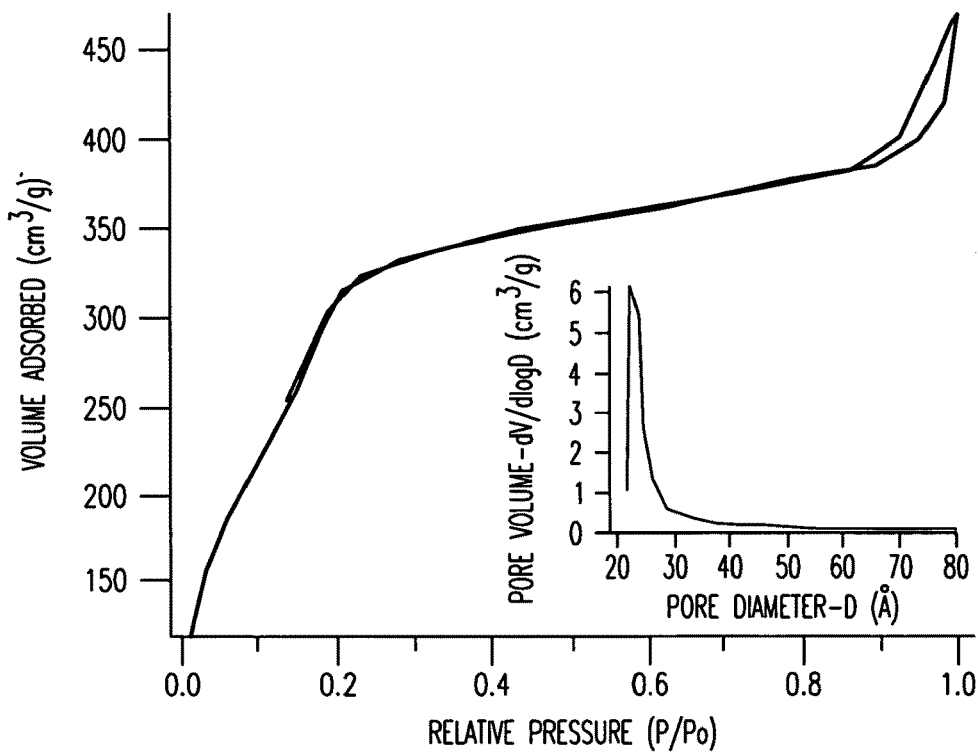
Figure 13H:
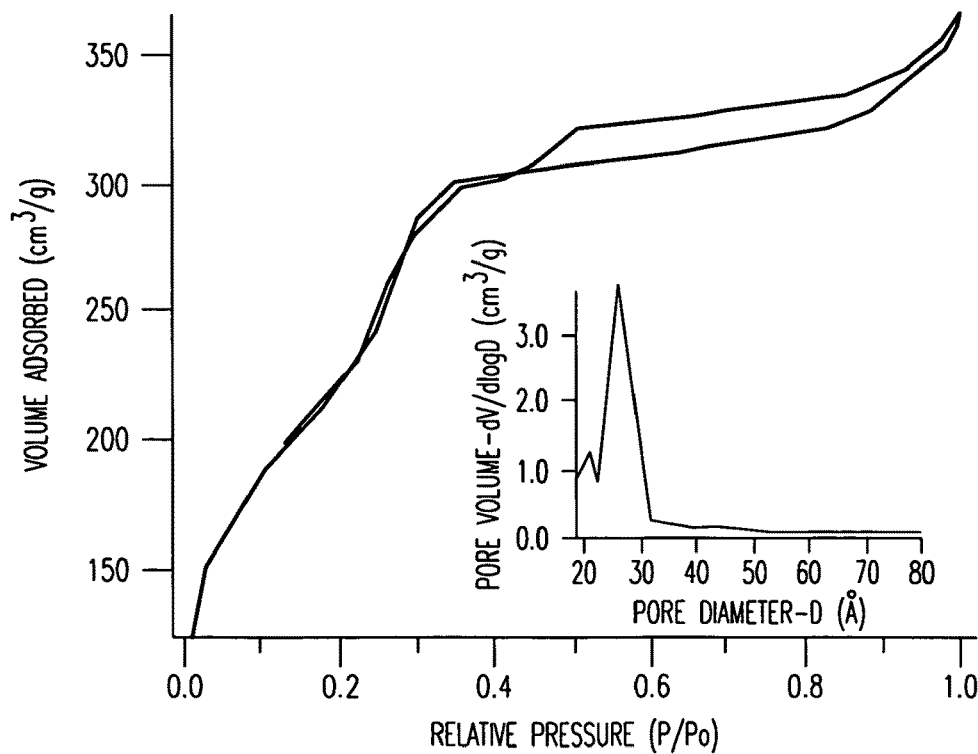

For example, the resonances at 6.5, and 45.3 ppm in the spectrum of APTMS dissolved in $CDCl_3$ (not shown) corresponded to those at 9.1 ppm (C1) and 42.3 ppm (C3) observed in AP-MP. The resonance at 28 ppm representing C2 exhibited a larger shift change toward higher field relative to the liquid state (20.6 ppm). The CPMAS spectrum of s-MCM-41 sample (FIG. 10h) consisted of several resonances due to CTAB, among which the peak at around 30 ppm, corresponding to carbons C3 through C14, is most intense. Two samples, CP-MP and AL-MP, contained detectable resonances from CTAB (marked with asterisks in spectra f and g), which comprised just a few % of the total $^{13}C$ intensity. The functionalization of silicas was further studied by TGA and solid state NMR of $^{29}Si$ (FIG. 11 and Table 2). In general, three or four distinct weight loss TGA profiles were found, including methanol, organic functional groups, and a small weight loss due to the dehydration of the surface hydroxyl groups. While the TGA data provided evidence of the existence of organic functional groups inside the pores, a direct, quantitative measure of the organic functionalization was provided by $^{29}Si$ DPMAS spectra shown in the left column of FIG. 11. The resonances at around −59 and −68 ppm represented silicon atoms in positions ($\equiv SiO)_2Si(OH)R$ and ($\equiv SiO)_3SiR$, which are denoted $T^2$ and $T^3$, respectively (Maciel, G. E. et al., *Encyclopedia of Nuclear Magnetic Resonance*, 7, 4370-4386 (1996); Engelhardt, G. and Michel, D., *High-Resolution Solid-State NMR of Silicates and Zeolites*, John Wiley & Sons: Chichester (1987); Lindner, E. et al., *Angew. Chem., Int. Ed. Engl.*, 38, 2155-2174 (1999)). These silicon species were better observed using the $^{29}Si$ CP-MAS NMR method (see FIG. 11, right column), which detected only the nuclei located within 2-3 bond lengths from the nearest hydrogen atoms. Note that the presence of $T^3$ and $T^2$ functionalities confirmed the existence of the covalent linkage between the organic groups and the silica surface. The resonance lines representing $Q^4$ (siloxane, ($\equiv SiO)_4Si$), $Q^3$ (single silanol, ($\equiv SiO)_3SiOH$) and $Q^2$ (geminal silanol, ($\equiv SiO)_2Si(OH)_2$) silicons were also observed in their usual spectral positions (Maciel, G. E. et al., *Encyclopedia of Nuclear Magnetic Resonance*, 7, 4370-4386 (1996); Engelhardt, G. and Michel, D., *High-Resolution Solid-State NMR of Silicates and Zeolites*, John Wiley & Sons: Chichester (1987); Lindner, E. et al., *Angew. Chem., Int. Ed. Engl,* 38, 2155-2174 (1999)). The relative concentrations of all silicon sites were obtained by deconvolution of DPMAS spectra (see Table 2). Assuming that all $Q^3$ and $Q^2$ sites decorated the interior walls of mesoporous silicas, the surface coverage (SC) of the mesopores with organic moieties could be estimated as $SC=(T^2+T^3)/(Q^2+Q^3+T^2+T^3)$. As shown in Table 2, the SC values varied between 13% for UDP-MP and 33% for AL-MP. The measured loading efficiencies of the MP's synthesized with the organoalkoxysilanes containing hydrophobic functional groups, such as CPTES and ALTMS, were higher than those that contained the hydrophilic precursors, such as AAPTMS and AEPTMS. These results suggested that the organoalkoxysilanes with hydrophobic functional groups could better orient themselves around the water/micelle interface and intercalate these groups to the hydrophobic regions of the CTAB micelles during the co-condensation reactions.

AL-MP (500 nm and 50 nm, respectively). As a rule, the particle sizes of materials prepared with the hydrophobic organoalkoxysilane precursors, such as ICPTES, CPTES, and ALTMS, appear significantly smaller than pure MCM-41 (FIG. 12h), whereas the materials synthesized using more hydrophilic organoalkoxysilanes, such as AAPTMS, AEPTMS, and UDPTMS, yielded larger particles. Note that the co-condensation reactions took place in a basic aqueous solution (pH=12.3), therefore the trialkoxysilyl groups of these organoalkoxysilanes were hydrolyzed and converted to the trihydroxysilyl group, which is hydrophilic. The other end of the molecule can be either hydrophilic or hydrophobic depending on the water solubility of the organic functional group involved.

The surface areas, pore volumes and pore size distributions of the MP materials were analyzed by the nitrogen adsorption-desorption techniques. As shown in FIG. 13, all silicas exhibited characteristic Type IV BET isotherms consistent with the presence of cylindrical meso-scale pores. However, as outlined in Table 3, the BJH average pore diameters were different depending on the types of the incorporated organic

TABLE 2

$^{29}$Si chemical shifts ($\delta_{Si}$, in ppm from TMS) and relative concentrations of T$^n$ and Q$^n$ groups obtained from $^{29}$Si DPMAS spectra.

|  | AP-MP | | AAP-MP | | AEP-MP | | UDP-MP | | ICP-MP | | CP-MP | | AL-MP | | s-MCM-41 | | MCM-41 | |
|---|---|---|---|---|---|---|---|---|---|---|---|---|---|---|---|---|---|---|
|  | $\delta_{Si}$ | % | $\delta_{Si}$ | % | $\delta_{Si}$ | % | $\delta_{Si}$ | % | $\delta_{Si}$ | % | $\delta_{Si}$ | % | $\delta_{Si}$ | % | $\delta_{Si}$ | % | $\delta_{Si}$ | % |
| $T^2$ | −59 | 4 | −65 | 4 | −56 | 1 | −62 | 2 | −57 | 1 | −58 | 2 | −64 | 3 | | | | |
| $T^3$ | −68 | 8 | −69 | 1 | −67 | 6 | −66 | 4 | −66 | 13 | −67 | 8 | −71 | 8 | | | | |
| $Q^2$ | −93 | 3 | −94 | 3 | −91 | 3 | −91 | 4 | −92 | 3 | −92 | 2 | −97 | 1 | −93 | 2 | −92 | 3 |
| $Q^3$ | −102 | 26 | −101 | 28 | −101 | 35 | −101 | 38 | −102 | 29 | −101 | 29 | −101 | 24 | −99 | 34 | −101 | 37 |
| $Q^4$ | −111 | 59 | −111 | 64 | −110 | 55 | −110 | 52 | −111 | 54 | −111 | 59 | −111 | 64 | −110 | 64 | −110 | 60 |
| $T_{surf}$ | | 29 | | 14 | | 16 | | 13 | | 30 | | 24 | | 33 | | | | |

Figure 14A:
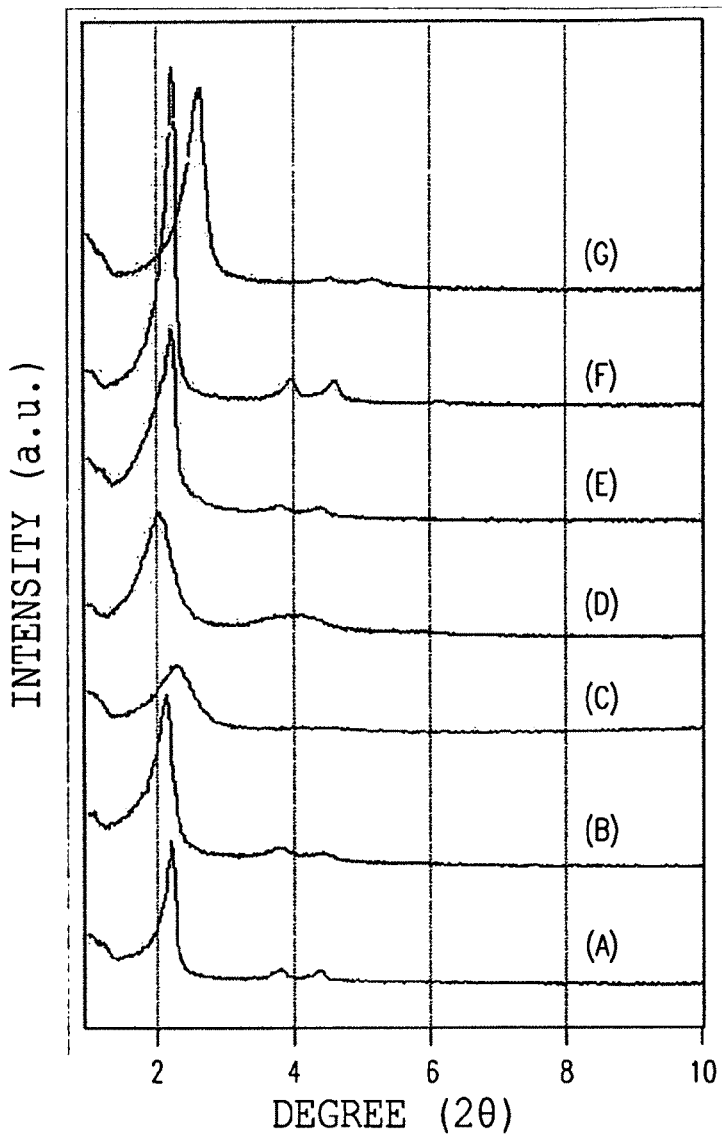
FIG. 14 XRD spectra of the surfactant-removed AP-MP (a), AAP-MP (b), AEP-MP (c), UDP-MP (d), AL-MP (e), CP-MP (f) and ICP-MP (g).
Figure 14B:
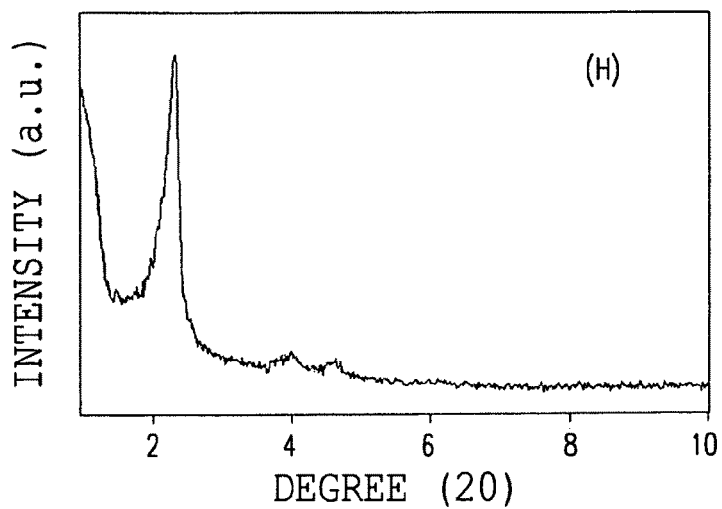

Morphology control. The morphology and mesoporous structure of the organically functionalized MP materials were studied using FE-SEM and powder X-ray diffraction. The FE-SEM micrographs demonstrated a variety of particle shapes and sizes. For example, the AP-MP material showed a curved hexagonal shaped tubular morphology, as depicted in FIG. 12a. Interestingly, upon replacing the APTMS with other structurally similar organoalkoxysilanes, such as AAPTMS and AEPTMS (FIGS. 12b, c), the shapes transformed into twisted columns and micrometer-sized spheres, respectively. In contrast to smooth particle surface of AEP-MP, UDP-MP (FIG. 12d) exhibited micron-sized spherical particles with raspberry-like bumpy rough surfaces. The ICP-MP material (FIG. 12e) consisted of smallest spherical particles with diameters ranging from 100 to 500 nm. In the synthesis of CP-MP (FIG. 12f) and AL-MP materials (FIG. 12g), hexagonal rod-shaped particles of different lengths and diameters were observed. The average particle size of CP-MP (1 μm in length and 500 nm in diameter) is larger than that of functional groups. Again, utilization of the hydrophobic precursors yielded smaller pores. The powder XRD spectra of these materials (FIG. 14) featured an intense (100) reflection peak corresponding to lattice spacings in the range of 33.7 to 43.7 Å. Even though (210) peaks were not observed, the well resolved diffraction patterns characteristic of hexagonal MCM-41 silicas (Gulik, A. et al., *J. de Physique II,* 5, 445-464 (1995)), including (100), (110), and (200) peaks with the spacing ratio of $1:\sqrt{3}:\sqrt{4}$ were observed in AP-MP, AAP-MP, CP-MP, ICP-MP and AL-MP. On the other hand, AEP-MP and UDP-MP (FIGS. 14c, d) appeared to be disordered as evidenced by a broad peak at 4.52° and 4.10°, respectively, representing superimposed (110), and (200) patterns. The TEM micrographs of these samples shown in FIGS. 15a and 15d are consistent with this observation. In contrast, the TEM micrographs of materials prepared with hydrophobic organoalkoxysilanes, such as CPTES, showed well-organized mesopores packed in hexagonal symmetry as evidenced in FIGS. 15b and 15c.

TABLE 3

Structural properties of the organically functionalized mesoporous silica materials.

| Sample | $D_{100}$ (Å)[a] | $a_0$ (Å)[a] | $S_{BET}$ (m$^2$/g)[a] | $V_p$ (cm$^3$/g)[a] | $W_{BJH}$ (Å)[a] | $d_{pore\,wall}$ (Å)[a] | Amount of organic groups (mmol/g)[b] |
|---|---|---|---|---|---|---|---|
| AP-MP | 39.8 | 46.0 | 721.7 | 0.45 | 23.7 | 22.3 | 1.7 |
| AAP-MP | 41.3 | 47.7 | 664.6 | 0.48 | 25.9 | 21.8 | 0.7 |

TABLE 3-continued

Structural properties of the organically functionalized mesoporous silica materials.

| Sample | $D_{100}$ (Å)[a] | $a_0$ (Å)[a] | $S_{BET}$ (m²/g)[a] | $V_p$ (cm³/g)[a] | $W_{BJH}$ (Å)[a] | $d_{pore\,wall}$ (Å)[a] | Amount of organic groups (mmol/g)[b] |
|---|---|---|---|---|---|---|---|
| AEP-MP | 38.4 | 44.4 | 805.8 | 0.57 | 26.0 | 18.4 | 1.0 |
| UDP-MP | 43.7 | 50.5 | 1022.4 | 0.78 | 28.6 | 21.9 | 0.9 |
| ICP-MP | 39.8 | 46.0 | 840.1 | 0.66 | 25.8 | 20.2 | 1.5 |
| CP-MP | 39.4 | 45.5 | 1012.5 | 0.68 | 23.5 | 22.0 | 1.4 |
| AL-MP | 33.7 | 38.9 | 1080.5 | 0.65 | 19.7 | 19.2 | 1.7 |
| MCM-41 | 38.1 | 44.0 | 767.1 | 0.55 | 25.5 | 18.5 | — |

[a]The BET surface area ($S_{BET}$), the mesopore volume ($V_p$), and the mean mesopore width ($W_{BJH}$) were obtained from the nitrogen adsorption/desorption data. The $d_{100}$ numbers represent the d-spacing corresponding to the main (100) XRD peak. The unit cell size ($a_0$) is calculated from the $d_{100}$ data using the formula $a_0 = 2d_{100}/3^{1/2}$. The pore wall thickness $d_{pore\,wall} = a_0 - W_{BJH}$.
[b]The amounts of organic functional groups incorporated to the silica materials were estimated from the $^{29}Si$ DPMAS.

Mechanism responsible for the shape formation. Similar organic precursors can yield very different particle morphologies, e.g., AAP-MP showed tubular-shaped particles (FIG. 12b) while the AEP-MP exhibited exclusively spherical particles (FIG. 12c). Clearly, several different interactions, such as electrostatic attraction/repulsion, hydrogen bonding, and hydrophobic interaction, between the organoalkoxysilanes and surfactant molecules at the micelle/water interface contribute cooperatively to the observed drastic changes in particle morphology. IN order to deconvolute some of these factors, the effect of the concentration of a selected organoalkoxysilane (AEPTMS) on the resulting particle shape and size was investigated.

Figure 16A:
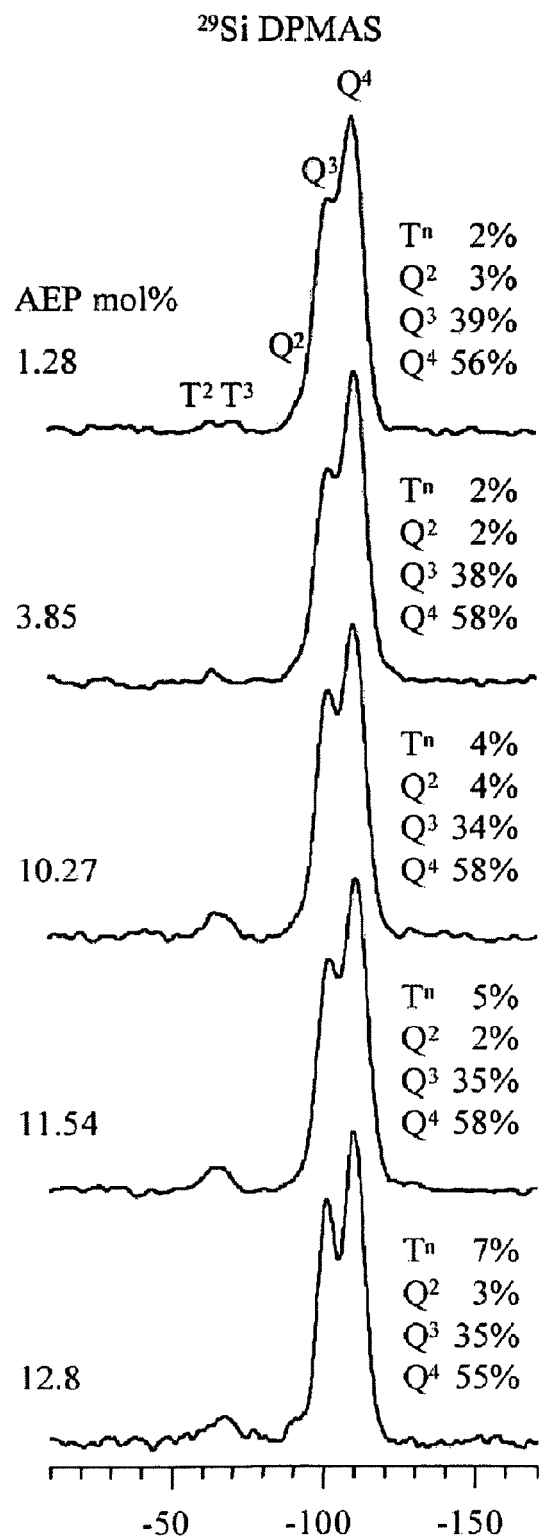
FIG. 16 $^{29}Si$ DPMAS (a) and $^1H\rightarrow^{29}Si$ CPMAS (b) spectra of functionalized mesoporous materials with various amounts of AEPTMS. A contact time of 1 ms was used during cross polarization period. (c) The relative increase of functionalization versus the concentration of AEPTMS estimated from CPMAS.
Figure 16B:
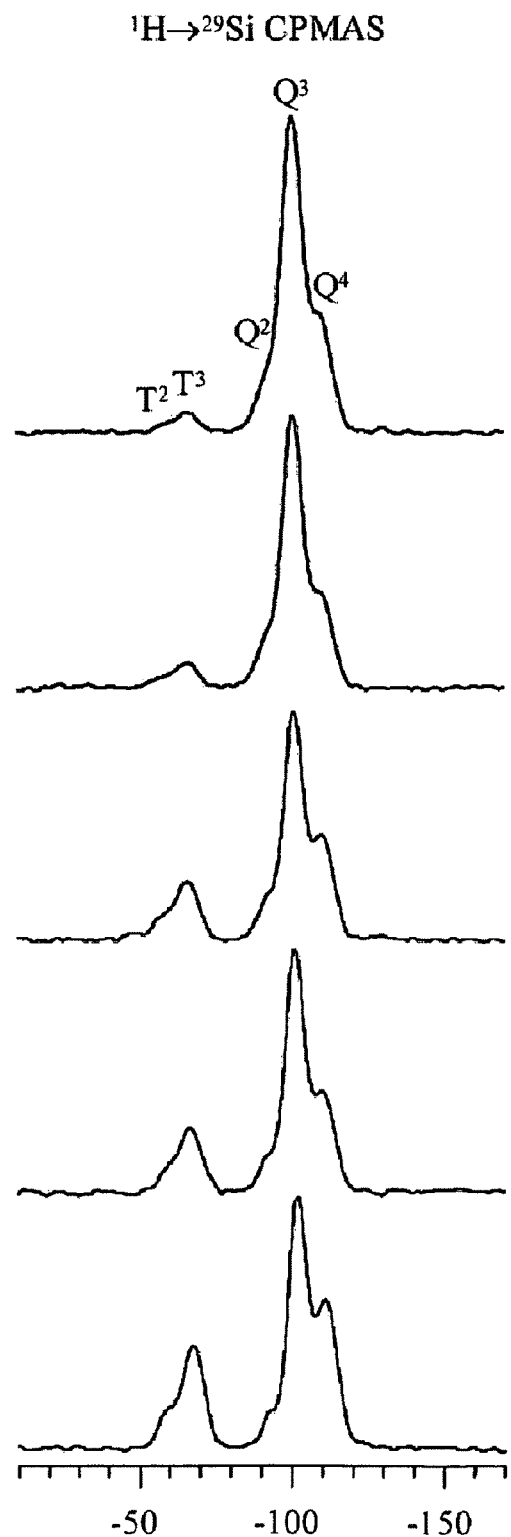
Figure 16C:
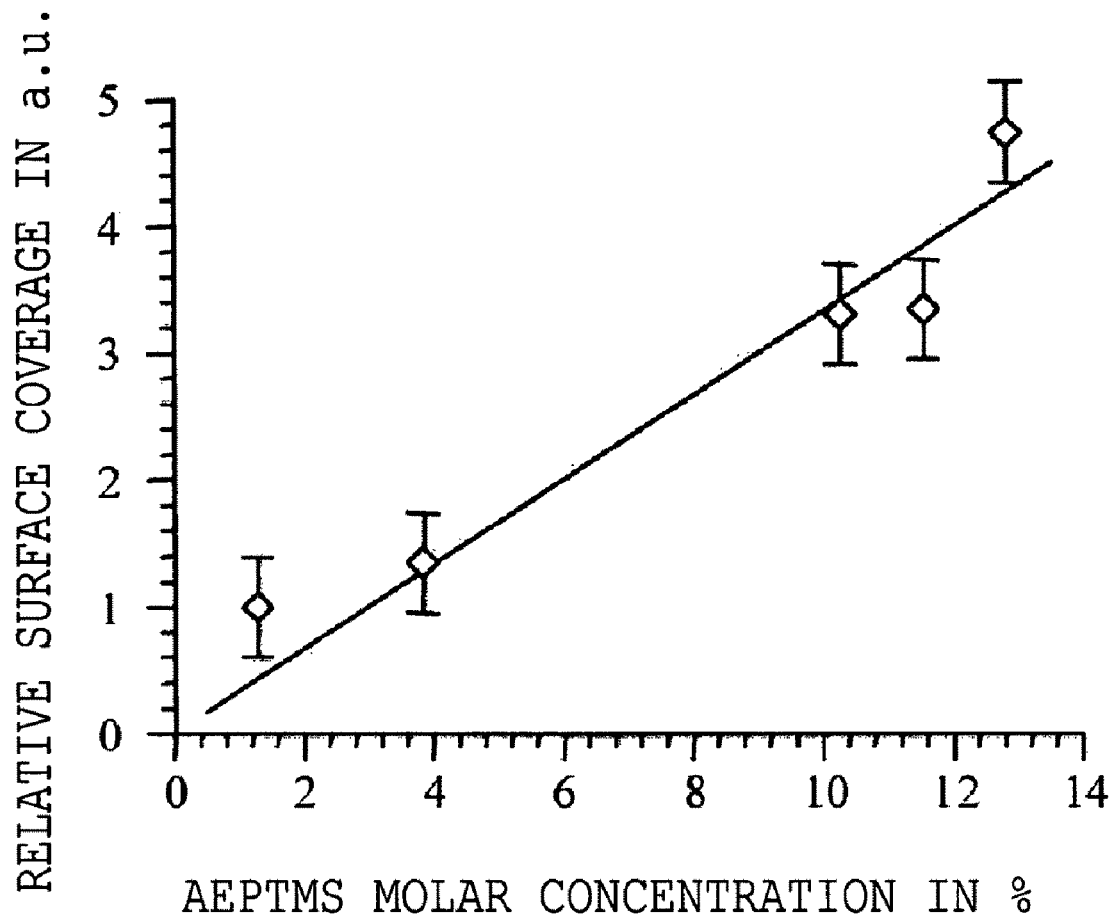
Figure 17A:
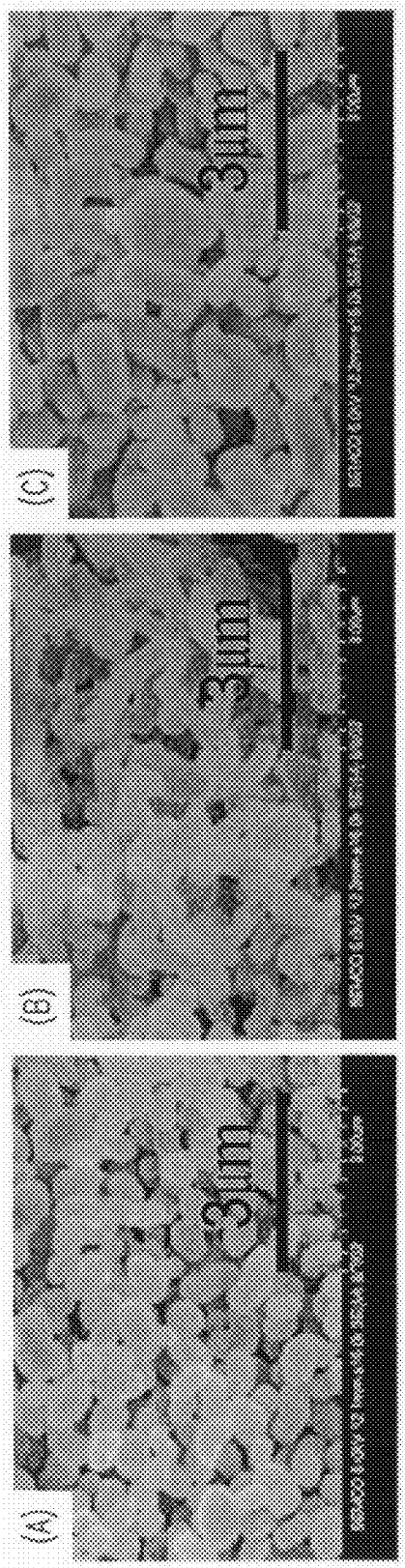
FIG. 17 FE-SEM Images of AEP-MP's with different initial loadings of AEPTMS: 1.28 mol % (a), 3.85 mol % (b), 6.43 mol % (c), 10.27 mol % (d), 11.54 mol % (e), and 12.80 mol % (f). All images are presented using the same scale, with the scale bar=3 μm.
Figure 17B:
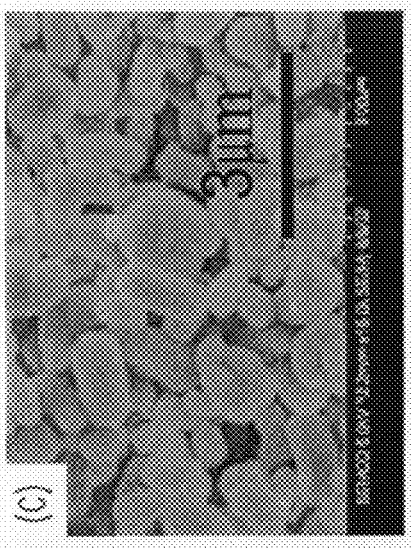
Figure 17C:
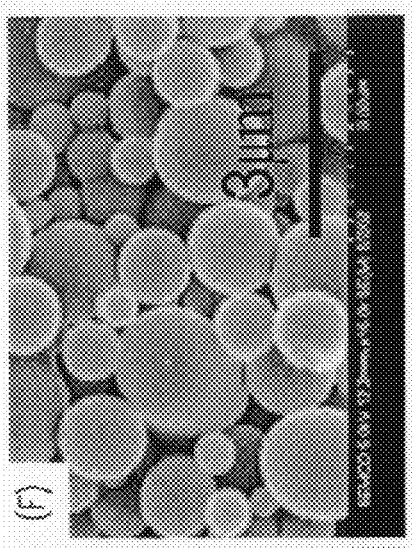
Figure 17D:
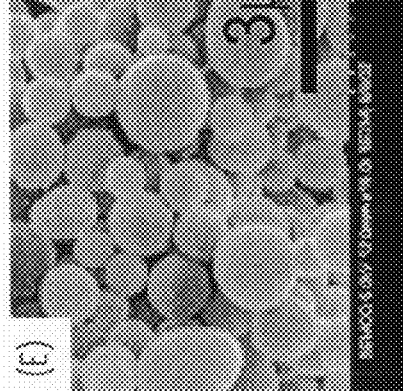
Figure 17E:
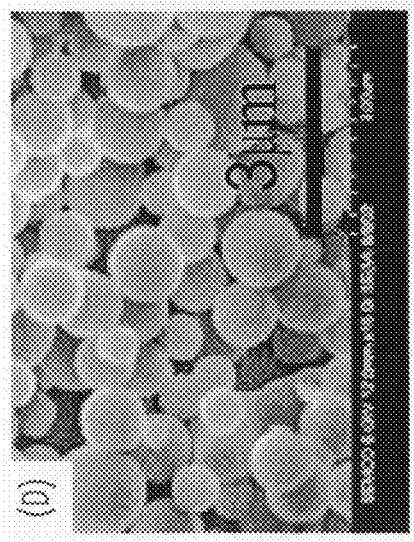
Figure 17F:
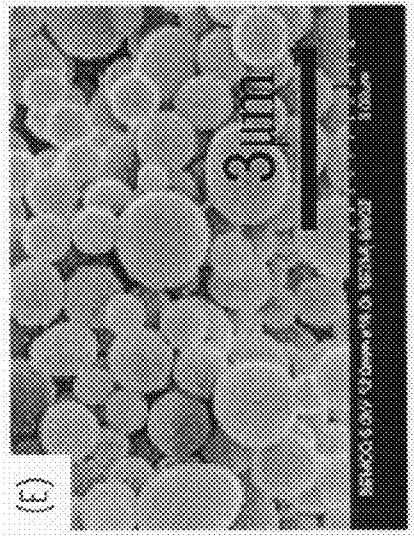
Figures 18A, 18B:
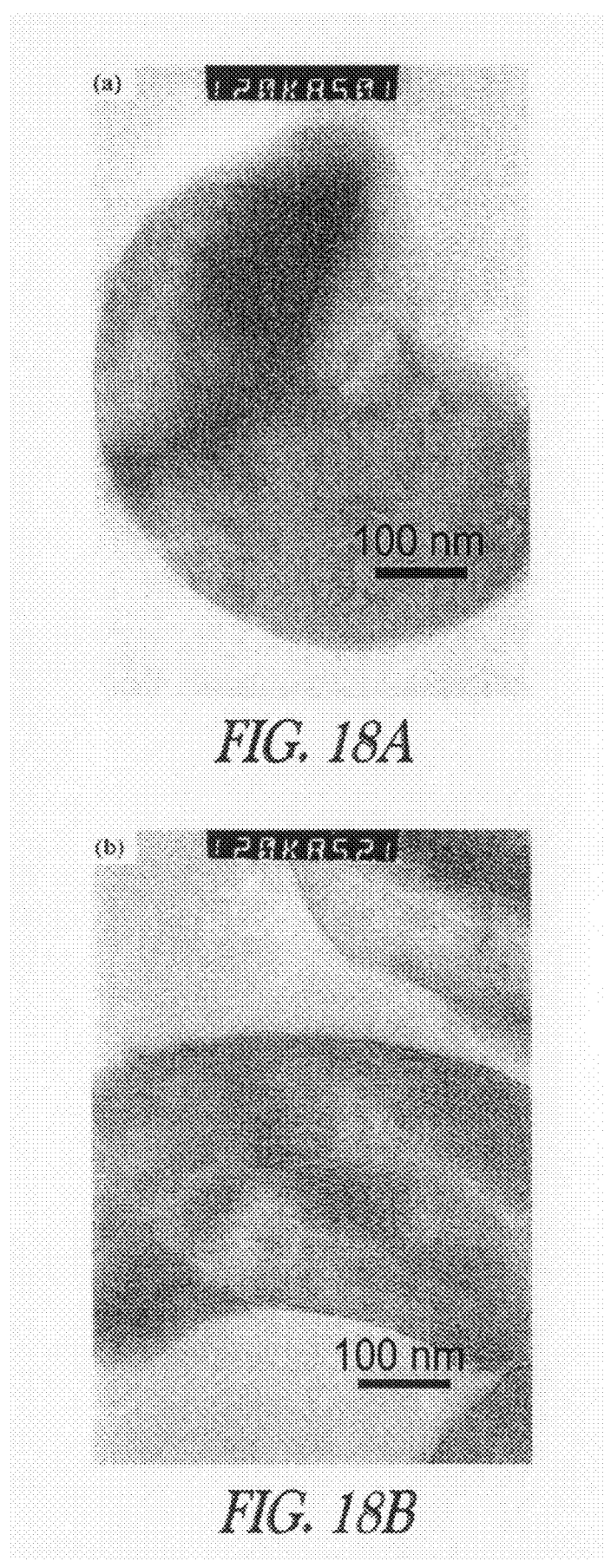

The molar ratio of AEPTMS/TEOS was systematically varied from 1.28 to 12.8 mol %, while the concentrations of all the other chemicals introduced to the co-condensation reaction were fixed at the previously described levels. The incorporation of AEP was quantitatively determined by DPMAS and CPMAS $^{29}Si$ NMR (FIG. 16a and 16b). As discussed earlier, the DPMAS spectra provided quantitative measure of the relative concentrations of $Q^n$ and $T^n$ functionalities. However, due to low concentration of $T^n$ species the SC values were not directly measured in this series of samples. Instead, we used the CPMAS spectra to evaluate the relative change of $T^n$ intensities versus the concentration of AEPTMS. The results, plotted in FIG. 16c in reference to the sample with 1.28 mol % of AEPTMS, showed that the concentration of AEP increased almost linearly as the initial AEPTMS/TEOS molar ratio changed from 1.28 to 12.8 mol %. The particle morphology and mesoporous structure of the resulting materials were analyzed by FE-SEM and TEM. The FE-SEM micrographs of FIG. 17 showed a concurrent transformation of the particle morphology from small kidney bean shaped rods to spheres, with elongated rods and ellipsoidal particles being observed at intermediate concentrations of AEPTMS. Furthermore, a noticeable increase of the average particle sizes of these materials could be observed at higher concentrations of AEPTMS. The TEM micrographs (FIG. 18a and 18b) of the AEP-MP materials with low degrees of functionalization (1.28 and 6.43 mol %, respectively) revealed that the mesopores are uniformly aligned along the long axes of MP's despite of their different particle sizes. This is in contrast to the randomly oriented mesopores observed in the spherical AEP-MP's with the higher degree of functionalization (FIG. 15a).

In one embodiment, the invention provides a mesoporous silicate derived from APTMS, AAPTMS, AEPTMS, UDPTMS, ICPTES, CPTES, ALTMS, TEOS or CTAB, or a combination thereof.

Example 6

Tuning of Particle Morphology and Pore Properties in Mesoporous Silicas with Multiple Organic Functional Groups Example 6 illustrates a synthetic method that can control both multifunctionalization and morphology of mesoporous organic/inorganic hybrid materials by introducing different molar ratios of organoalkoxysilane precursors to base-catalyzed co-condensation reactions.

Recent advances in synthesizing organically functionalized mesoporous silica materials (Lim et al., J. Am. Chem. Soc., 119, 4090 (1997); Stein et al., Adv. Mater., 12, 1403 (2000); Fowler et al., Chem. Commun., 1769 (1997); Hall et al., Chem. Commun., 201 (1999); Fowler et al., Chem. Commun., 1825 (1998); Yang et al., J. Am. Chem. Soc., 124, 9694 (2002); Inagaki et al., Nature, 416, 304 (2002); Fan et al., Nature, 405, 56 (2000)) have highlighted the promising potential of utilizing these materials as building blocks to construct multifunctional microdevices for selective catalysis (Stein et al., Adv. Mater., 12, 1403 (2000); Lin et al., J. Am. Chem. Soc., 124, 9040 (2002); Ying et al., Angew. Chem. Int. Ed., 38, 56 (1999); Sayari, Chem. Mater., 8, 1840 (1996); Moller and Bein, Chem. Mater., 10, 2950 (1998); He and Antonelli, Angew. Chem. Int. Ed., 41, 214 2002); Kageyama et al., Science, 285, 2113 (1999); Davis, Nature, 417, 813 (2002)), adsorption (Dai et al., Angew. Chem., Int. Ed., 38, 1235 (1999); Brown et al., Chem. Commun., 69 (1999); Feng et al., Science, 276, 923 (1997), and sensor (Lin et al., J. Am. Chem. Soc., 123, 11510 (2001); Wirnsberger et al., Chem. Commun., 119 (2001); Descalzo et al., Adv. Mater., 14, 966 (2002)) applications. Further progress in such applications will rely on the ability to tune the extent of functionalization with multiple organic moieties and to control the particle morphology in order to direct the mass-transport properties of the resulting organic/inorganic hybrid materials. Morphology control of inorganic mesoporous silicas has been studied intensively ever since the first report of MCMs family a decade ago. Desired particle shapes have been obtained via pH control (Lin and Mou, Acc. Chem. Res., 35, 927 (2002); Huo et al., Adv. Mater., 9, 974 (1997); Ozin, Chem. Commun., 419 (2000)), utilization of base catalysts (Cai et al., Chem.

Mater., 13, 258 (2001)), and by the use of co-solvents (Anderson et al., Chm. Mater., 10, 1490 (1998); Zhao et al., Chem. Mater., 12, 275 (2000); Etienne et al., New J. Chem., 26, 384 (2002); Schumacher et al., Adv. Mater., 11, 1194 (1999)), e.g. in a modified Stoeber process (Etienne et al., New J. Chem., 26, 384 (2002); (Schumacher et al., Adv. Mater., 11, 1194 (1999)).

Example 6 describes a novel synthetic process of the invention, in which various organoalkoxy-silane precursors introduced during the co-condensation reactions, rather than as co-solvents, are used for morphology control. An added advantage of this method is that it results in simultaneous anchoring of multiple functional groups to the mesopores (multifunctionalization). The roles and quantities of these moieties may be tailored independently and/or cooperatively for various applications, such as gatekeeping.

Figure 19:
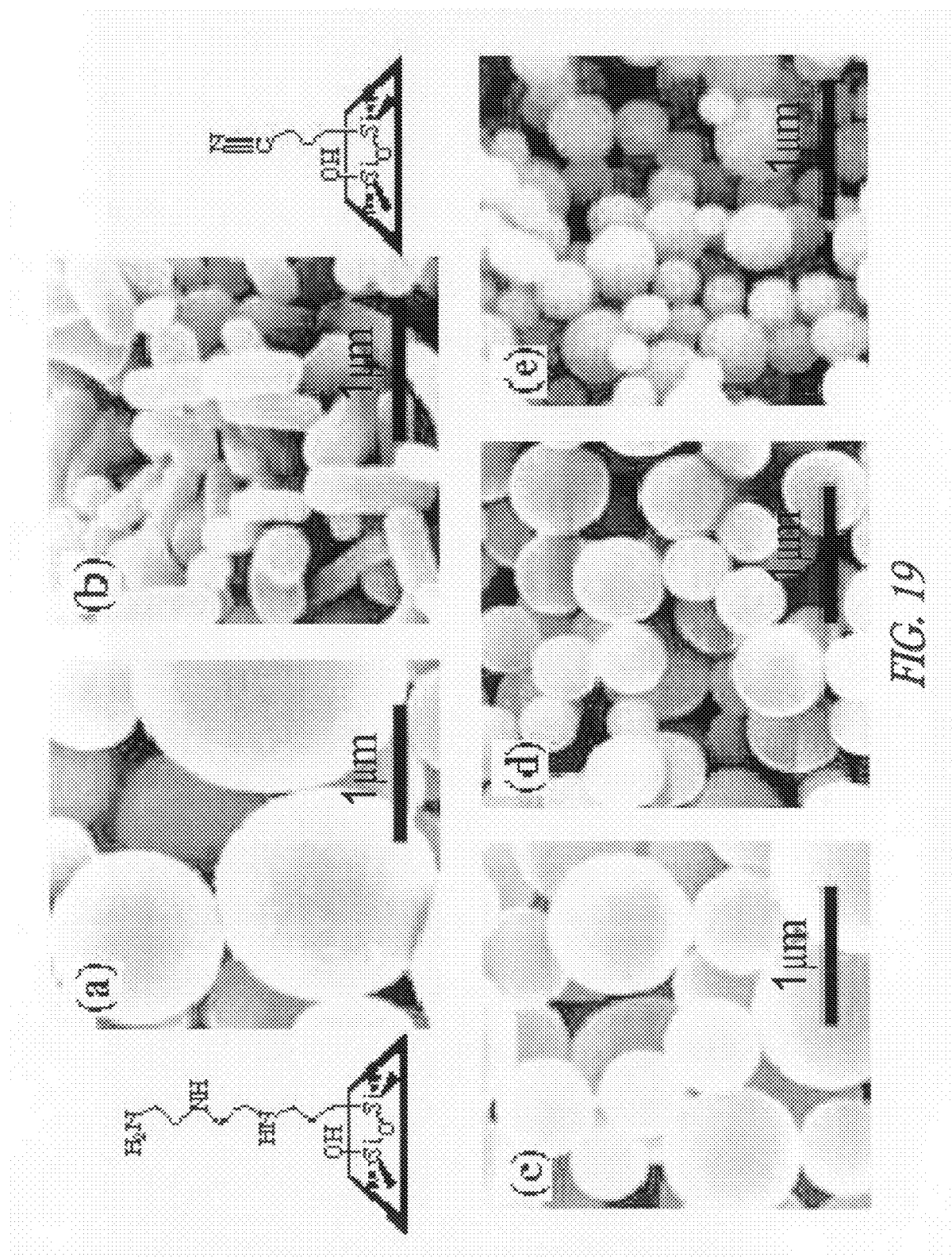
FIG. 19 FE-SEM images of (a) AEP-MP, (b) CP-MP, (c) 5/5 AEP/CP-MP (d) 3/7 AEP/CP-MP, and (e) 1/9 AEP/CP-MP prepared in Example 6 (Scale bar=1 μm for all the micrographs).

The FE-SEM images of two mesoporous silicas functionalized through the introduction of 3-[2-(2-aminoethylamino)ethylamino]propyl (AEP) and 3-cyanopropyl (CP) as organoalkoxysilane precursors, are shown in FIGS. 19a and 19b, respectively Monofunctionalization with AEP or CP resulted in different particle shapes and sizes, i.e., spheres with an average particle diameter=3 µm and rods with an average particle size: L×W=1×0.2 µm. These materials were prepared by sodium hydroxide-catalyzed condensation reactions of tetraethoxysilane (TEOS) with AEP-trimethoxysilane (AEPTMS) or CP-triethoxysilane (CPTES), in the presence of a low concentration of cetyltrimethylammonium bromide (CTAB) surfactant.

A series of bifunctional materials in which the molar ratio between the AEPTMS and CPTES was varied systematically from 100% AEPTMS to 100% CPTES was also synthesized. The total amount of the organoalkoxysilanes (AEPTMS+CPTES) relative to TEOS was fixed at the level of 12.8 mol % in all samples. Herein, the monofunctionalized microparticles are referred to as AEP-MP(CP-MP) and the bifunctionalized materials are referred to as AEP/CP-MP.

As depicted in FIGS. 19c, 19d, and 19e, the FE-SEM micrographs of the bifunctional AEP/CP-MP materials synthesized with different molar ratios of AEPTMS/CPTES showed only spherical particles. In contrast to the micron-sized AEP-MP, the average particle diameters of the bifunctional AEP/CP-MP spheres decreased as the relative ratio of AEPTMS/CPTES changed from 5/5 to 1/9. It is interesting to note that even in the 1/9 case (1.28 mol % of AEPTMS and 11.52 mol % of CPTES, FIG. 19e), no rod-like particles were observed, which is in stark contrast with CP-MP sample (12.8 mol % of CPTES, FIG. 19b). The presence of AEPTMS precursor in the co-condensation reaction played a crucial role in governing the particle shape of the resulting bifunctional materials.

Figure 20A:
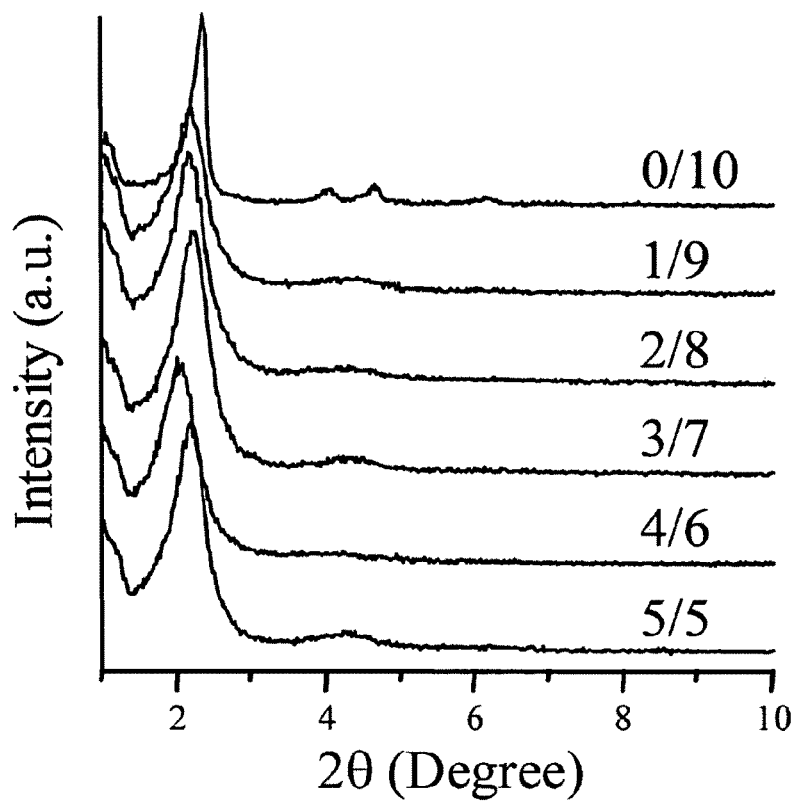
FIG. 20 (a) Powder XRD diffraction patterns of bifunctional AEP/CP-MP materials synthesized with different molar ratios of AEPTMS/CPTES in Example 6. (b) $^{13}C$ solid-state CPMAS NMR measurements of the AEP-MP (above) and CP-MP (below) materials.

To investigate the influence of the organoalkoxysilanes on the pore property and structure, the powder XRD diffraction patterns of the bifunctional samples were measured. As shown in FIG. 20a, the observed patterns exhibited a strong $d_{100}$ peak and a broad peak derived from the combination of $d_{110}$ and $d_{200}$ diffractions, most likely due to a disordered wormhole-like porous structure. This observed diffraction pattern is very similar to that of the AEP-MP material. Also, TEM micrographs revealed the disordered, wormhole pore structure in both AEP-MP and AEP/CP-MP. Interestingly, the XRD (FIG. 20a) and TEM measurements of the CP-MP rods showed a typical MCM-41 type of hexagonal symmetry of the mesopores packed in a parallel fashion along the long axis of the rod-shaped particles. These observations provided further evidence that the sample morphology is sensitive to the presence of AEPTMS during co-condensation.

Figure 20B:
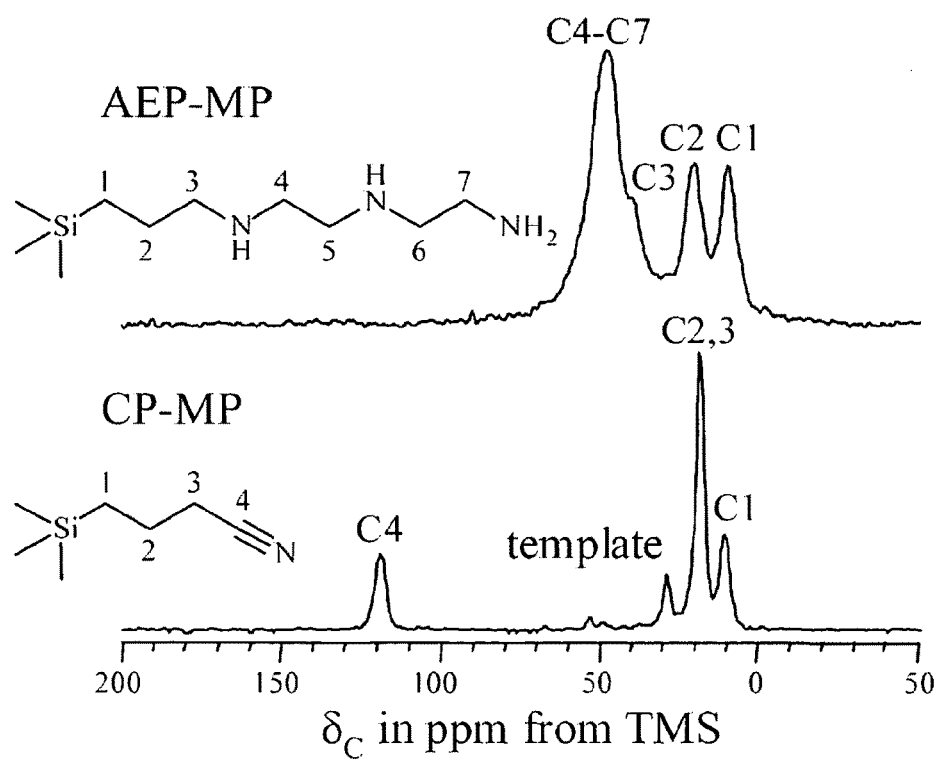

$^{13}$C solid-state NMR was used to (i) obtain spectroscopic evidence for the presence of the organic functional moieties in the mesopores, (ii) confirm their chemical structure, and (iii) measure their relative concentration in bifunctionalized samples. The spectra were obtained at 9.4 T on a Varian/Chemagnetics Infinity spectrometer, using $^1$H-$^{13}$C cross polarization with magic angle spinning (CPMAS) (Pines et al., J. Chem. Phys., 59, 569 (1973)). The spectra, shown in FIG. 20b, demonstrated that the mesopores were indeed functionalized as intended Measurements of the "build-up" of carbon magnetization during cross-polarization revealed details about the molecular motions of both functional groups and allowed to measure their relative concentration in all samples. In AEP-MP, all $CH_2$ carbons were polarized with a time constant $\tau_{CH}$ on the order of 60 µs, which is typical for such functional groups in rigid molecules. A similar time constant has been found for the C1 carbon in CP-MP. However, the evolution of resonance at 19 ppm in this sample involved two time constants of approximately 100 and 700 µs. This result showed that the C2-H$_2$ and C3-H$_2$ groups in CP-MP experienced increasing mobility, which weakened the $^1$H-$^{13}$C dipolar coupling and inhibited the cross polarization process. The $\tau_{CH}$ value of 5 ms observed for carbon C4 was consistent with the nitrile end of CP-MP being the most mobile.

Figure 21:
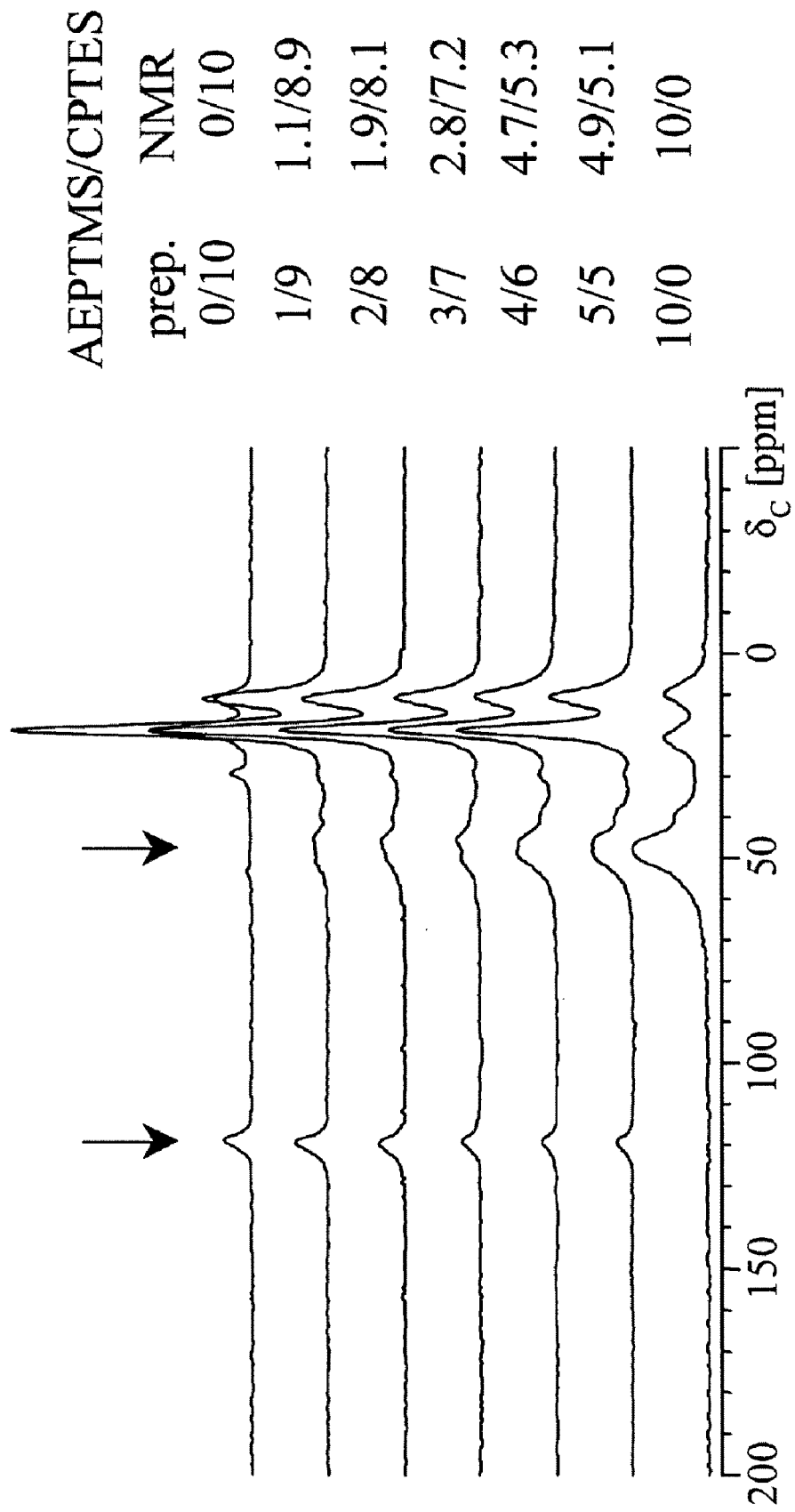
FIG. 21 $^{13}C$ CPMAS spectra of monofunctionalized (top and bottom traces) and bifunctionalized (middle traces) AEP/CP-MP's prepared in Example 6. Arrows highlight the resonances that are unique for each species and thus were used for quantitative analysis. The numbers represent the molar ratio between two components used for preparation (left column) and obtained form analysis of NMR spectra (right column).

Measurements also showed that in the AEP/CP-MP samples the cross polarization dynamics was the same, within the experimental error, as for the corresponding carbon species in AEP-MP and CP-MP. This allowed the physical mixture of AEP-MP with CP-MP in a known molar ratio to be used as the intensity standard for quantitative analysis of the spectra of bifunctionalized samples, which are shown in FIG. 21. Two unique resonances, at around 48 ppm in AEP (carbons C4-C7) and at 120 ppm in CP (carbon C4), offered best indicators of both functionalities.

Figure 22:
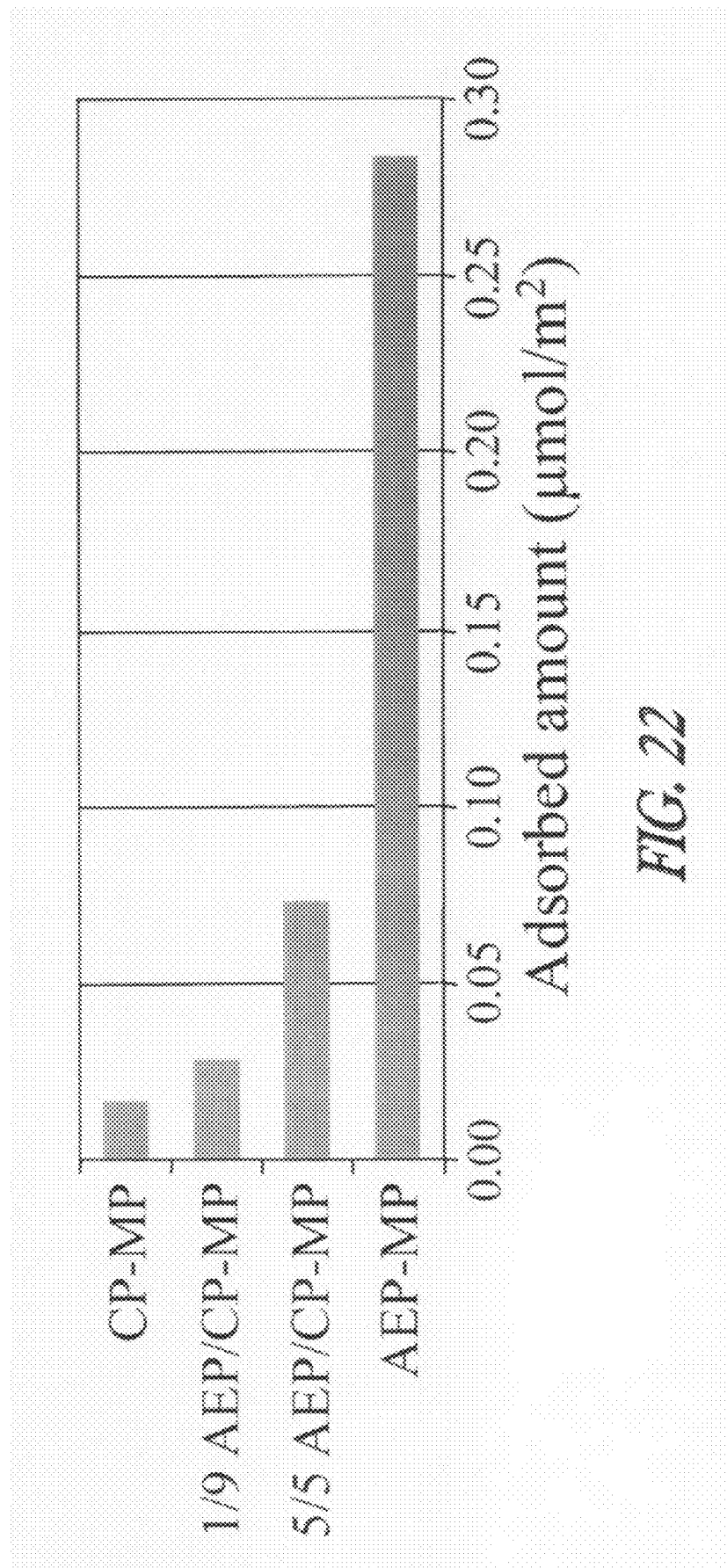
FIG. 22 Is a diagram of Cu(II) adsorption capacity for selected samples prepared in Example 6.

In order to investigate the chemical accessibility of the organic functional groups, the $Cu^{2+}$ adsorption capacity of representative samples was examined (Burleigh et al., Chem. Mater., 13, 4760 (2001)). Because of the chelate effect of the diethylene triamine moiety of the AEP group, significantly higher $Cu^{2+}$ adsorption capacities for the materials with higher amount of AEP were anticipated. Indeed, our results indicated that the AEP-MP and CP-MP materials showed adsorptivities of 0.284 and 0.017 µmol/m$^2$, respectively (FIG. 22). The corresponding values for bifunctional 5/5 and 1/9 AEP/CP-MP silicas were 0.073 and 0.028 µmol/m$^2$. However, that the $Cu^{2+}$ adsorption capacity increased by a factor of only 2.6 between the 1/9 to 5/5 AEP/CP-MP samples, whereas solid state NMR showed an 8-fold increase of the relative AEP/CP ratio in these materials. Given that the total loading of both organic groups was fixed at 12.8 mol %, these results indicated that the chemical accessibility of organic functional groups did not increase linearly with the amount of AEP groups in bifunctional silicas. The CP functionality, which is hydrophobic in nature, might have played an active role in decreasing the adsorption capacity per AEP group.

Example 7

The following illustrate representative pharmaceutical dosage forms, containing a loaded mesoporous silica particle of the invention ('Particle X'), for therapeutic or prophylactic use in humans.

| (i) Tablet 1 | mg/tablet |
|---|---|
| >Particle X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| >Particle X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| >Particle X = | 10.0 |
| Colloidal silicon dioxide | 1.5 |
| Lactose | 465.5 |
| Pregelatinized starch | 120. |
| Magnesium stearate | 3.0 |
| | 600.0 |

| (iv) Injection 1 (1 mg/mL) | mg/mL |
|---|---|
| >Particle X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| >Particle X = (free acid form) | 10.0 |
| Monobasic sodium phosphate | 0.3 |
| Dibasic sodium phosphate | 1.1 |
| Polyethylene glycol 400 | 200.0 |
| 0.1 N Sodium hydroxide solution (pH adjustment to 7.0-7.5) | q.s. |
| Water for injection | q.s. ad 1 mL |

| (vi) Aerosol | mg/can |
|---|---|
| >Particle X = | 20.0 |
| Oleic acid | 10.0 |
| Trichloromonofluoromethane | 5,000 |
| Dichlorodifluoromethane | 10,000 |
| Dichlorotetrafluoroethane | 5,000 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A particle comprising an approximately spherical mesoporous silicate body having a multiplicity of pores, and one or more removable caps obstructing one or more of the pores;
   wherein the mesoporous silicate body has a particle size of less than about 750 nm and the pores of the mesoporous silicate body have a diameter of less than about 50 nm;
   wherein the one or more caps comprise an organic polymer covalently bonded to the mesoporous silicate body through a linking group of formula X—CH$_2$CH$_2$CH$_2$SSCH$_2$CH$_2$NHC(=O)CH$_2$—Y, wherein X is a silicon atom of the mesoporous silicate and Y is an atom of the organic polymer.

2. The particle of claim 1 wherein the pores are about 1-50 nm in diameter.

3. The particle of claim 1 wherein the pores are less than about 40 nm in diameter.

4. The particle of claim 1 wherein the pores are less than about 30 nm in diameter.

5. The particle of claim 1 wherein the pore wall thickness of the particle is about 18 angstroms to about 23 angstroms.

6. The particle of claim 1 wherein the organic polymer is a dendrimer, a biopolymer, or a polymeric nanosphere.

7. The particle of claim 6 wherein the dendrimer is a cationic dendrimer or an anionic dendrimer.

8. The particle of claim 6 wherein the dendrimer is a biodegradable poly(amidoamine) dendrimer.

9. The particle of claim 6 wherein the organic polymer is a biopolymer and the biopolymer is a protein, a polypeptide, an oligonucleotide, or an oligosaccharide.

10. The particle of claim 6 wherein the organic polymer is poly(lactic acid).

11. The particle of claim 1 wherein the particle is spherical.

12. The particle of claim 1 further comprising an encapsulated agent enclosed in one or more of the pores.

13. The particle of claim 12 wherein the encapsulated agent is a bioactive agent, a therapeutic agent, or a diagnostic agent.

14. The particle of claim 13 wherein the encapsulated agent is a chemotherapeutic agent, a chelated radionuclide, an immunosuppressive drug, an anti-inflammatory agent, an antibacterial agent, an antifungal agent, an antiviral agent, an analgesic agent, a polypeptide, a hormone, a hormonal messenger, a cytokine, an imaging agent, a contrast agent, an enzyme, a vitamin, a cosmetic agent, a nutrient, a gene expression suppressive drug, a neurotransmitter, a RNA molecule, or a DNA molecule.

15. A pharmaceutical composition comprising a particle as described in claim 13 and a pharmaceutically acceptable carrier.

16. The composition of claim 15 which is formulated for oral administration, for topical administration, or for administration by injection.

17. The particle of claim 1 wherein the mesoporous silicate body is a sphere having a diameter of less than about 300 nm.

18. The particle of claim 1 wherein the mesoporous silicate body is a sphere having a diameter of less than about 100 nm.

19. The particle of claim 1 wherein the mesoporous silicate body has a surface area of about 600 m$^2$/g to about 1,100 m$^2$/g.

20. The particle of claim 1 wherein the mesoporous silicate body has a loading capacity for encapsulated agents equivalent to more than 18 μmol per 100 mg of particles.

21. The particle of claim 1 wherein the mesopore volume of the particle is about 0.4 cm$^3$/g to about 0.8 cm$^3$/g.

22. The particle of claim 1 wherein the surface coverage of the one or more mercaptoalkyl, haloalkyl, aminoalkyl, carboxyalkyl, ureaalkyl, (carbamic acid)alkyl, cyanoalkyl, sulfonylalkyl, arylalkyl, alkynyl, or alkenyl groups on the particle is about 13% to about 33%.

* * * * *